(12) United States Patent
Fuchiwaki et al.

(10) Patent No.: US 9,947,875 B2
(45) Date of Patent: Apr. 17, 2018

(54) AMINE DERIVATIVES, MATERIAL FOR ORGANIC ELECTROLUMINESCENT DEVICE AND ORGANIC ELECTROLUMINESCENT DEVICE INCLUDING THE SAME

(71) Applicant: SAMSUNG DISPLAY CO., LTD., Yongin-si, Gyeonggi-do (KR)

(72) Inventors: Junta Fuchiwaki, Yokohama (JP); Koushin Matsuoka, Yokohama (JP); Hiroaki Itoi, Yokohama (JP)

(73) Assignee: Samsung Display Co., Ltd., Yongin-si (KR)

( * ) Notice: Subject to any disclaimer, the term of this patent is extended or adjusted under 35 U.S.C. 154(b) by 223 days.

(21) Appl. No.: 14/876,656

(22) Filed: Oct. 6, 2015

(65) Prior Publication Data

US 2016/0126467 A1 May 5, 2016

(30) Foreign Application Priority Data

Oct. 29, 2014 (JP) ................................. 2014-220210

(51) Int. Cl.
*H01L 51/54* (2006.01)
*C09K 11/06* (2006.01)
*H01L 51/00* (2006.01)
*C07D 307/91* (2006.01)
*H01L 51/50* (2006.01)

(52) U.S. Cl.
CPC ........ *H01L 51/0061* (2013.01); *C07D 307/91* (2013.01); *H01L 51/0073* (2013.01); *H01L 51/5056* (2013.01)

(58) Field of Classification Search
CPC . C07D 307/77; C07D 307/91; H01L 51/0032; H01L 51/005; H01L 51/0059; H01L 51/0051; H01L 51/0071; H01L 51/0073; H01L 51/50; H01L 51/5056; H01L 51/5088
USPC ....... 428/690, 691, 917, 411.4, 336; 427/58, 427/66; 313/500–512; 257/40, 88–104, 257/E51.001–E51.052; 252/301.16–301.35
See application file for complete search history.

(56) References Cited

U.S. PATENT DOCUMENTS 9,024,521 B2    5/2015  Yoshinaga et al.
2012/0248426 A1* 10/2012  Kato ................... C07D 209/86
                                                257/40
2014/0167003 A1*  6/2014  Kato ................... H01L 51/0059
                                                257/40

FOREIGN PATENT DOCUMENTS

| EP | 2 665 342 A1 | 11/2013 |
| JP | 2008-21687 A | 1/2008 |
| JP | 2009-29726 A | 2/2009 |
| JP | 2009-267255 A | 11/2009 |
| JP | 2013-236055 A | 11/2013 |
| WO | WO 2010/061824 A1 | 6/2010 |
| WO | WO 2010/114017 A1 | 10/2010 |
| WO | WO 2011/021520 A1 | 2/2011 |
| WO | WO 2011/059099 A1 | 5/2011 |

* cited by examiner

*Primary Examiner* — Andrew K Bohaty
(74) *Attorney, Agent, or Firm* — Lewis Roca Rothgerber Christie LLP

(57) ABSTRACT

A material for an organic electroluminescent device having high emission efficiency and an organic electroluminescent device including the same. An amine derivative of an embodiment of the inventive concept is represented by Formula (1).

Formula 1

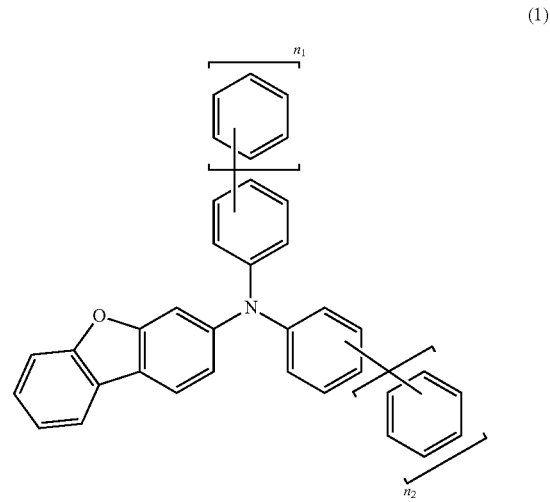

14 Claims, 1 Drawing Sheet

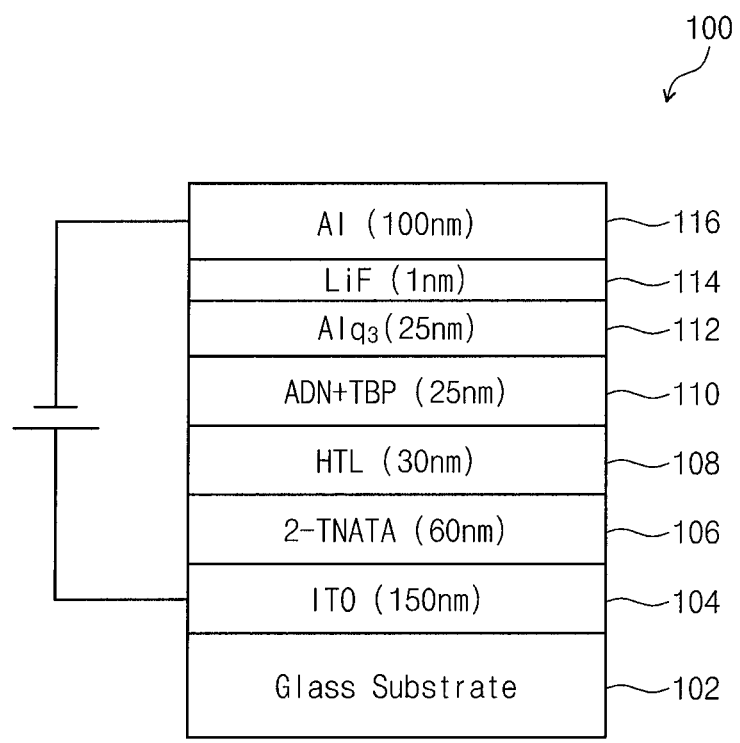

AMINE DERIVATIVES, MATERIAL FOR ORGANIC ELECTROLUMINESCENT DEVICE AND ORGANIC ELECTROLUMINESCENT DEVICE INCLUDING THE SAME

CROSS-REFERENCE TO RELATED APPLICATION

This patent application claims priority to and the benefit of Japanese Patent Application No. 2014-220210, filed on Oct. 29, 2014, the entire content of which is incorporated herein by reference.

BACKGROUND

The present disclosure herein relates to an amine derivative, a material for an organic electroluminescent device and an organic electroluminescent device including the same, and more particularly, to a material for an organic electroluminescent device having high emission efficiency in a blue emission region and an organic electroluminescent device including the same.

In recent years, organic electroluminescent (EL) displays as one kind of image displays have been actively developed. Unlike liquid crystal displays and the like, organic EL displays are so-called self-luminescent displays which display images by emitting light from a luminescent material including an organic compound in the emission layer through recombination of holes and electrons injected from an anode and a cathode in the emission layer.

An example of an organic EL device known in the art is an organic EL device which includes an anode, a hole transport layer disposed on the anode, an emission layer disposed on the hole transport layer, an electron transport layer disposed on the emission layer, and a cathode disposed on the electron transport layer. Holes injected from the anode are injected via the hole transport layer into the emission layer. Meanwhile, electrons are injected from the cathode, and the injected electrons are injected via the electron transport layer into the emission layer. The holes and the electrons injected into the emission layer recombine to generate excitons within the emission layer. The organic EL device emits light generated by deactivation radiation of the excitons. The organic EL devices are not limited to the above-described configuration but may be changed to various suitable forms.

When organic EL devices are applied in display apparatuses, the low driving voltage, high emission efficiency and long life (i.e., lifetime or lifespan) of the organic EL device are required. To realize the low driving voltage, high emission efficiency and long life of the organic EL device, stabilization and normalization of the hole transport layer are contemplated. Aromatic amine-based compounds have been known as a hole transport material utilized in the hole transport layer, however, due to the low carrier resistance, there is a limitation in the life of the organic EL device. As a useful material for expanding the life of the organic EL device, for example, an amine derivative substituted with a heteroaryl ring has been suggested.

However, the suggested hole transport material is not considered to have sufficient emission efficiency. Particularly, since the emission efficiency of an organic EL device in a blue emission region is lower than in a red emission region and a green emission region, an increase in the emission efficiency in the blue emission region is required. In addition, since high temperature resistance of the organic EL device provided with the suggested hole transport material is not sufficient, a development of a novel material is required.

SUMMARY

According to an embodiment of the inventive concept, an amine derivative is represented by following Formula 1.

Formula 1

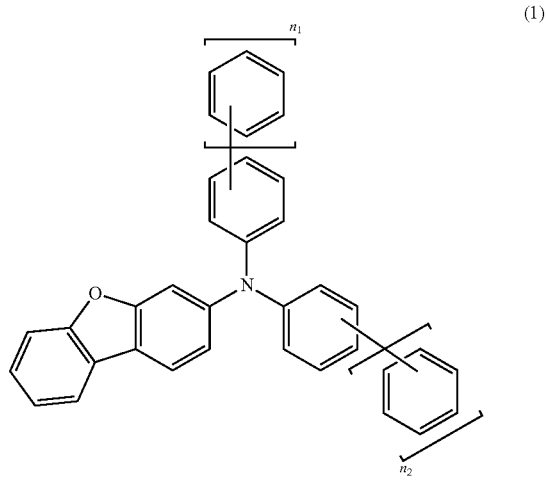

(1)

In Formula 1, $n_1$ is an integer from 1 to 4, $n_2$ is an integer from 2 to 4, and $n_1+n_2$ is at least 4.

The amine derivative according to an embodiment of the inventive concept may have high emission efficiency and high temperature resistance by introducing 3-substituted dibenzofuran into an amine.

In the amine derivative, $n_1$ may be 2 and $n_2$ may be 2.

The amine derivative according to an embodiment of the inventive concept may have high emission efficiency and high temperature resistance by introducing 3-substituted dibenzofuran and 2 (two) terphenyl groups into an amine.

In the amine derivative, a first arylene group binding to a nitrogen atom in Formula 1 may bind to a second arylene group or an aryl group at a para position of the first arylene group binding to the nitrogen atom.

The amine derivative according to an embodiment of the inventive concept may have high emission efficiency and high temperature resistance by binding the second arylene group or the aryl group at the para position of the first arylene group binding to the nitrogen atom.

In the amine derivative, all arylene groups and aryl groups which bind to the first arylene group binding to the nitrogen atom in Formula 1 may bind at the para position of an adjacent arylene group.

The amine derivative according to an embodiment of the inventive concept may have high emission efficiency and high temperature resistance by binding all arylene groups and aryl groups at the para position of the arylene group binding to the nitrogen atom or the arylene group interposed therebetween.

In an embodiment of the inventive concept, a material for an organic electroluminescent device includes any one of the amine derivatives described above.

The material for an organic electroluminescent device according to an embodiment of the inventive concept may include the amine derivative to thereby allow an organic electroluminescent device having high emission efficiency and high temperature resistance to be prepared.

In an embodiment of the inventive concept, an organic electroluminescent device includes the material for an organic electroluminescent device in at least one layer between an emission layer and an anode.

The organic electroluminescent device according to an embodiment of the inventive concept may utilize the material for an organic electroluminescent device in which 3-substituted dibenzofuran is introduced into an amine in one membrane of lamination membranes (e.g., in one layer of a plurality of layers) disposed between an emission layer and an anode, and thus high emission efficiency and high temperature resistance may be realized. In particular, a great effect may be achieved in a blue region.

BRIEF DESCRIPTION OF THE FIGURE

The accompanying drawing is included to provide a further understanding of the inventive concept, and are incorporated in and constitute a part of this specification. The drawing illustrates example embodiments of the inventive concept and, together with the description, serves to explain principles of the inventive concept. The drawing is a schematic diagram of an organic electroluminescent device according to an embodiment of the inventive concept.

DETAILED DESCRIPTION

Example embodiments of the inventive concept will be described below in more detail with reference to the accompanying drawing. The inventive concept may, however, be embodied in different forms and should not be construed as limited to the embodiments set forth herein. Rather, these embodiments are provided so that this disclosure will be thorough and complete, and will fully convey the scope of the inventive concept to those skilled in the art.

Hereinafter, example embodiments of the inventive concept will be described in more detail with reference to the accompanying drawing.

Through thoughtful examination to resolve the limitation described above, present inventors have found that high emission efficiency and high temperature resistance of an organic electroluminescent (EL) device may be achieved by directly binding 3-substituted dibenzofuran to a nitrogen atom of an amine in an amine derivative.

Hereinafter, an amine derivative, a material for an organic EL device, and an organic EL device including the same according to an embodiment of the inventive concept will be described in more detailed with reference to the accompanying drawing. The amine derivative, the material for an organic EL device, and the organic EL device including the same according to an embodiment of the inventive concept may, however, be embodied in various different forms and should not be construed as limited to the embodiments set forth hereinafter. In the description and drawing, elements having substantially the same function are designated by the same reference numerals, and repeated explanation thereof will be omitted The amine derivative according to an embodiment of the inventive concept has a diphenylamine structure represented by following Formula 1 in which 3-substituted dibenzofuran directly binds to a nitrogen atom of an amine.

Formula 1

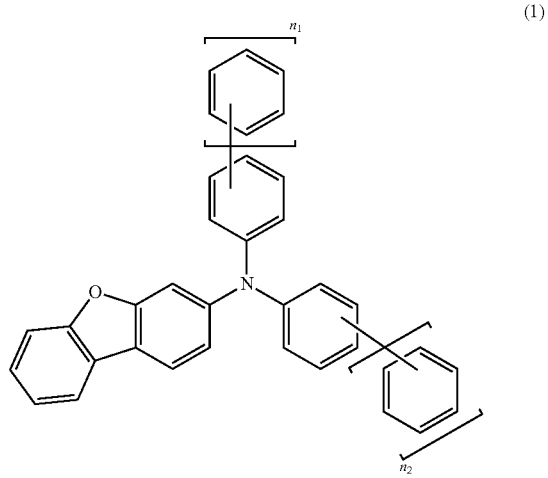

In Formula 1, $n_1$ is an integer from 1 or more to 4 or less (i.e., $n_1$ is an integer from 1 to 4), $n_2$ is an integer from 2 or more to 4 or less (i.e., $n_2$ is an integer from 2 to 4), and $n_1+n_2$ is at least 4. Here, the nitrogen atom of the amine derivative represented by Formula 1 is directly linked to the third carbon of a dibenzofuran group, and further directly linked to two arylene groups (each of the arylene groups that are directly linked to the nitrogen atom is also referred to as a first arylene group hereinafter), where each of the two first arylene groups that are directly linked to the nitrogen atom is further linked to an aryl group with additional arylene groups interposed therebetween (when $n_1$ is two or greater), or one of the two first arylene groups (i.e., the first arylene group that is directly linked to the groups with $n_2$ as the subscript) that are directly linked to the nitrogen atom is further linked to an aryl group with additional arylene groups interposed therebetween and the other one of the two first arylene groups (i.e., the first arylene group that is directly linked to the groups with $n_1$ as the subscript) that are directly linked to the nitrogen atom is further directly linked to an aryl group without additional arylene groups interposed therebetween (when $n_1$ is one). The additional arylene group that is interposed between the first arylene group and the aryl group is also referred to as the second arylene group hereinafter. An amine (e.g., amine derivative) having a nitrogen atom, to which a substituent larger than a pentaphenyl group (e.g., $n_1$ and/or $n_2$ is 6 or greater) binds, is not preferably utilized as a material for membrane formulation (e.g., film formulation) in deposition.

In addition, in one embodiment, each of $n_1$ and $n_2$ is 2. Namely, in an embodiment, an amine derivative has 2 terphenyl groups. The amine derivative according to an embodiment of the inventive concept may have high emission efficiency and high temperature resistance by introducing 3-substituted dibenzofuran and 2 terphenyl groups into an amine.

Further, in an embodiment, a first arylene group binding directly to the nitrogen atom in Formula 1 may bind to a second arylene group or an aryl group at the para position of the first arylene group binding to the nitrogen atom. In another embodiment, all groups which bind to the first arylene group binding to the nitrogen atom in Formula 1 may bind at the para position of an adjacent arylene group. The amine derivative according to an embodiment of the inventive concept may have high emission efficiency and high temperature resistance by binding the arylene group and aryl group, which bind (e.g., bind directly) to the arylene group binding to the nitrogen atom, at the para position, and emission efficiency and high temperature resistance may be more enhanced by binding all arylene groups and aryl groups to a respective adjacent arylene group at the para position.

In an embodiment of the inventive concept, the amine derivative represented by Formula 1 may be utilized as a material for an organic EL device. The material for an organic EL device according to an embodiment of the inventive concept may include the amine derivative having the structure described above to thereby allow an organic EL device having high emission efficiency and high temperature resistance to be prepared.

The amine derivative according to an embodiment of the inventive concept may include at least one of compounds 1 to 6 below.

1

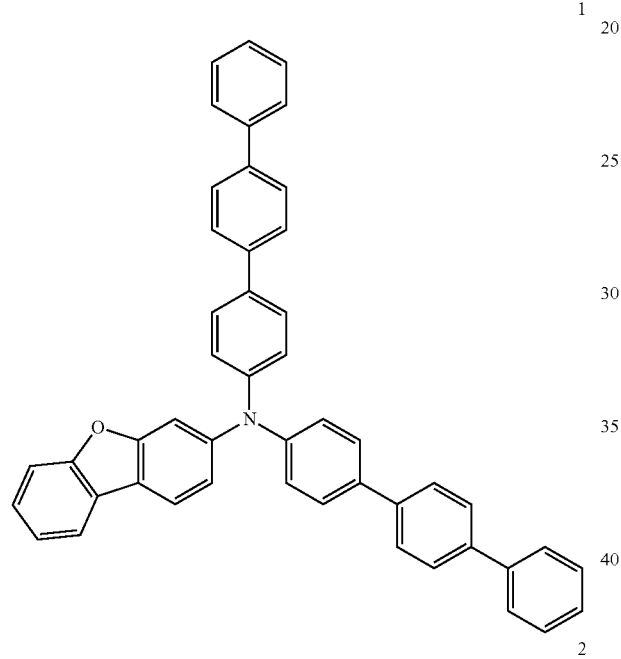

2

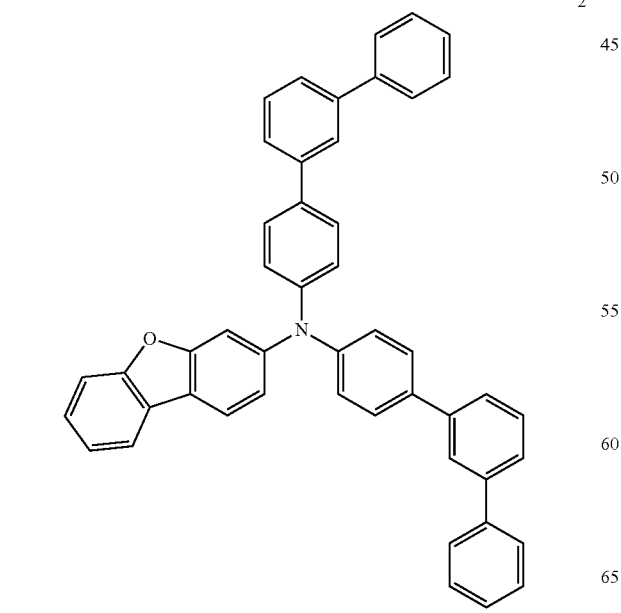

-continued

3

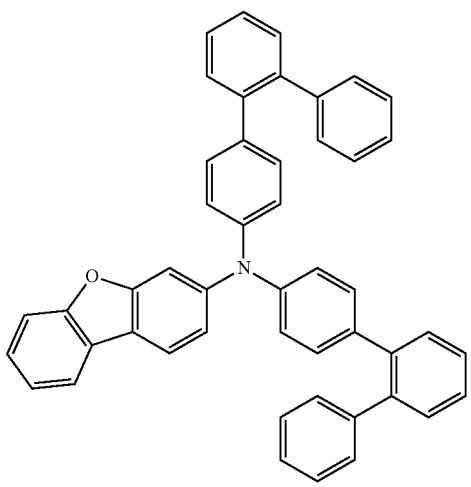

4

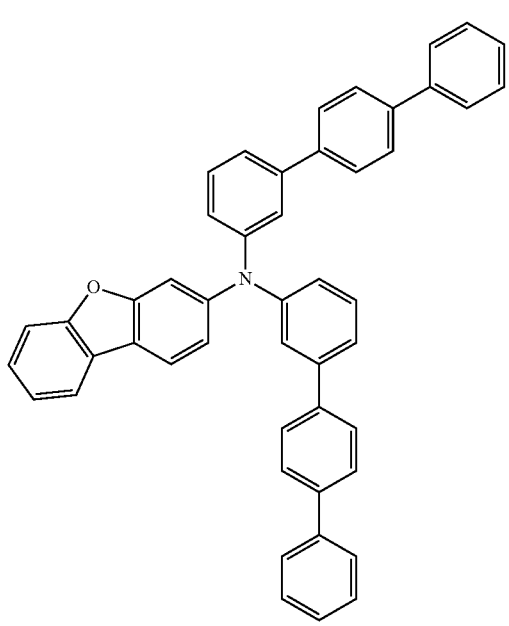

5

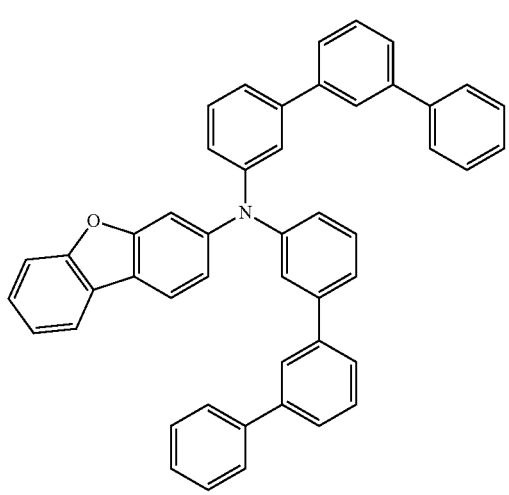

6
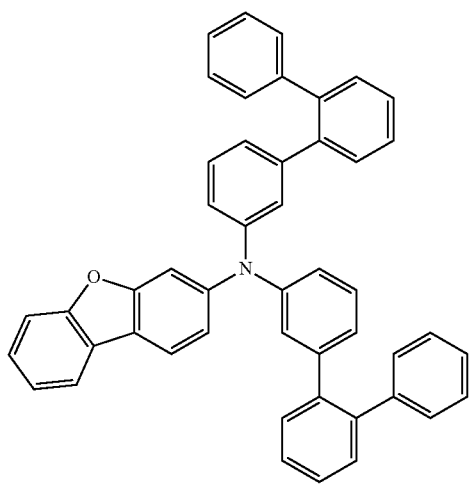
The amine derivative according to an embodiment of the inventive concept may include at least one of compounds 7 to 15 below.
7
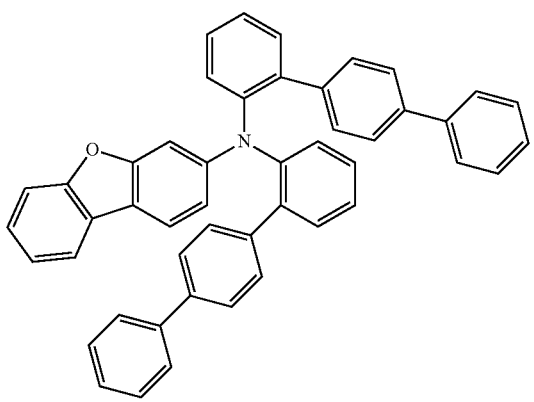
8
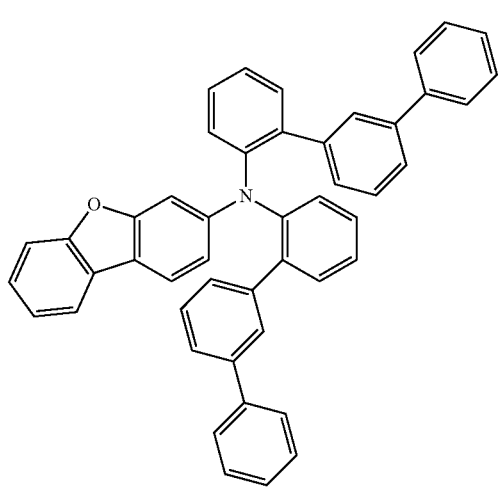
9
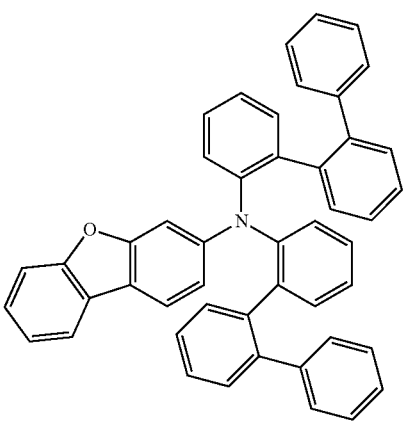
10
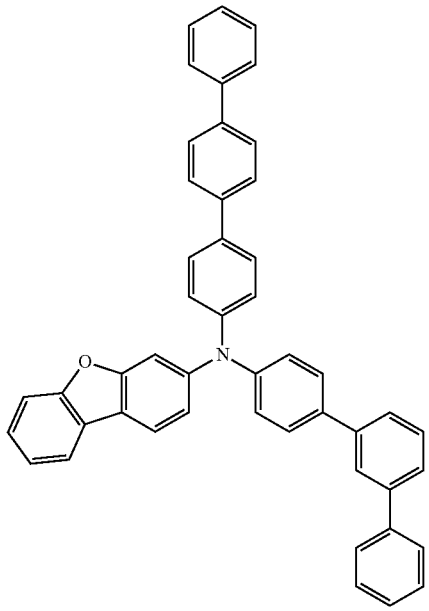
11
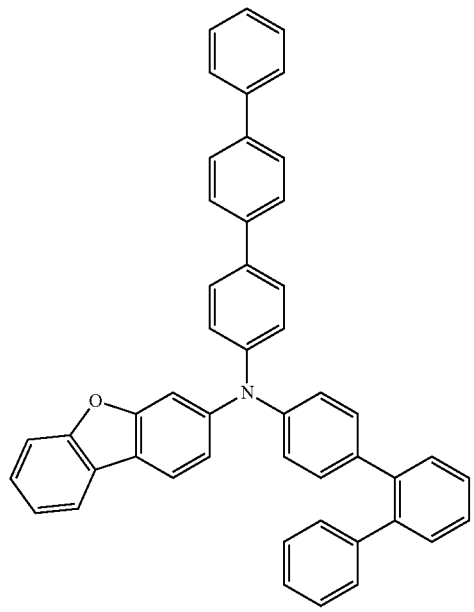

12
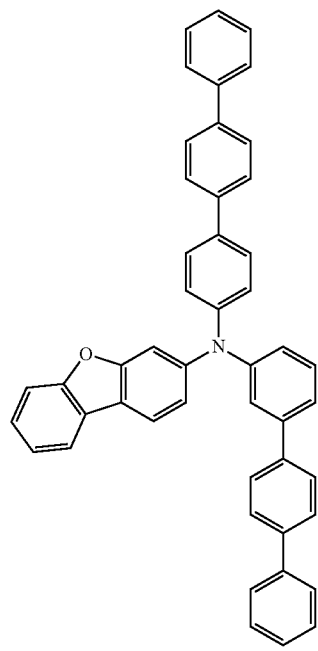
13
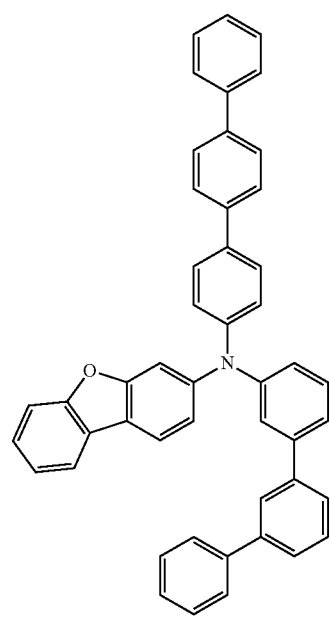
14
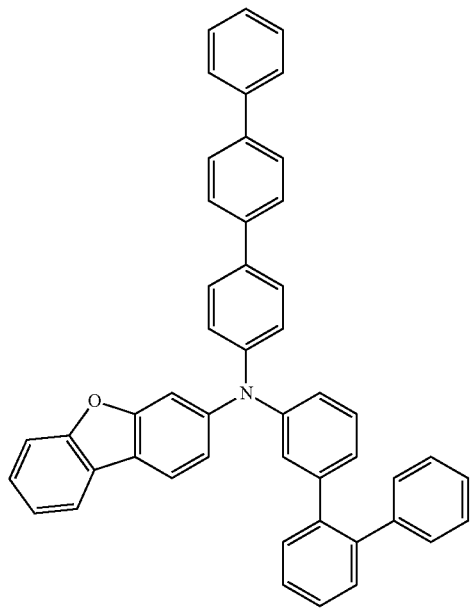
15
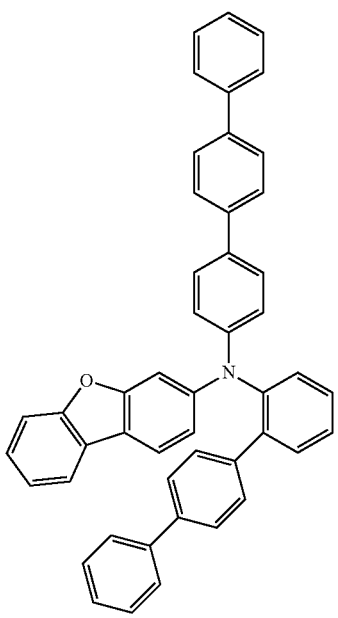
The amine derivative according to an embodiment of the inventive concept may include at least one of compounds 16 to 24 below.

16
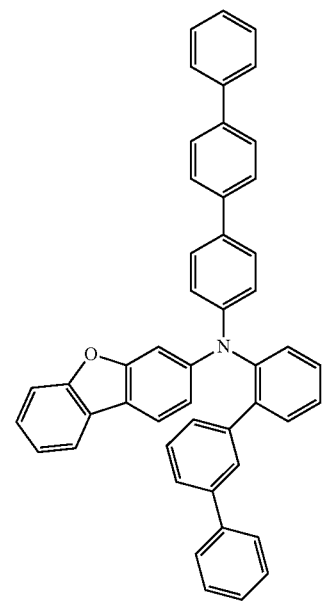
17
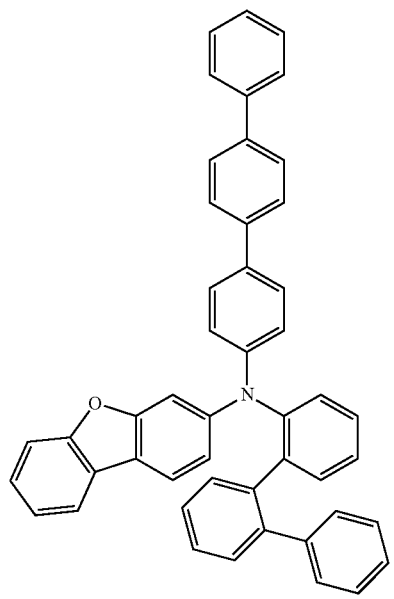
18
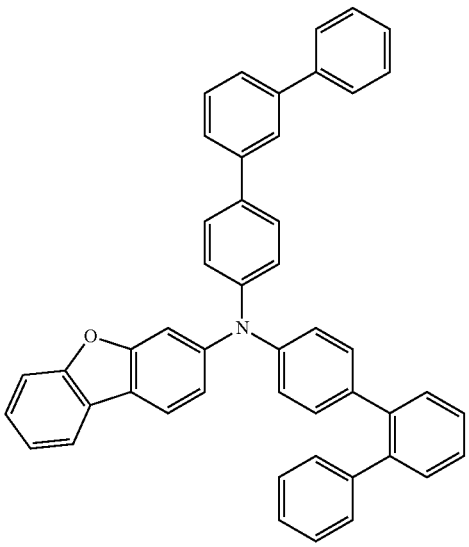
19
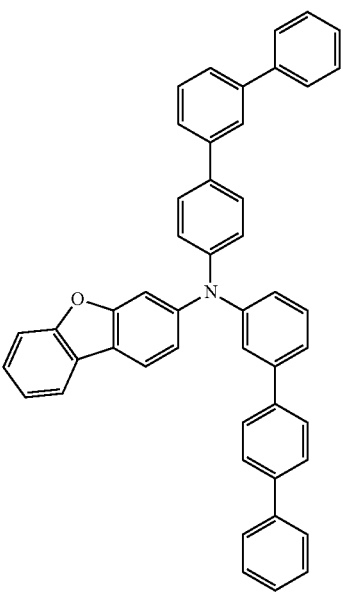

20
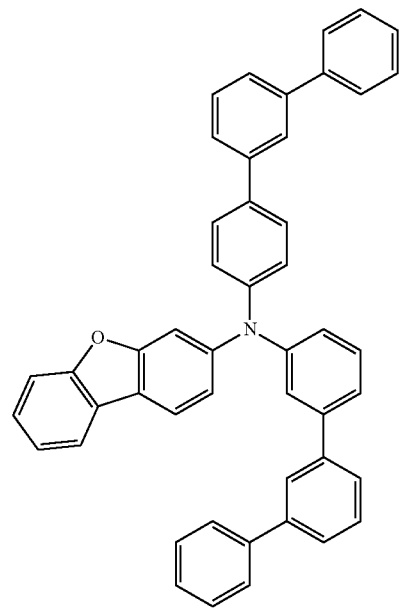
21
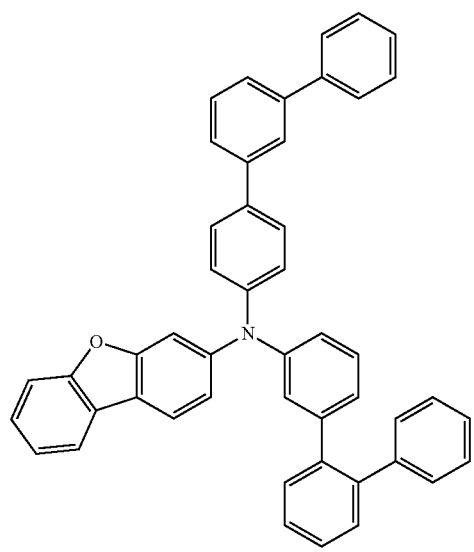
22
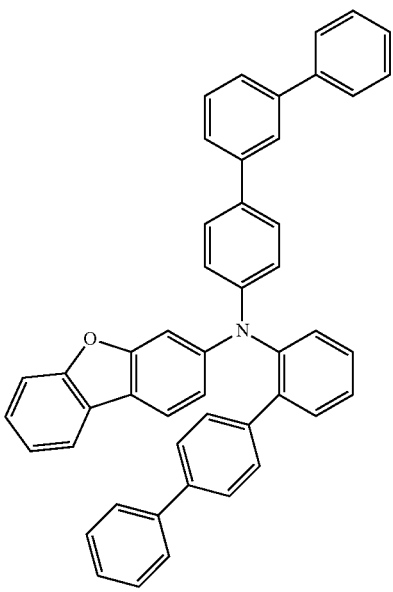
23
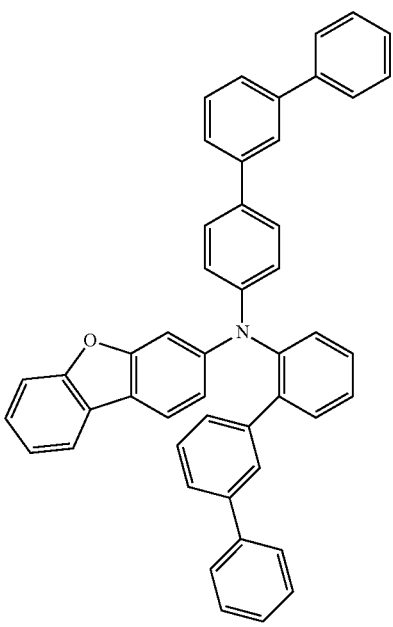

24
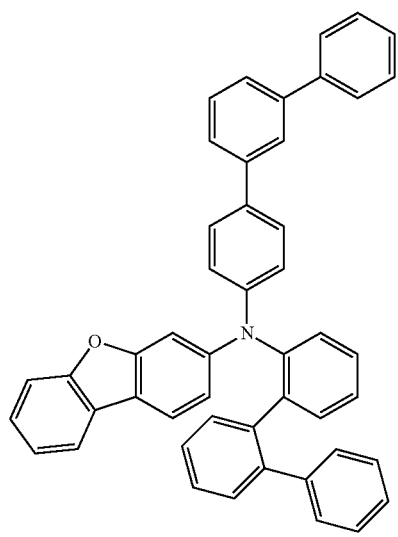
The amine derivative according to an embodiment of the inventive concept may include at least one of compounds 25 to 33 below.
25
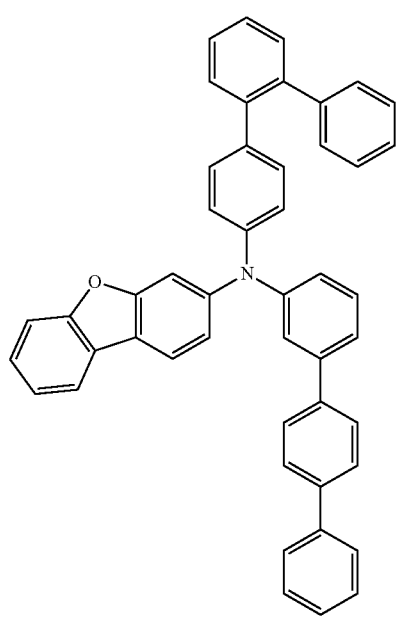
26
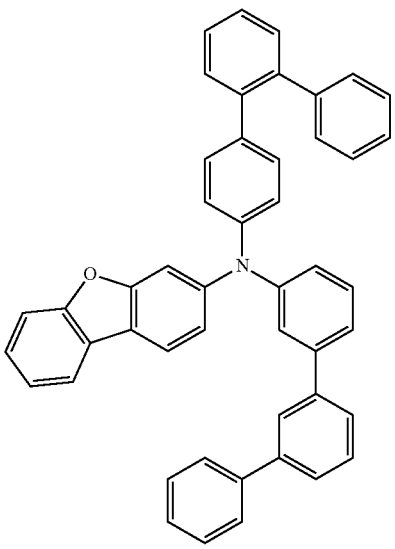
27
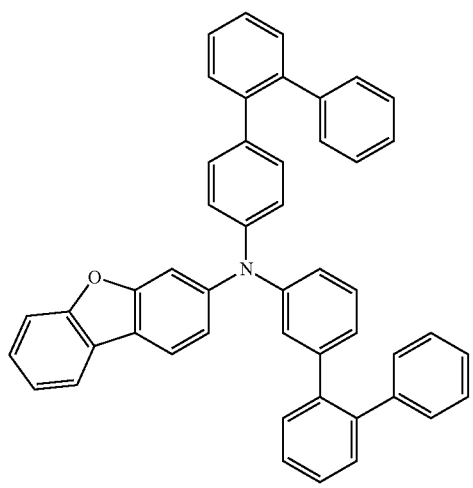
28
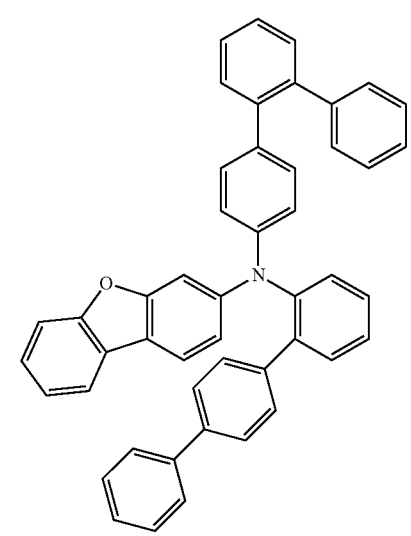

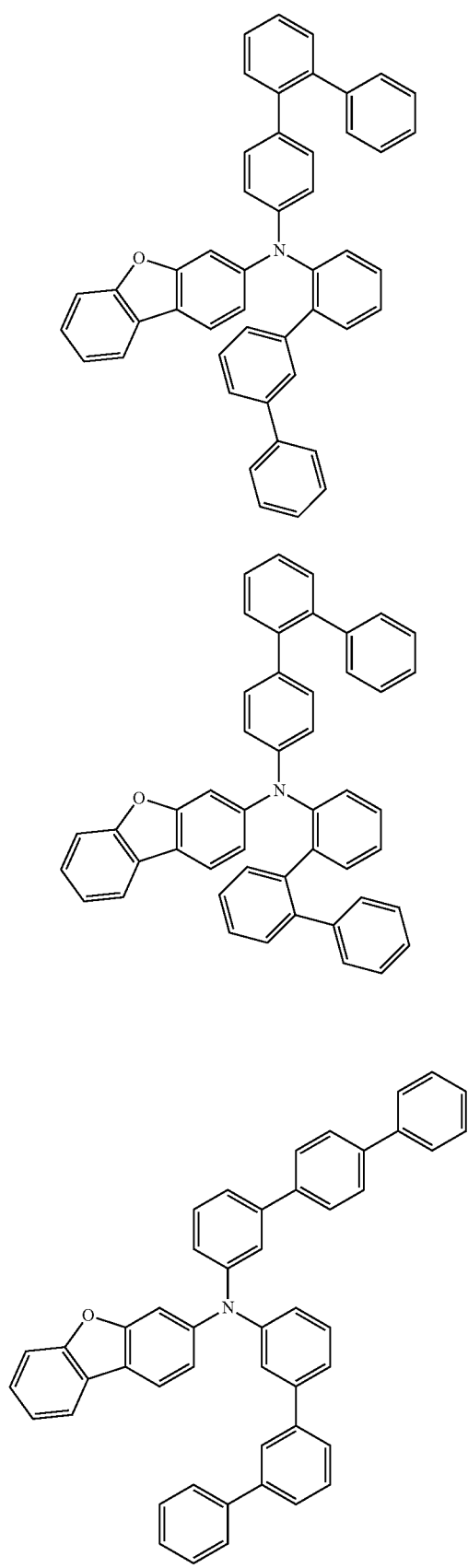
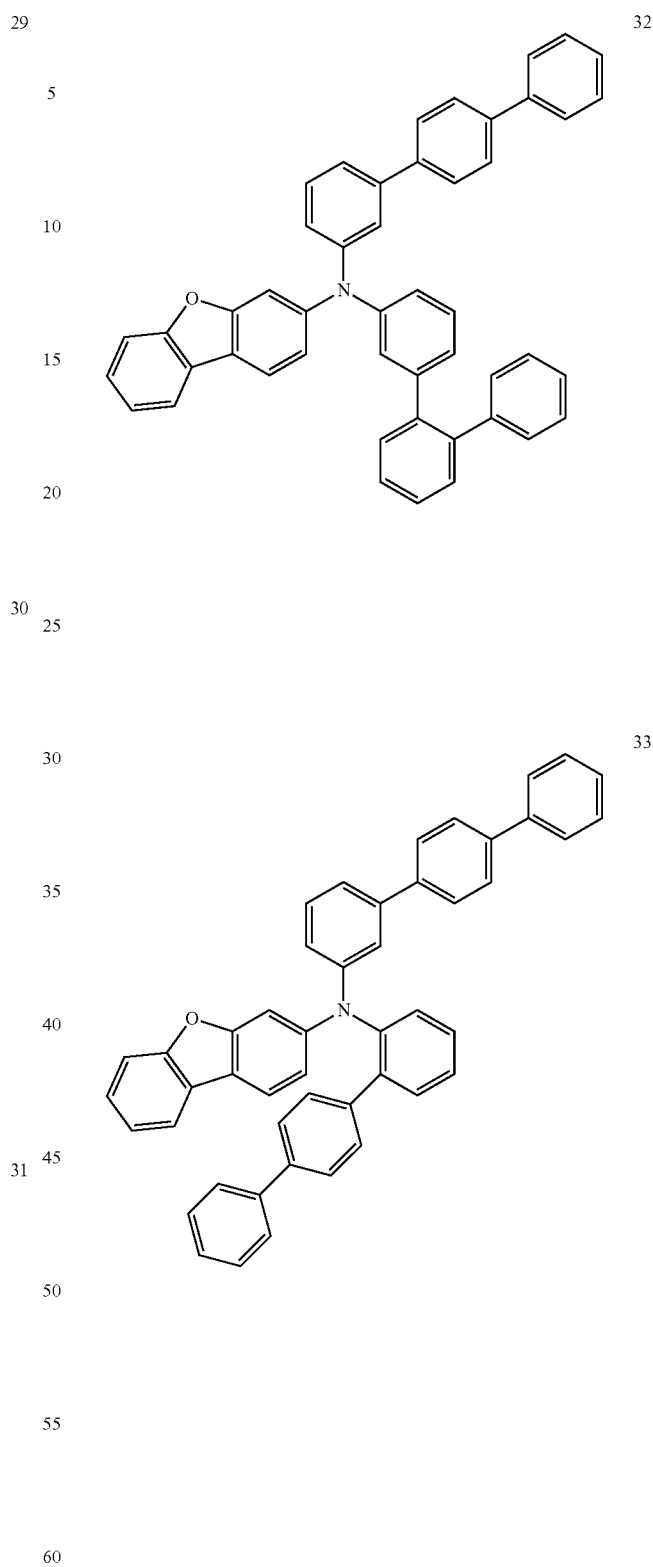
The amine derivative according to an embodiment of the inventive concept may include at least one of compounds 34 to 43 below.

34
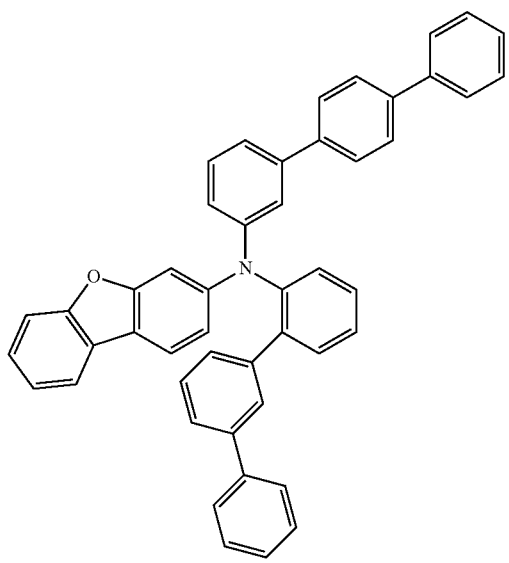
35
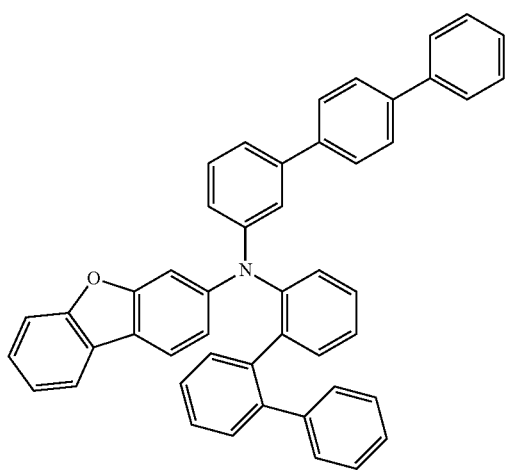
36
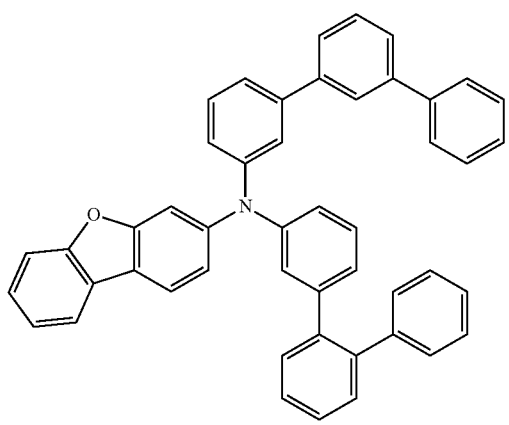
-continued
38
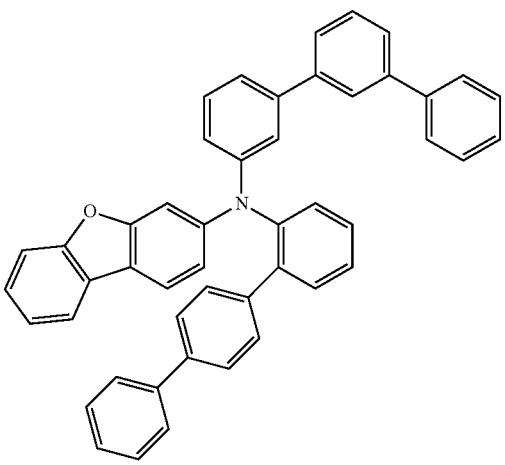
39
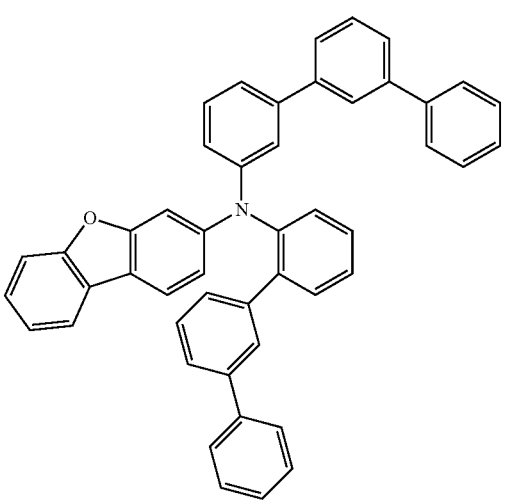
40
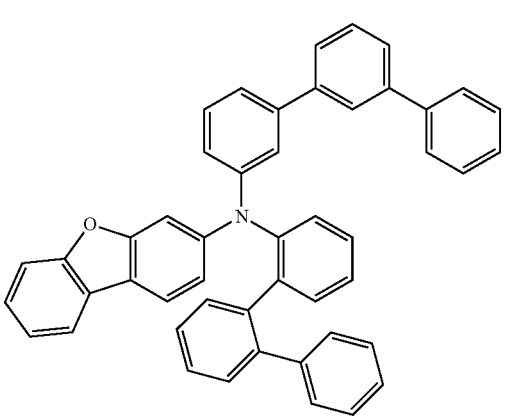

41
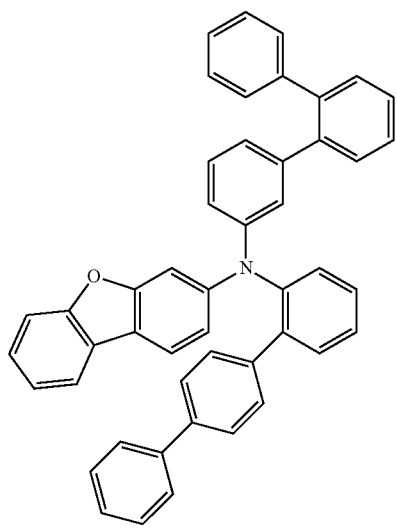
42
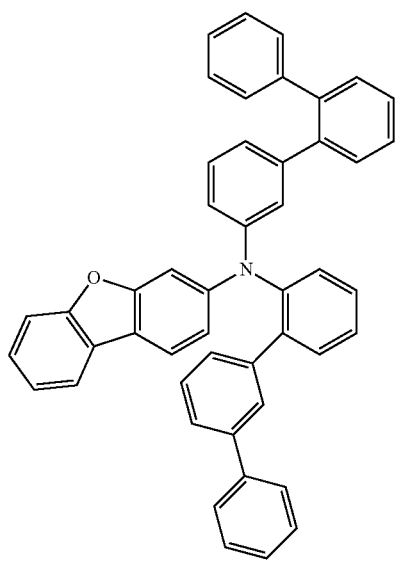
43
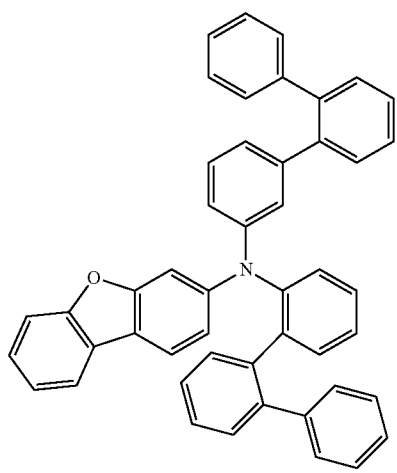
44
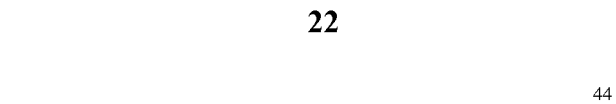
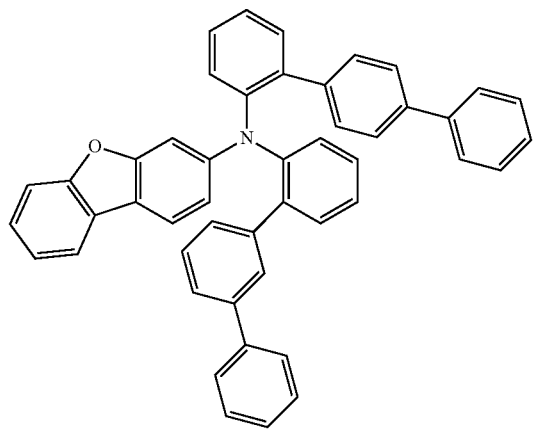
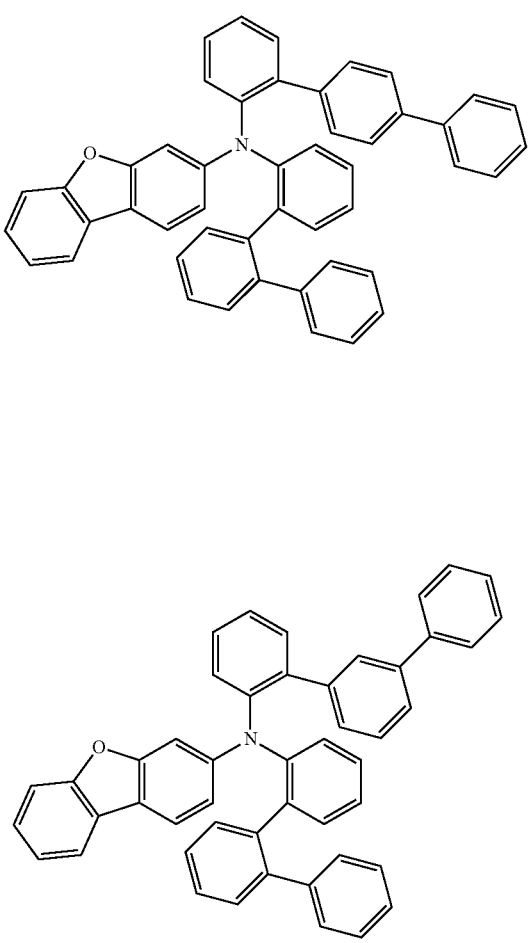
The amine derivative according to an embodiment of the inventive concept may include at least one of compounds 44 to 49 below.

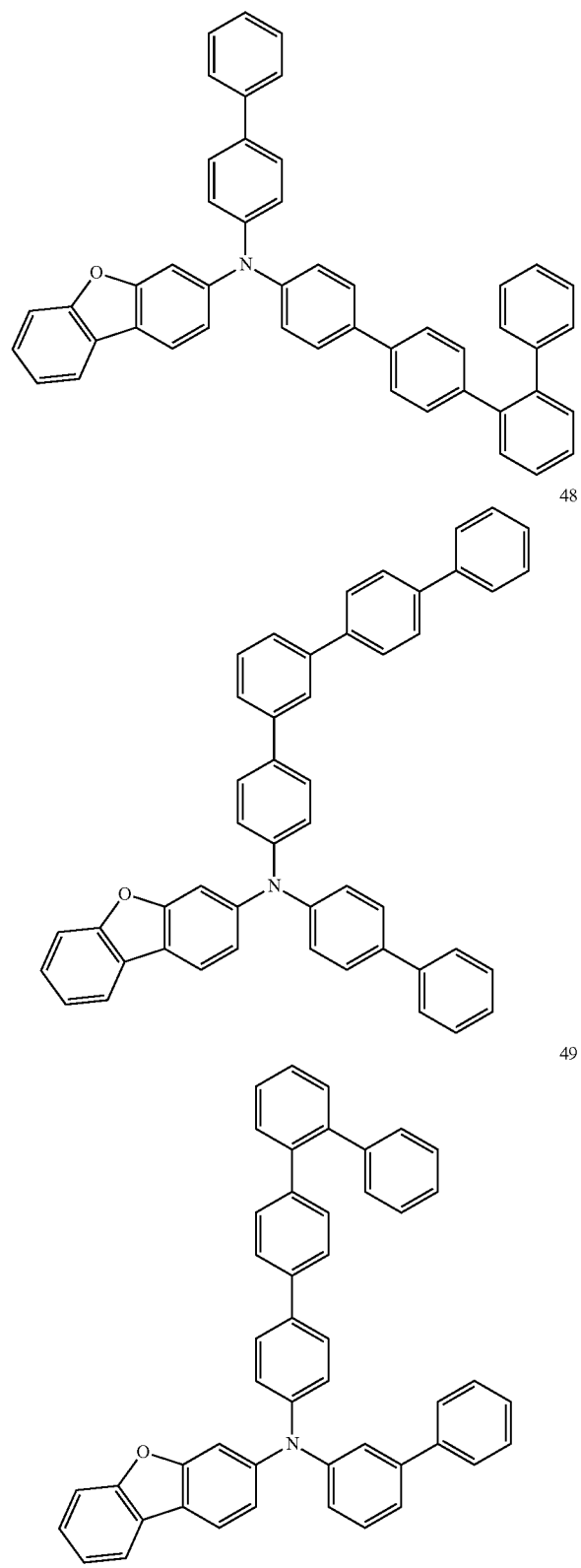
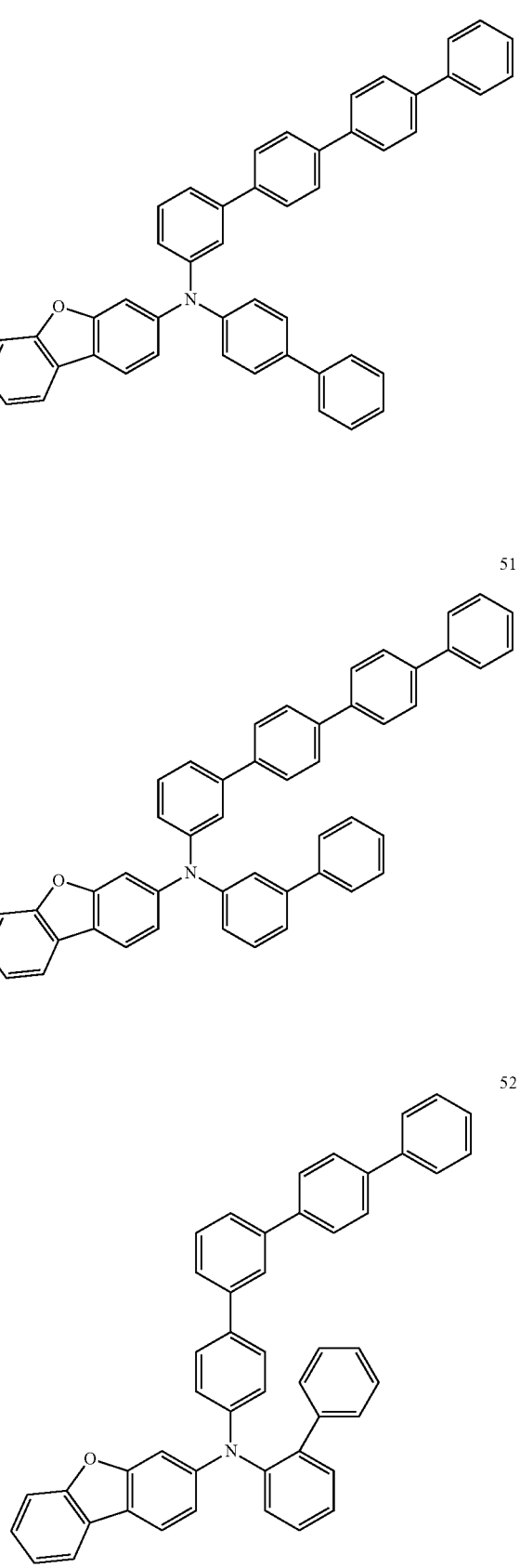
The amine derivative according to an embodiment of the inventive concept may include at least one of compounds 50 to 57 below.

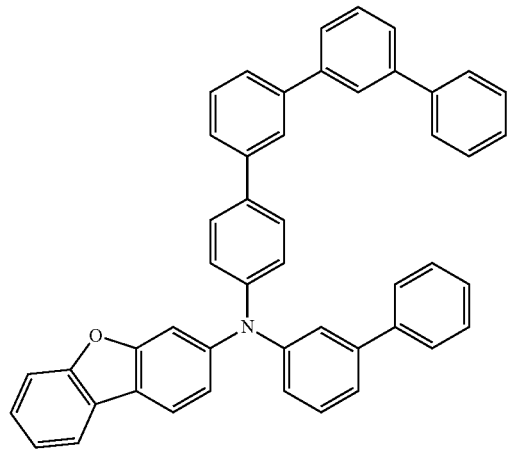
53
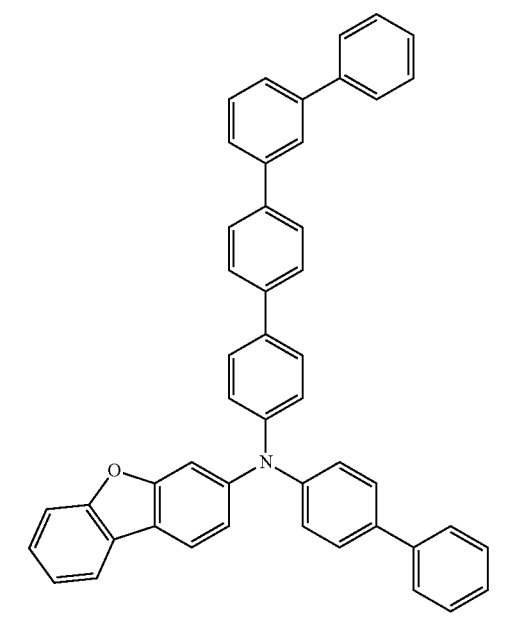
54
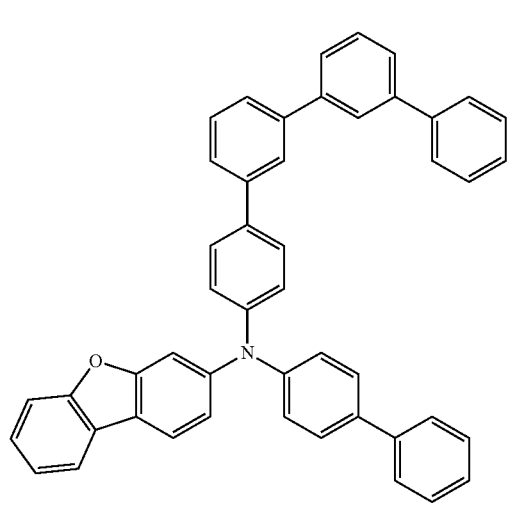
55
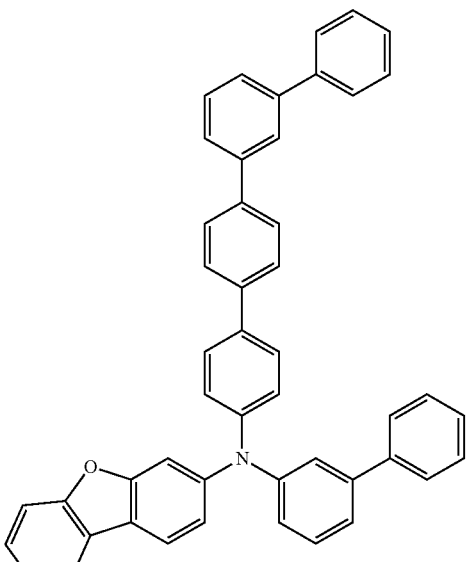
56
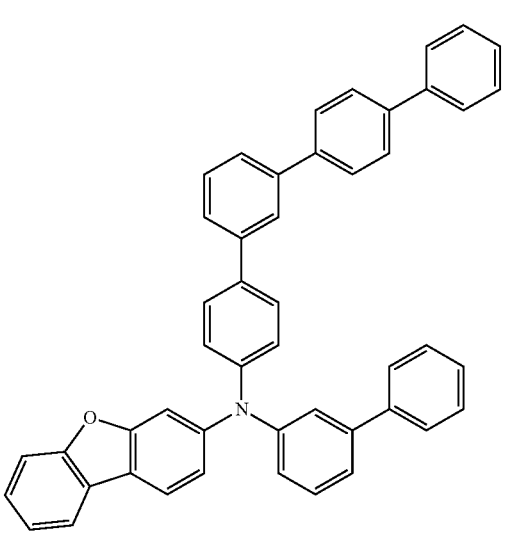
57
The amine derivative according to an embodiment of the inventive concept may include at least one of compounds 58 to 63 below.

58
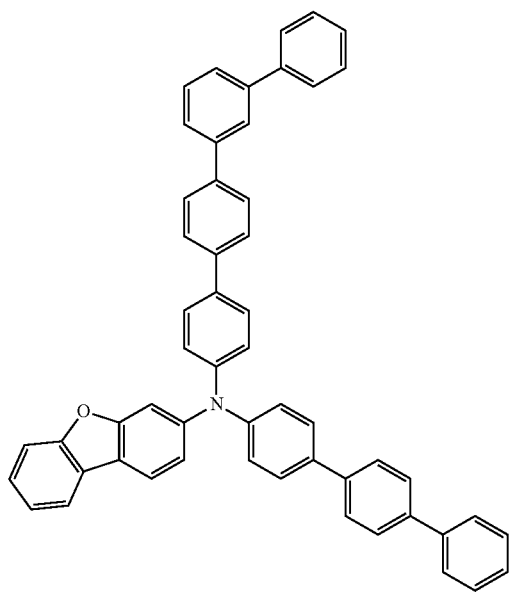
60
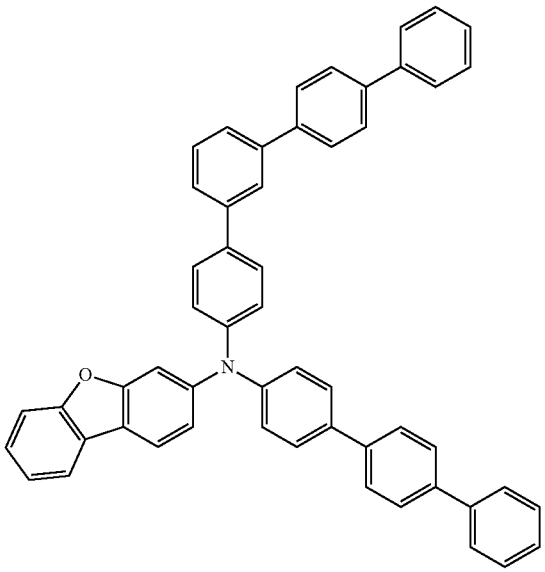
59
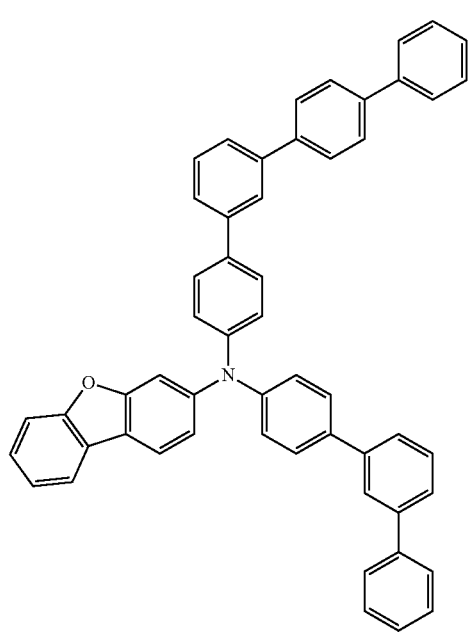
61
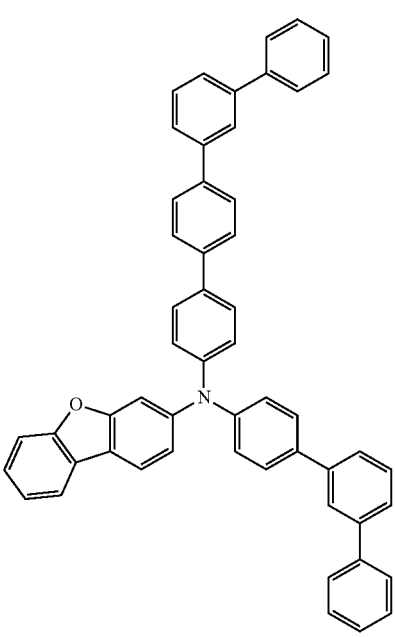

62
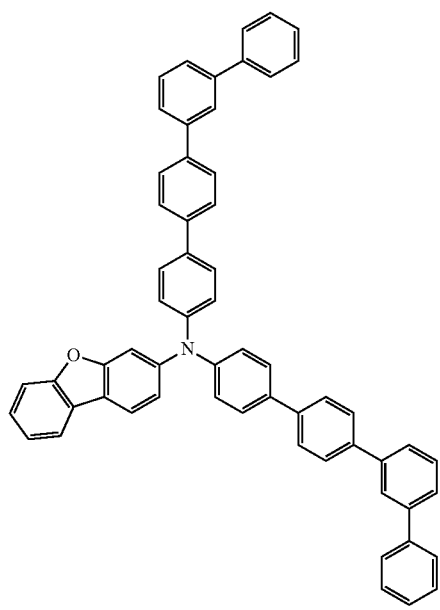
64
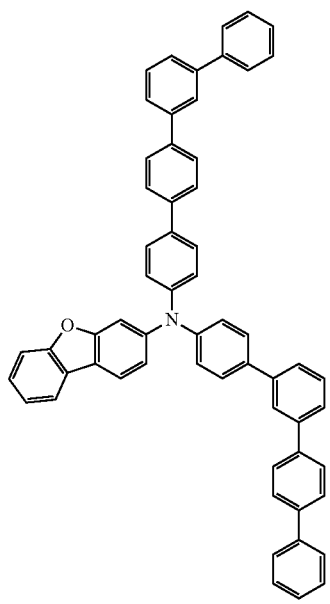
63
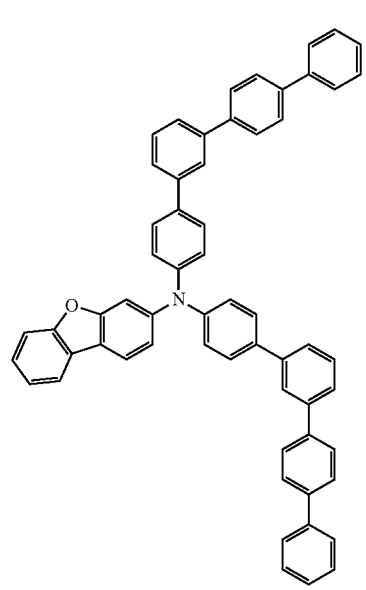
65
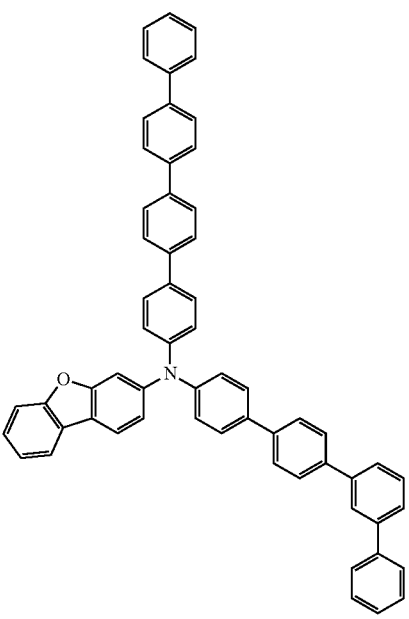
The amine derivative according to an embodiment of the inventive concept may include at least one of compounds 64 to 69 below.

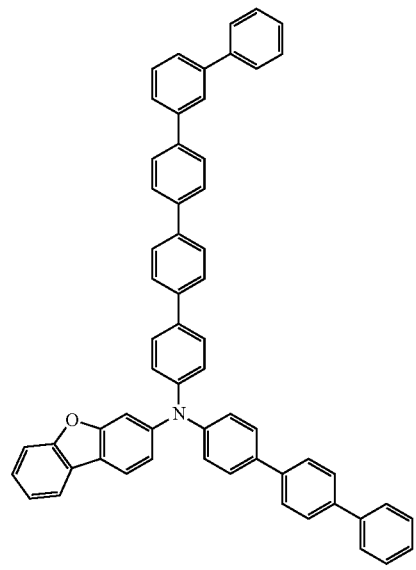
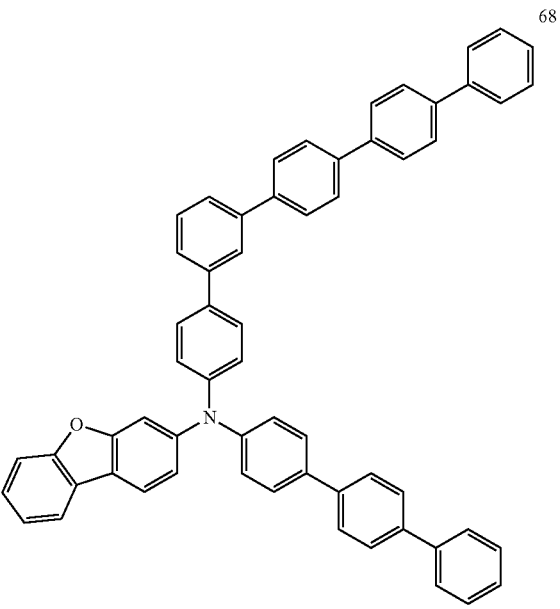
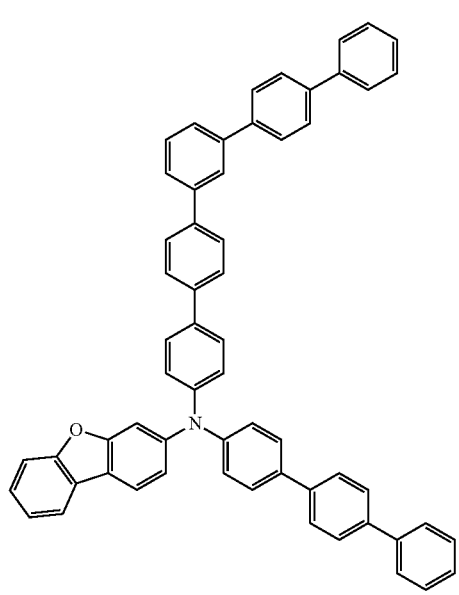
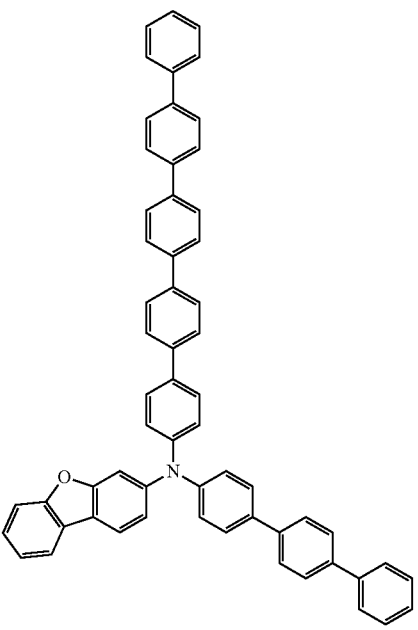
The amine derivative according to an embodiment of the inventive concept may include at least one of compounds 70 to 75 below.

70
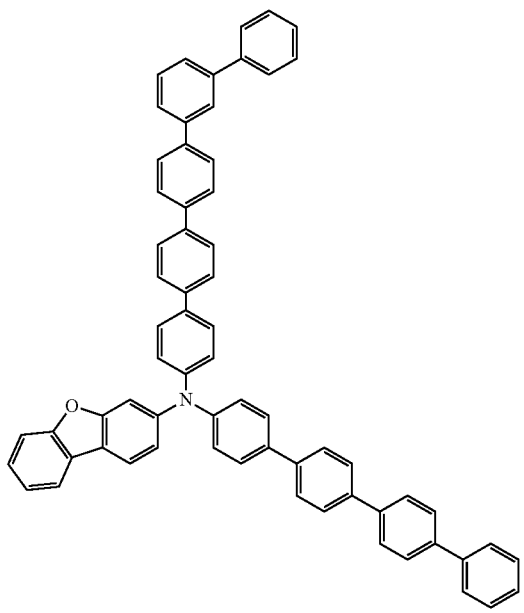
72
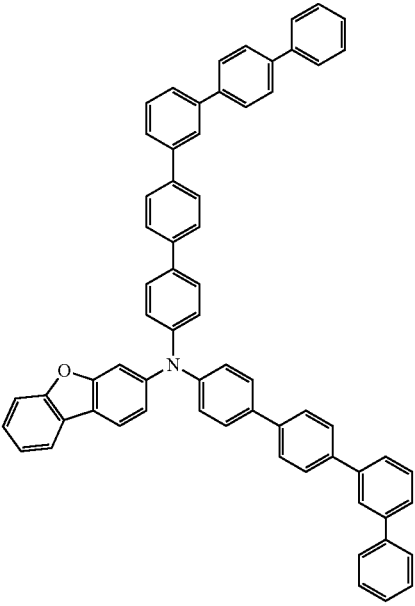
71
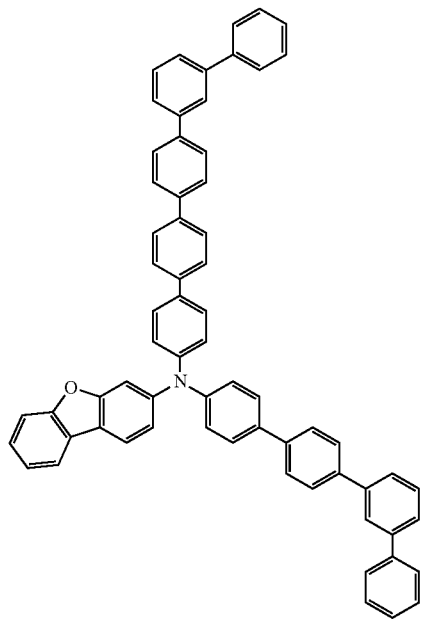
73
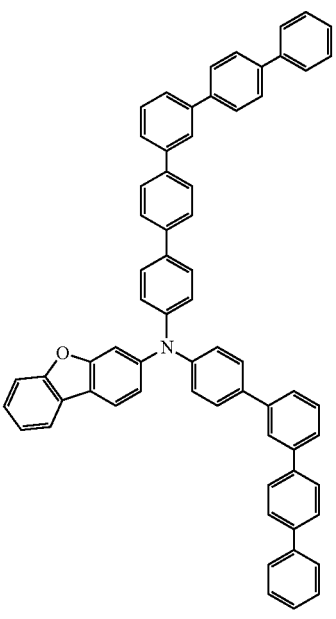

74
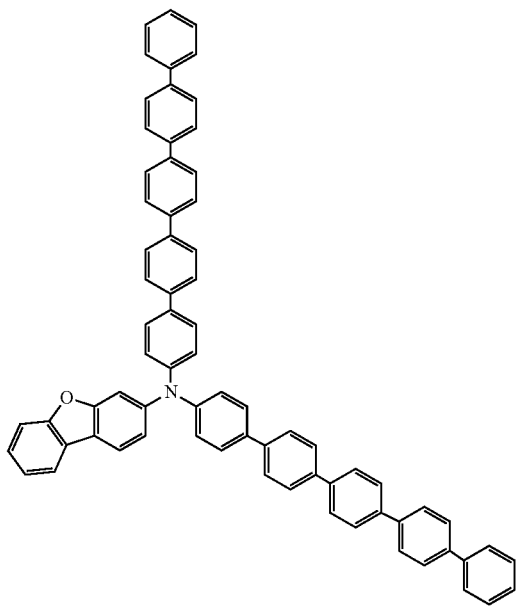
75
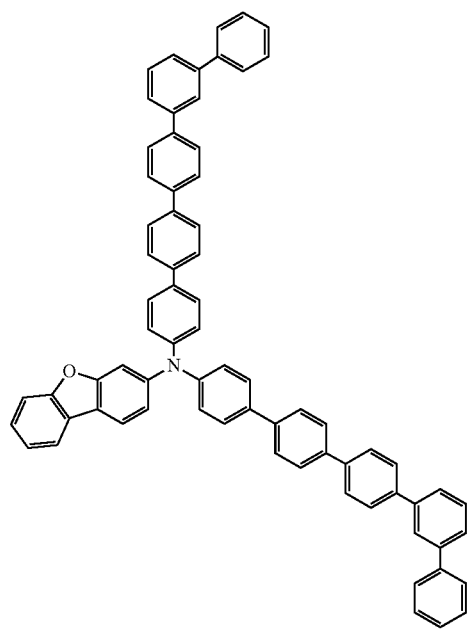
76
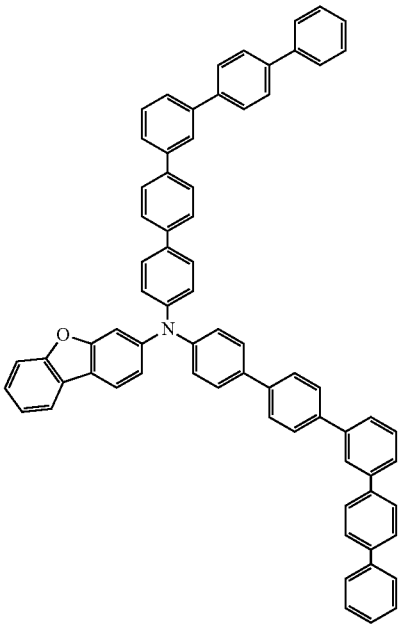
77
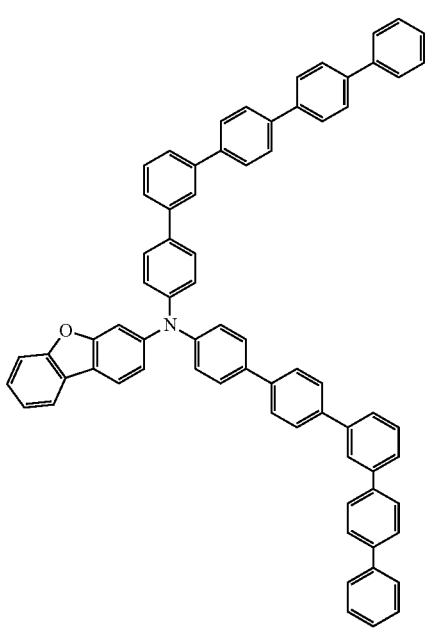
The amine derivative according to an embodiment of the inventive concept may include at least one of compounds 76 to 81 below.

-continued

78
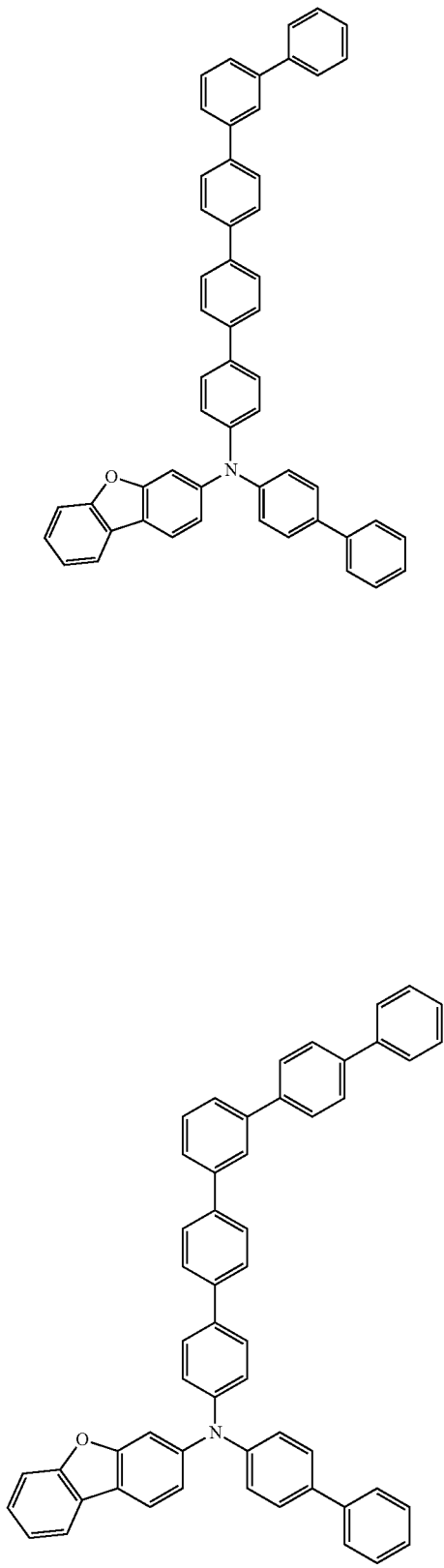

-continued

80
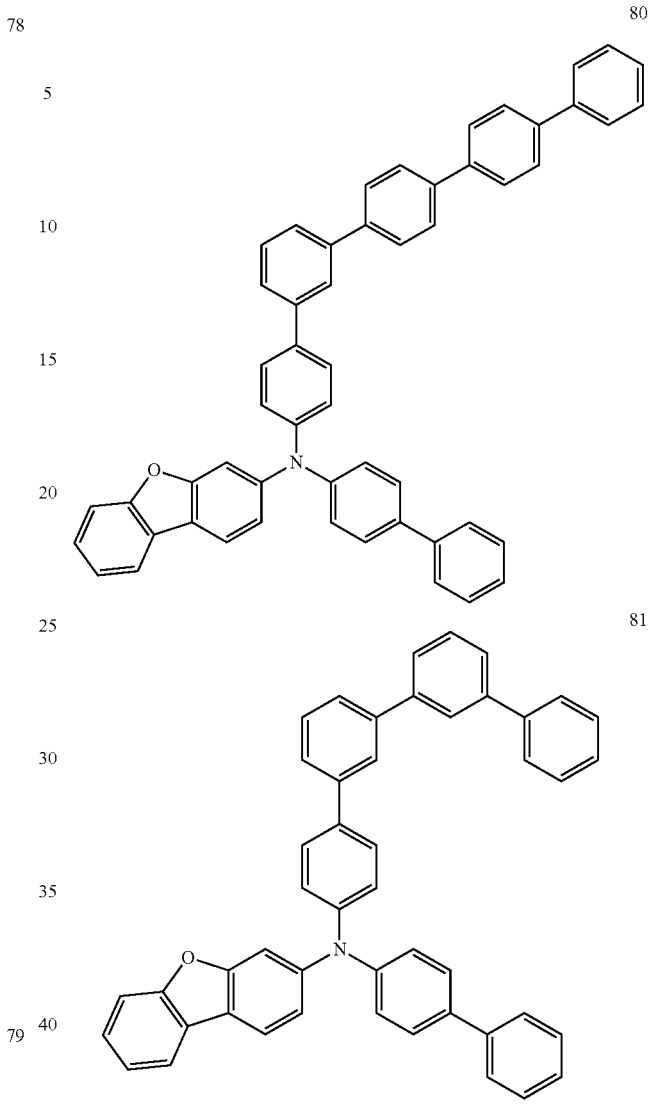

The material for an organic EL device according to an embodiment of the inventive concept may include example compounds described above, to thereby allow an organic EL device having high emission efficiency and high temperature resistance to be prepared. The material for an organic EL device according to an embodiment of the inventive concept may be appropriately utilized in any one layer of a lamination membrane (e.g., a plurality of layers) disposed between an emission layer and an anode of an organic EL device. Further, the material for an organic EL device according to an embodiment of the inventive concept has broad energy gap that covers a blue region, and thus may be applied to green to red regions.

(Organic Electroluminescent Device)

It will be described about an organic electroluminescent (EL) device utilizing the material for an organic EL device according to an embodiment of the inventive concept. The drawing is a schematic diagram showing an organic EL device 100 according to an embodiment of an embodiment of the inventive concept. The organic EL device 100 may include, for example, a substrate 102, an anode 104, a hole injection layer 106, a hole transport layer 108, an emission layer 110, an electron transport layer 112, an electron injection layer 114, and a cathode 116. In addition, in an embodiment, the material for an organic EL device according to an embodiment of the inventive concept may be utilized in any one layer of a lamination membrane (e.g., a plurality of layers) disposed between the emission layer and the anode.

As an example, it will be explained the case where the material for an organic EL device according to an embodiment of the inventive concept is utilized in the hole transport layer 108. The substrate 102 may be a transparent glass substrate, a semiconductor substrate including silicon, a flexible substrate including a resin, etc. The anode 104 may be disposed on the substrate 102 and may be defined by (e.g., may include) indium tin oxide (ITO) or indium zinc oxide (IZO), etc. The hole injection layer 106 is disposed on the anode 104 and includes, for example, 4,4',4"-tris[2-naphthyl (phenyl)amino]triphenylamine(2-TNATA), N,N,N',N'-tetrakis(3-methylphenyl)-3,3'-dimethylbenzidine (HMTPD), etc. The hole transport layer 108 is disposed on the hole injection layer 106 and defined with (e.g., includes) the material for an organic EL device according to an embodiment of the inventive concept. In an embodiment, a thickness of the hole transport layer 108 is within a range from about 3 nm or more to about 100 nm or less.

The emission layer 110 is disposed on the hole transport layer 108, and in one embodiment, contains a condensed polycyclic aromatic derivative selected from, for example, an anthracene derivative, a pyrene derivative, a fluoranthene derivative, a chrysene derivative, a benzoanthracene derivative and a triphenylene derivative. In one embodiment, the emission layer 110 contains an anthracene derivative, and/or a pyrene derivative. An anthracene derivative utilized in the emission layer 110 may include a compound represented by the following Formula 13.

Formula 13

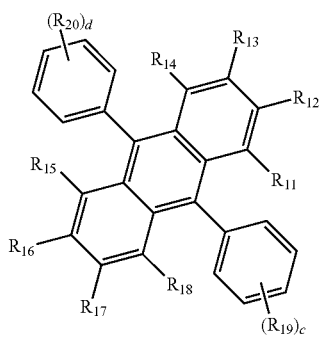

(4)

In Formula 13, $R_{11}$ to $R_{20}$ is a substituted or substituted ring-forming aryl group having 6 or more to 30 or less carbon atoms, a substituted or substituted ring-forming heteroaryl group having 1 or more to 30 or less carbon atoms, an alkyl group having 1 or more to 15 or less carbon atoms, a silyl group, a halogen atom, hydrogen, or deuterium. In addition, each of c and d is independently an integer from 0 or more to 5 or less. Further, adjacent plurality of $R_{11}$ to $R_{20}$ may bind to form a saturated or unsaturated ring.

Examples of a substituted or unsubstituted ring-forming heteroaryl group having 1 or more to 30 or less carbon atoms utilized as $R_{11}$ to $R_{20}$ may include a benzothiazolyl group, a thiophenyl group, a thienothiophenyl group, a thienothienothiophenyl group, a benzothiophenyl group, a benzofuryl group, a dibenzothiophenyl group, a benzofuryl group, an N-aryl carbazolyl group, an N-heteroarylcarbazolyl group, an N-alkylcarbazolyl group, a phenoxazyl group, a phenothiazyl group, a pyridyl group, a pyrimidyl group, a triazile group, a quinolinyl group, a quinoxalyl group, etc., but the substituted or unsubstituted ring-forming heteroaryl group having 1 or more to 30 or less carbon atoms is not limited thereto.

In addition, examples of an alkyl group having 1 or more to 15 or less carbon atoms utilized as $R_{11}$ to $R_{20}$ may include a methyl group, an ethyl group, a propyl group, an isopropyl group, an n-butyl group, an s-butyl group, an isobutyl group, a t-butyl group, an n-pentyl group, an n-hexyl group, an n-heptyl group, an n-octyl group, a hydroxyl methyl group, a 1-hydroxy ethyl group, a 2-hydroxy ethyl group, a 2-hydroxyl isobutyl group, a 1,2-dihydroxyl ethyl group, a 1,3-dihydroxyl isopropyl group, a 2,3-dihydroxyl-t-butyl group, a 1,2,3-trihydroxyl propyl group, a chloromethyl group, a 1-chloroethyl group, a 2-chloroethyl group, a 2-chloroisobutyl group, a 1,2-dichloroethyl group, a 1,3-dichloroisopropyl group, a 2,3-dichloro-t-butyl group, a 1,2,3-trichloropropyl group, a bromomethyl group, a 1-bromoethyl group, a 2-bromoethyl group, a 2-bromoisobutyl group, a 1,2-dibromoethyl group, a 1,3-dibromoisopropyl group, a 2,3-dibromo-t-butyl group, a 1,2,3-tribromopropyl group, an iodinemethyl group, a 1-iodineethyl group, a 2-iodineethyl group, a 2-iodineisobutyl group, a 1,2-diiodineethyl group, a 1,3-diiodineisopropyl group, a 2,3-diiodine-t-butyl group, a 1,2,3-triiodinepropyl group, an aminomethyl group, a 1-aminoethyl group, a 2-aminoethyl group, a 2-aminoisobutyl group, a 1,2-diaminoethyl group, a 1,3-diaminoisopropyl group, a 2,3-diamino-t-butyl group, a 1,2,3-triaminopropyl group, a cyanomethyl group, a 1-cyanoethyl group, a 2-cyanoethyl group, a 2-cyanoisobutyl group, a 1,2-dicyanoethyl group, a 1,3-dicyanoisopropyl group, a 2,3-dicyano-t-butyl group, a 1,2,3 -tricyanopropyl group, a nitromethyl group, a 1-nitroethyl group, a 2-nitroethyl group, a 2-nitroisobutyl group, a 1,2-dinitroethyl group, a 1,3-dinitroisopropyl group, a 2,3-dinitro-t-butyl group, a 1,2,3-trinitropropyl group, a cyclopropyl group, a cyclobutyl group, a cyclopentyl group, a cyclohexyl group, 4-methyl cyclohexyl group, 1-adamantyl group, 2-adamantyl group, 1-norbornyl group, 2-norbornyl group, etc., but the alkyl group having 1 or more to 15 or less carbon atoms is not specifically limited thereto.

An anthracene derivative utilized in the emission layer 110 of the organic EL device according to an embodiment of the inventive concept may include at least one of compounds a-1 to a-6 below.

a-1

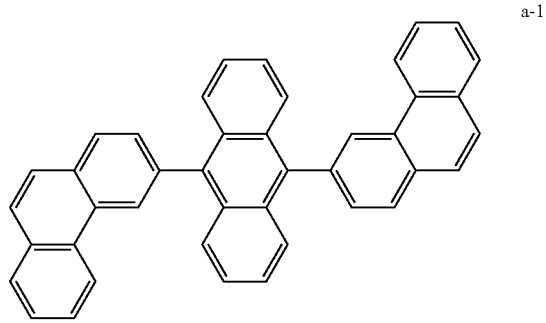

-continued
a-2
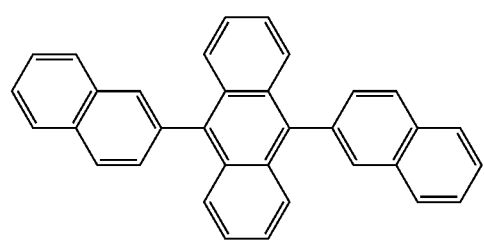
a-3
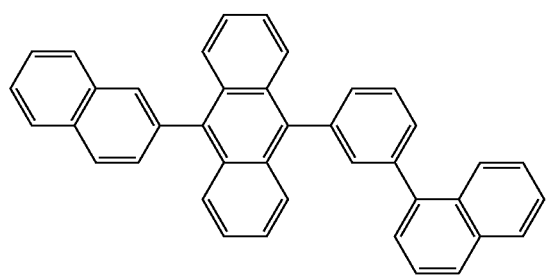
a-4
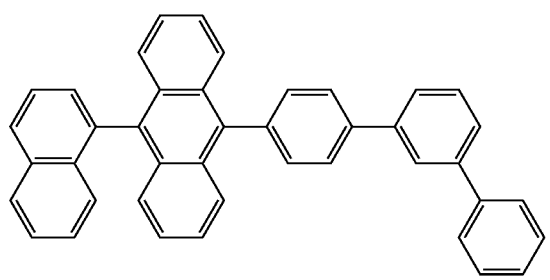
a-5
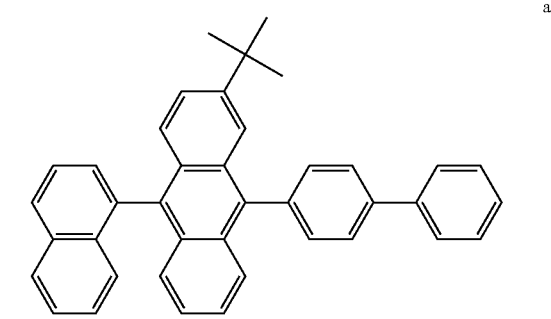
a-6
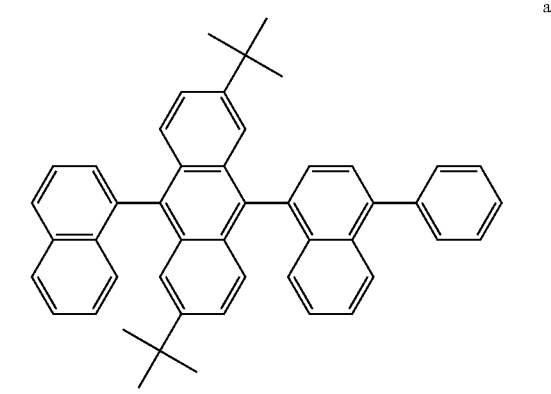
a-7
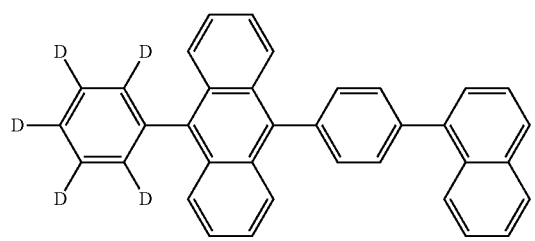
a-8
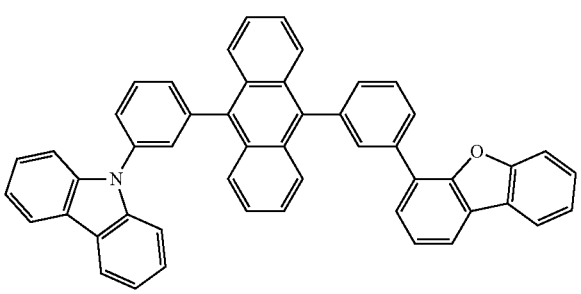
a-9
a-10
a-11
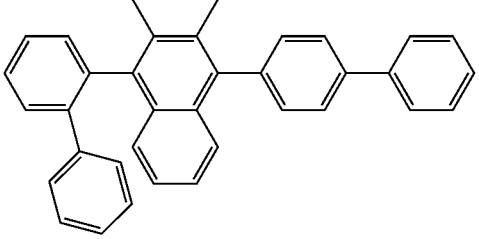
An anthracene derivative utilized in the emission layer 110 of the organic EL device according to an embodiment of the inventive concept may include at least one of compounds a-7 to a-12 below.

a-12

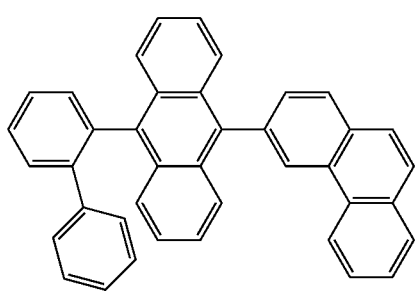

The emission layer 110, for example, may include a dopant such as 2,5,8,11-tetra-t-butylperrylene (TBP), a styryl derivative (for example, 1,4-bis[2-(3-N-ethylcarbazoryl)vinyl]benzene (BCzVB), 4-(di-p-tolylamino)-4'-[(di-p-tolylamino)styryl]stilbene (DPAVB), or N-(4-((E)-2-(6-((E)-4-(diphenylamino)styryl)naphthalen-2-yl)vinyl)phenyl)-N-phenylbenzenamine (N-BDAVBi)), phenylene and/or a derivative thereof (for example, 2,5,8,11-tetra-t-butylperylene (TBPe)), pyrene and/or a derivative thereof (for example, 1,1-dipyrene, 1,4-dipyrenylbenzene, or 1,4-Bis(N,N-Diphenylamino)pyrene), but embodiment of the inventive concept is not specifically limited thereto.

The electron transport layer 112 disposed on the emission layer 110 is defined by (e.g., may include) a material including, for example, tris(8-hydroxyquinolinato)aluminum (Alq3) or a material having a nitrogen-containing aromatic ring (for example, a material including a pyridine ring such as 1,3,5-tri[(3-pyridyl)-phen-3-yl]benzene, a material including a triazine ring such as 2,4,6-tris(3'-(pyridin-3-yl)biphenyl-3-yl)-1,3,5-triazine, or a material including an imidazole derivative such as 2-(4-(N-phenylbenzoimidazolyl-1-ylphenyl)-9,10-dinaphthylanthracene).

The electron injection layer 114 is disposed on the electron transport layer 112, and defined by (e.g., may include) a material including lithium fluoride (LiF), lithium-8-quinolinato (Liq), etc. The cathode 116 is disposed on the electron injection layer 114, and defined by (e.g., may include) a metal such as aluminum (Al), silver (Ag), lithium (Li), magnesium (Mg), or calcium (Ca), and/or a transparent material (such as indium(III) tin oxide (ITO) or indium(III) zinc oxide (IZO)). The thin membrane (e.g., thin film layer) may be formed by selecting an appropriate membrane-forming method such as vacuum metalizing, sputter, or various suitable coating methods depending on a material to be deposited.

In the organic EL device 100 according to an embodiment, by utilizing the material for an organic EL device according to an embodiment of the inventive concept as described above, a hole transport layer having high emission efficiency and high temperature resistance is provided. In addition, the material for an organic EL device according to an embodiment of the inventive concept may also be utilized in an organic EL emitter of an active matrix utilizing TFT.

Further, in the organic EL device 100 according to an embodiment, the material for an organic EL device according to an embodiment of the inventive concept described above may be utilized in any one layer of a lamination membrane (e.g., a plurality of layers) disposed between the emission layer and the anode to realize high emission efficiency and high temperature resistance of the EL device.

EXAMPLE (Preparation Method)
The material for an organic electroluminescent (EL) device according to an embodiment of the inventive concept may be synthesized, for example, as follows.

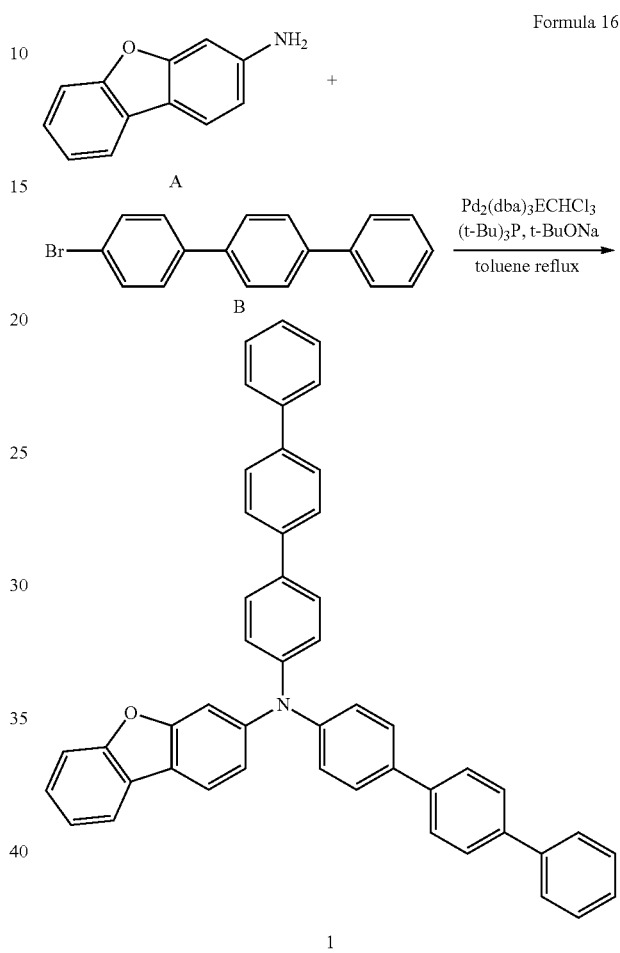

Formula 16

(Synthesis of Compound of Formula 16)
Under argon atmosphere, to a 3-necked flask of 300 mL, 3.01 g of Compound A, 12.10 g of Compound B, 1.19 g of bis(dibenzylideneacetone)palladium(0)(Pd(dba)$_2$), 1.72 mL of 2 M tri-tert-butylphosphine((t-Bu)$_3$P) in toluene solution, and 6.30 g of sodium tert-butoxide were added followed by heating and refluxing for about 3 hours and 40 minutes in 105 mL of a toluene solvent. After air cooling, filtration was performed and the solvent was evaporated. A crude product thus obtained was purified with silica gel column chromatograph (utilizing a mixture solvent of dichloromethane and hexane), and then recrystallization was performed with a mixture solvent of toluene and hexane to thereby obtain 5.76 g of Compound 1 as a white solid (yield: 55%).

(Identification of Compound 1 of Formula 16)
Molecular weight of the Compound 1 measured by FAB MS measurement was about 639. In addition, a chemical shift value of Compound 1 measured by $^1$H-NMR (CDCl$_3$) measurement was $^1$H-NMR (CDCl$_3$, δ in ppm) 7.89 (dd, J=0.25 and 0.00 Hz, 1H), 7.84 (d, J=0.27, 1H), 7.67 (m, 12H), 7.59 (m, 4H), 7.43 (m, 11H), 7.29 (m, 3H), 7.21 (dd, J=0.03 and 0.01 Hz, 1H).

(Construction of Organic Electroluminescent Device)
By utilizing Example Compounds 1, 4, 10, 31, 48 and 76 described above respectively as a hole transport material, an organic electroluminescent (EL) device of Examples 1 to 6 was provided through the preparation method described above.
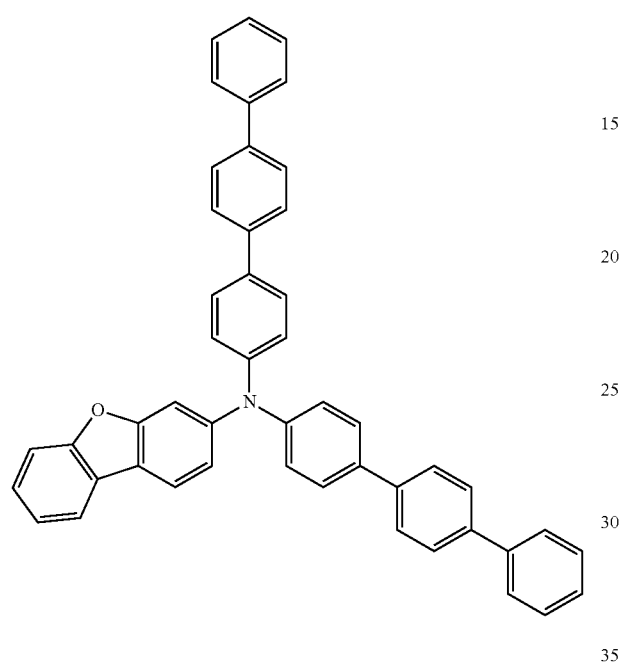
1
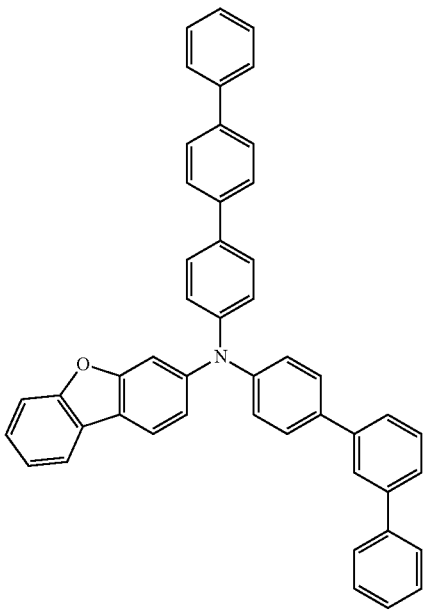
10
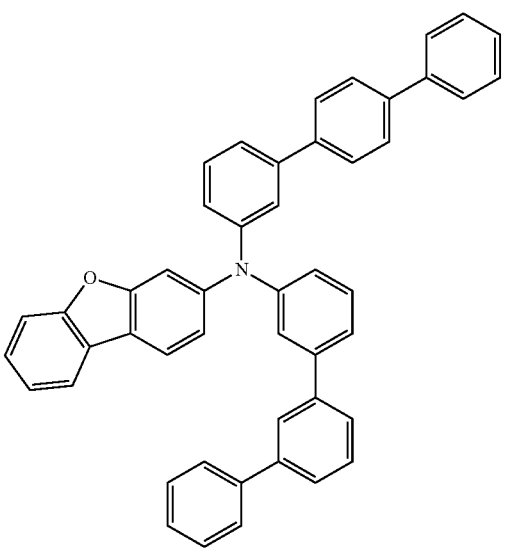
31

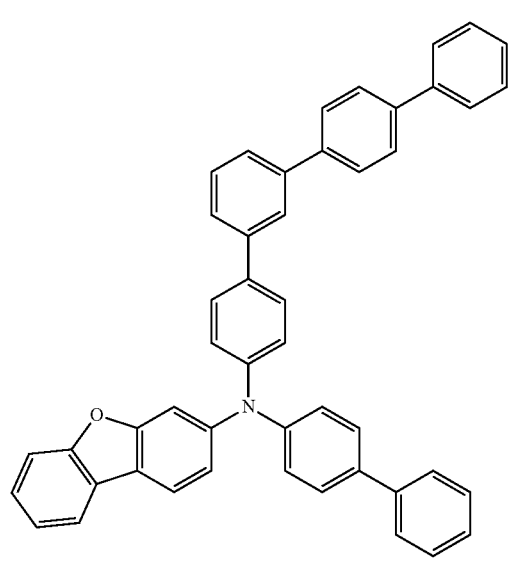
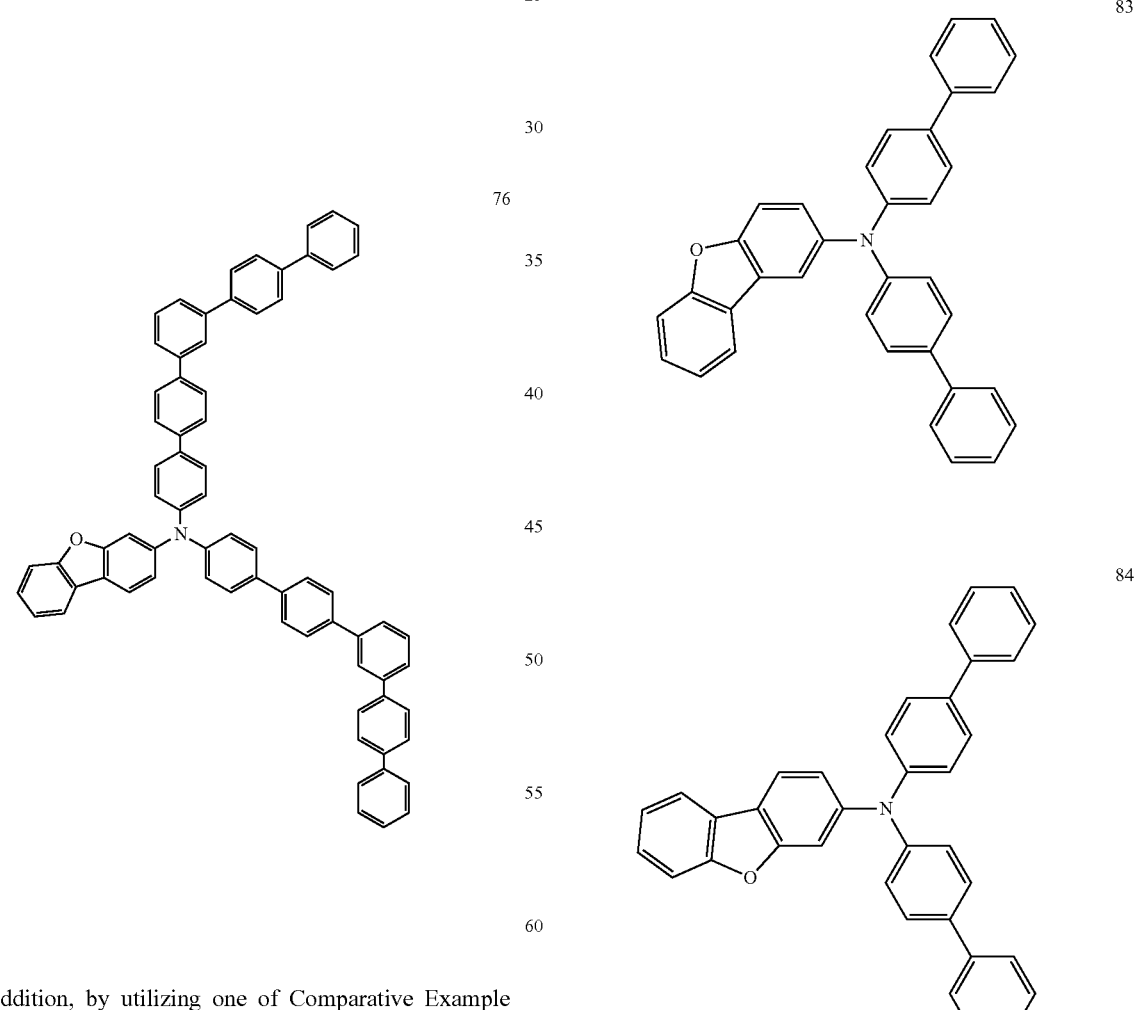
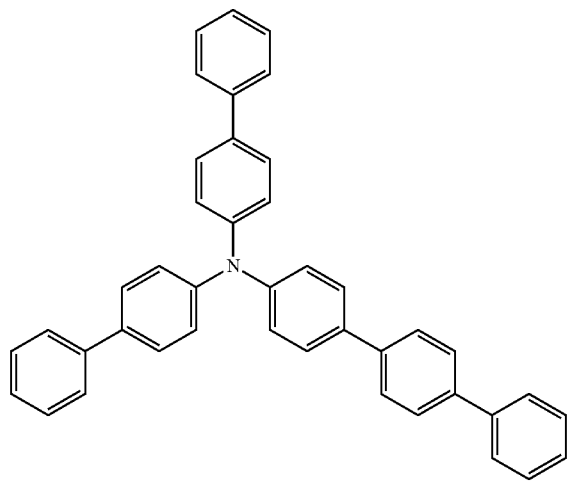
In addition, by utilizing one of Comparative Example Compounds 82 to 86 shown below, organic EL devices of Comparative Examples 1 to 5 were provided. In the examples, a transparent glass substrate was utilized as the substrate 102; an -continued

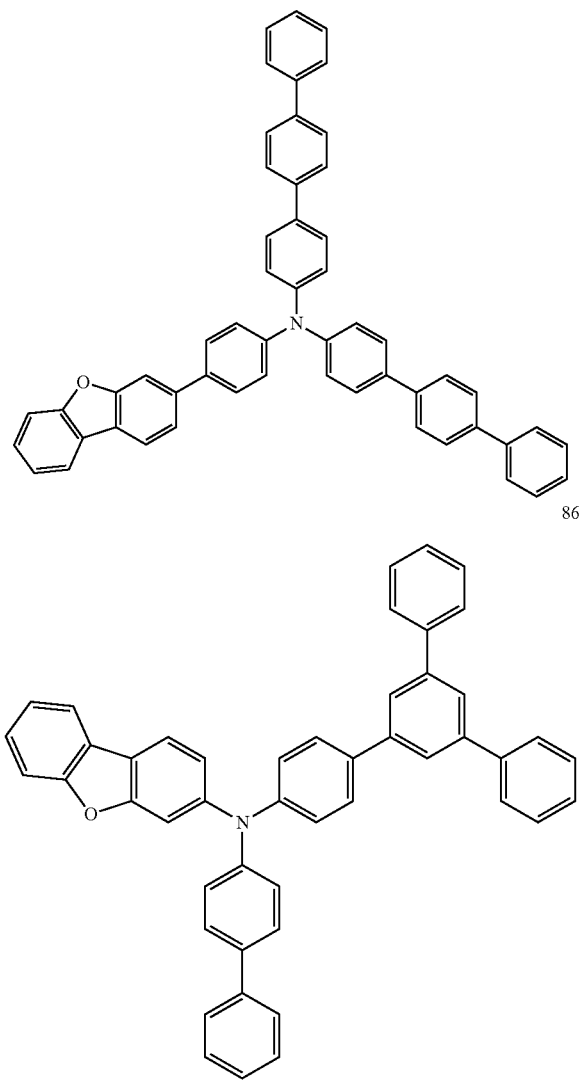

ITO having a thickness (e.g., a membrane thickness) of about 150 nm was utilized to provide the anode 104; 2-TNATA having a thickness (e.g., a membrane thickness) of about 60 nm was utilized to provide the hole injection layer 106; Compounds in Examples and Comparative Examples were utilized to provide the hole transport layer 108 having a thickness (e.g., a membrane thickness) of about 30 nm; 3% TBP-doped ADN was utilized to provide the emission layer having a thickness (e.g., a membrane thickness) of about 25 nm; Alq3 having a thickness (e.g., a membrane thickness) of about 25 nm was utilized to provide the electron transport layer 112; LiF having a thickness (e.g., a membrane thickness) of about 1 nm was utilized to provide the electron injection layer 114; and Al having a thickness (e.g., a membrane thickness) of about 100 nm was utilized to provide the cathode 116.

Emission efficiency and high temperature resistance were evaluated on the constructed organic EL devices. In addition, for evaluation of emission characteristics of the constructed organic EL devices, Brightness Light Distribution Characteristics Measurement System (HAMAMATSU Photonics, No. C9920-11) was utilized as current density was evaluated at 10 mA/cm². To evaluate high temperature resistance of the organic EL device, the constructed device was stored for about 200 hours at about 100° C., and then temperature was returned to the room temperature to carry out a performance test. O indicates that there was no change, and X indicates that change (e.g., unfavorable change) was shown. Results of evaluating the organic EL devices are shown in Table 1.

TABLE 1

| Device construction example | Hole transport layer | Current density (mA/cm²) | Emission efficiency (cd/A) | Evaluation of high temperature resistance of device |
|---|---|---|---|---|
| Example 1 | Example Compound 1 | 10 | 7.5 | O |
| Example 2 | Example Compound 4 | 10 | 7.3 | O |
| Example 3 | Example Compound 10 | 10 | 7.4 | O |
| Example 4 | Example Compound 31 | 10 | 7.3 | O |
| Example 5 | Example Compound 48 | 10 | 7.0 | O |
| Example 6 | Example Compound 76 | 10 | 6.9 | O |
| Comparative Example 1 | Comparative Example Compound 82 | 10 | 5.2 | X |
| Comparative Example 2 | Comparative Example Compound 83 | 10 | 6.0 | X |
| Comparative Example 3 | Comparative Example Compound 84 | 10 | 6.3 | X |
| Comparative Example 4 | Comparative Example Compound 85 | 10 | 6.5 | O |
| Comparative Example 5 | Comparative Example Compound 86 | 10 | 6.4 | O |

In addition, Tg [° C.] was determined for Example Compounds 1, 4, 10, 31, 48 and 76, and Comparative Example Compound 82 to 86. For measurement, DSC7020X from Hitachi High-Technologies Corporation was utilized, and DSC measurement was performed. Tg [° C.] of each compound is shown in Table 2 below.

TABLE 2

| | Tg [° C.] | | Tg [° C.] |
|---|---|---|---|
| Example Compound 1 | 115 | Comparative Example Compound 82 | 90 |
| Example Compound 4 | 105 | Comparative Example Compound 83 | 85 |
| Example Compound 10 | 108 | Comparative Example Compound 84 | 85 |
| Example Compound 31 | 100 | Comparative Example Compound 85 | 118 |
| Example Compound 48 | 125 | Comparative Example Compound 86 | 95 |
| Example Compound 76 | 140 | — | — |

Referring to Table 1, it has been apparent that Examples 1 to 6 show higher emission efficiency than Comparative Examples 1 to 5. In addition, while the organic EL devices in Examples 1 to 6 have high temperature resistance, for compounds in Comparative Examples except for the compound of Comparative Example 4, sufficient high temperature resistance may not be achieved. The compounds of the examples realize high emission efficiency and high temperature resistance by introducing 3-substituted dibenzofuran into an amine. Further, by comparing Examples 1 to 4 with Example 5, it has been apparent that higher emission efficiency and high temperature resistance may be realized by utilizing a terphenyl group instead of a biphenyl group. It would be understood that emission efficiency is greatly improved by introducing a terphenyl group into an amine to increase hole motility and to facilitate holes to flow into the emission layer. In addition, when comparing Example 1 with Example 3, it became apparent that Example 1 shows higher high temperature resistance than Example 3, where in Example 1, all arylene groups and aryl groups, which bind to an arylene group binding to a nitrogen atom, bind at the para position to the arylene group binding to the nitrogen atom (see compound 1), and, in Example 3, an aryl group is not disposed at the para position (see Compound 10).

With respect to the result of Comparative Example 2, an amine derivative having a different substation site of dibenzofuran showed unsatisfactory emission efficiency and high temperature resistance at the same time. It is considered that the result is caused by lower ability of a 2-substituted dibenzofuran derivative to block electrons than that of a 3-substituted dibenzofuran derivative, which leads to penetration of electrons from the emission layer into the hole transport layer, declination in recombine probability, and degradation of the hole transport layer.

Further, as shown in Table 2, high Tg was realized by introducing a terphenyl group in Example Compounds 1, 4, 10, 31, 48 and 76. Thus, it is considered that the heat resistance of the compounds has been enhanced. As described above, there was no issue on evaluation of high temperature resistance for the organic EL devices of Example Compound 1, 4, 10, 31, 48 and 76, while a change in performance occurred for Comparative Example Compounds 82 to 86. It has been apparent from the decreased Tg of Comparative Example Compound 84 which does not satisfy the following requirements: $n_1$ is an integer from 1 or more to 4 or less; $n_2$ is an integer from 2 or more to 4 or less; and $n_1+n_2$ is at least 4. Moreover, Tg of Comparative Example Compound 86 was decreased, wherein the Comparative Example Compound 86 has a structure having a diverged phenyl group. On the other hand, although Tg of Comparative Example Compound 85 was high, emission efficiency was declined due to the structure in which a dibenzofurnayl group is bound to a nitrogen of an amine via a phenylene group.

Taken together, it would be apparent that high emission efficiency and high temperature resistance of an organic EL device may be achieved in the blue region by introducing 3-substituted dibenzofuran and 2 terphenyl groups into an amine in the material for an organic EL device according to an embodiment of the inventive concept. In an embodiment of the inventive concept, the material for an organic EL device has broad energy gap that covers a blue region, and thus may also be applied to a green to red regions.

According to the inventive concept, an amine derivative having high emission efficiency and high temperature resistance, a material for an organic electroluminescent device and an organic electroluminescent device including the same may be provided. Particularly, according to an embodiment of the inventive concept, an amine derivative, which has high emission efficiency and high temperature resistance and is utilized in one membrane (e.g., layer) of lamination membranes (e.g., a plurality of layers) disposed between an emission layer and an anode, a material for an organic electroluminescent device and an organic electroluminescent device including the same may be provided. In an embodiment of the inventive concept, by introducing 3-substituted dibenzofuran into an amine, high emission efficiency and high temperature resistance may be realized.

As used herein, the term "substantially," "about," and similar terms are used as terms of approximation and not as terms of degree, and are intended to account for the inherent deviations in measured or calculated values that would be recognized by those of ordinary skill in the art. Also, any numerical range recited herein is intended to include all sub-ranges of the same numerical precision subsumed within the recited range. For example, a range of "1.0 to 10.0" is intended to include all subranges between (and including) the recited minimum value of 1.0 and the recited maximum value of 10.0, that is, having a minimum value equal to or greater than 1.0 and a maximum value equal to or less than 10.0, such as, for example, 2.4 to 7.6. Any maximum numerical limitation recited herein is intended to include all lower numerical limitations subsumed therein and any minimum numerical limitation recited in this specification is intended to include all higher numerical limitations subsumed therein. Accordingly, Applicant reserves the right to amend this specification, including the claims, to expressly recite any sub-range subsumed within the ranges expressly recited herein.

Expressions such as "at least one of," when preceding a list of elements, modify the entire list of elements and do not modify the individual elements of the list. Further, the use of "may" when describing embodiments of the inventive concept refers to "one or more embodiments of the inventive concept." Also, the term "exemplary" is intended to refer to an example or illustration.

The above-disclosed subject matter is to be considered illustrative and not restrictive, and the appended claims and equivalents thereof are intended to cover all such modifications, enhancements, and other embodiments, which fall within the true spirit and scope of the inventive concept. Thus, to the maximum extent allowed by law, the scope of the inventive concept is to be determined by the broadest permissible interpretation of the following claims and their equivalents, and shall not be restricted or limited by the foregoing detailed description.

53
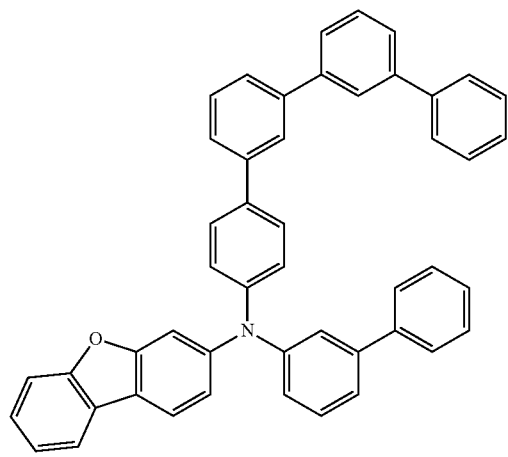
54
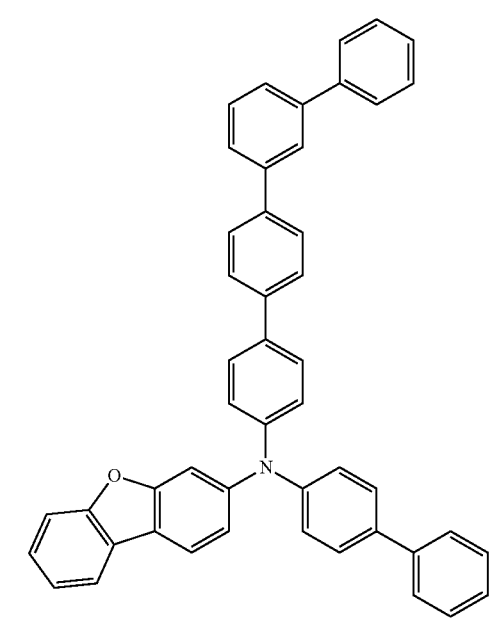
55
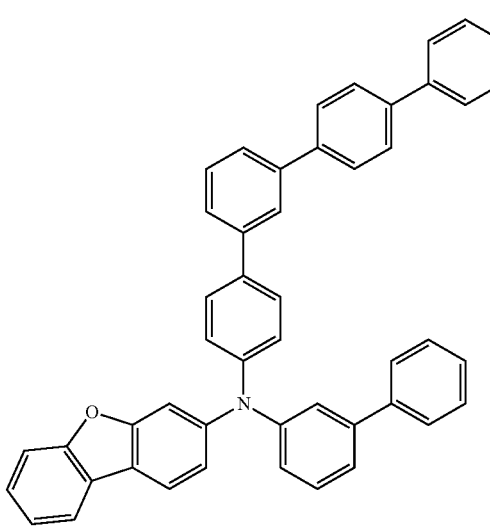
56
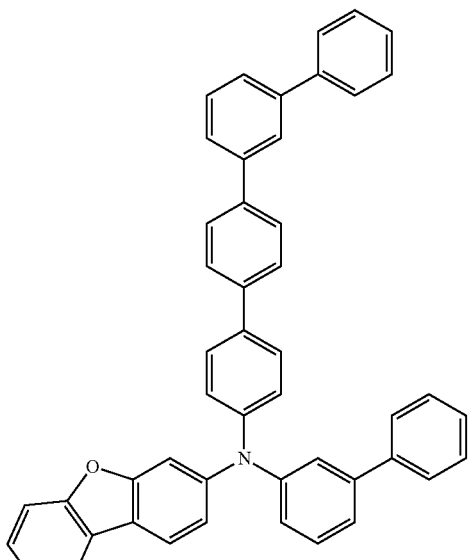
57
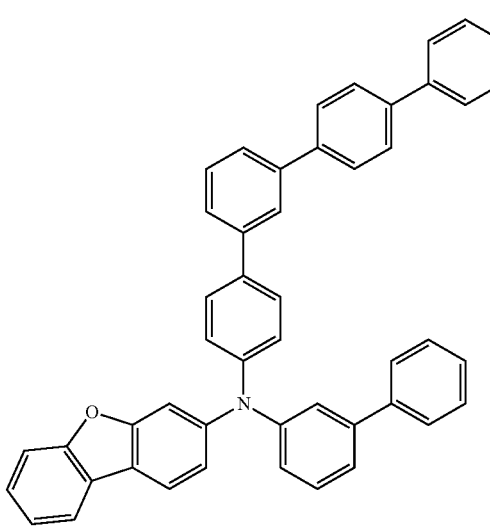

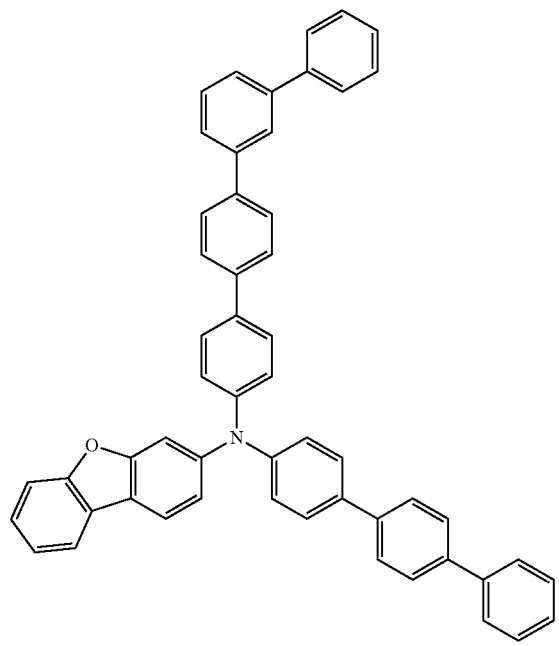
58
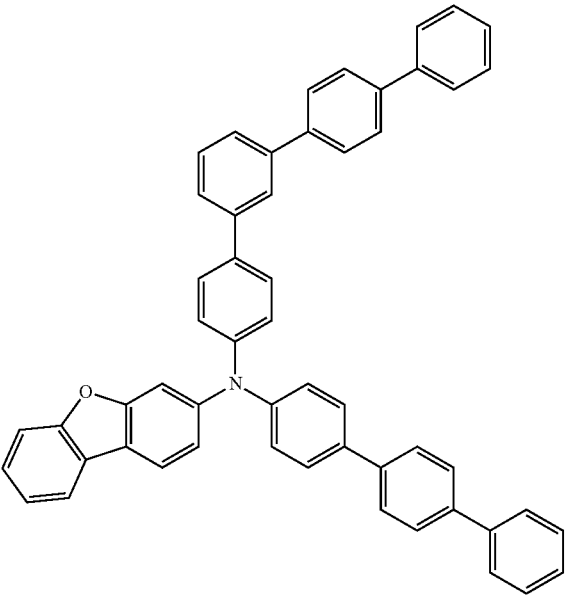
60
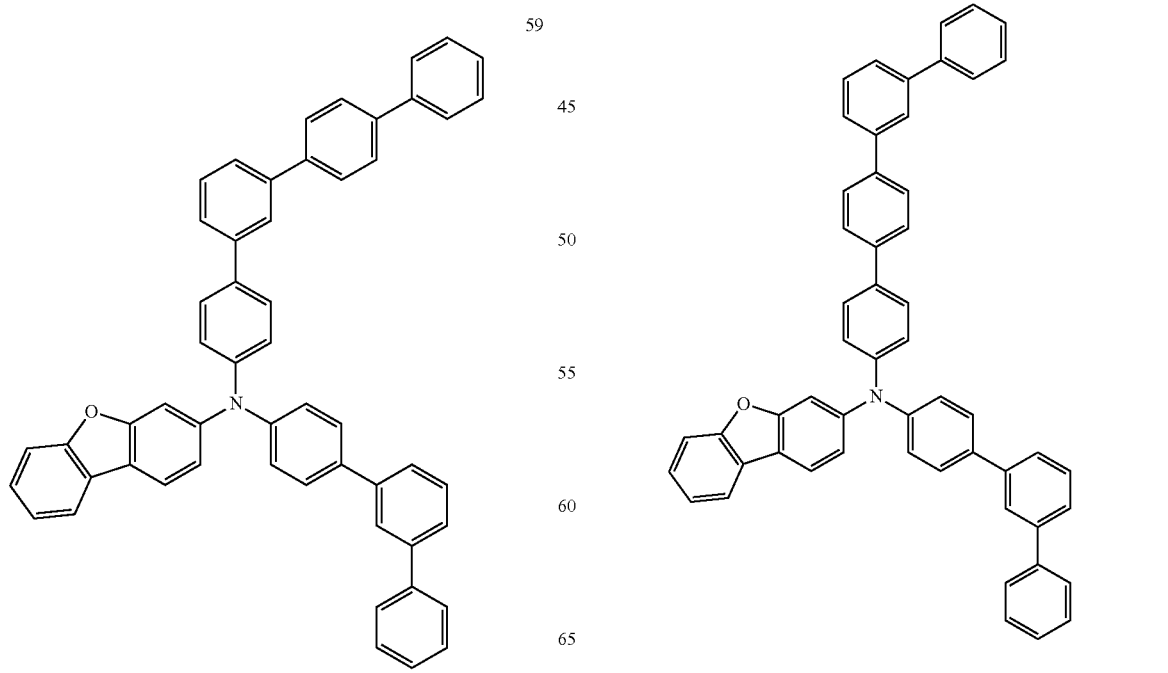

111
-continued
62
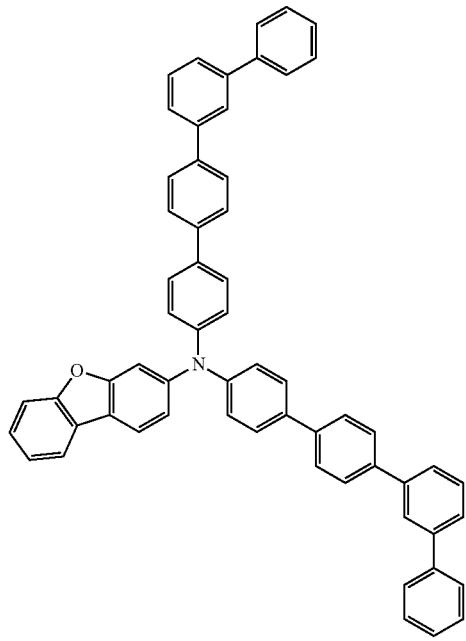
63
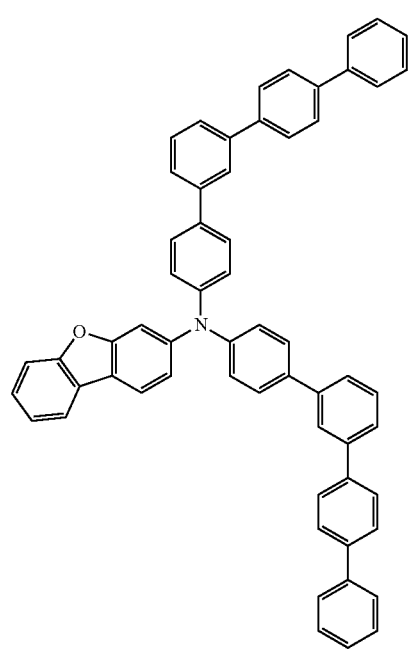
112
-continued
64
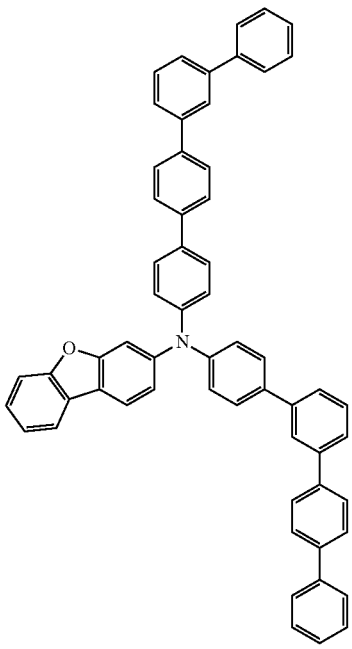
65
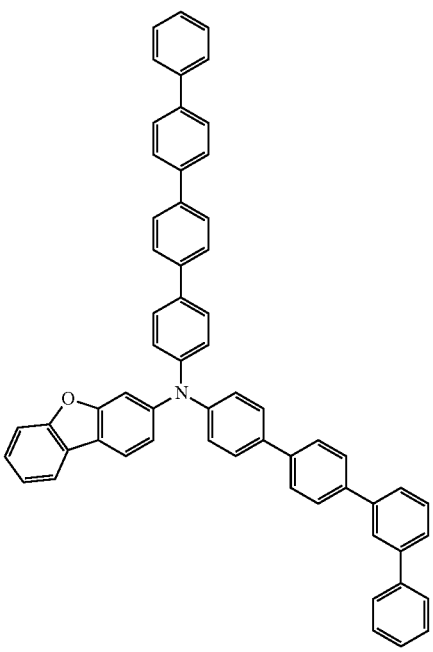

66
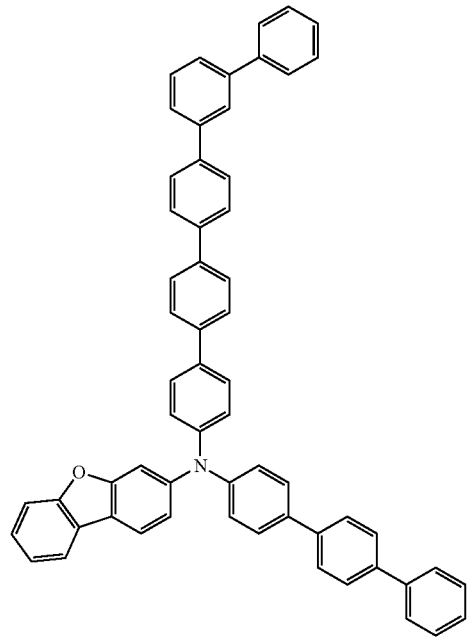
67
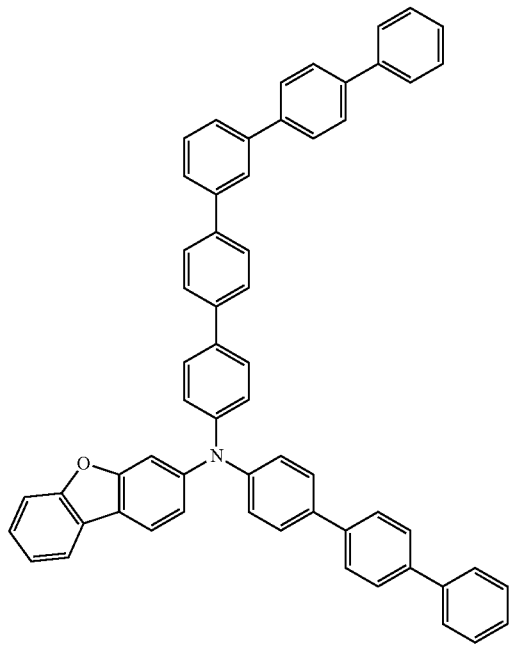
68
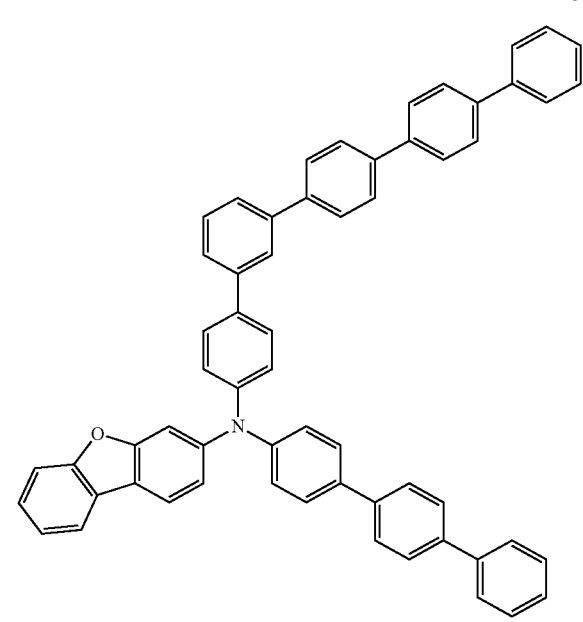
69
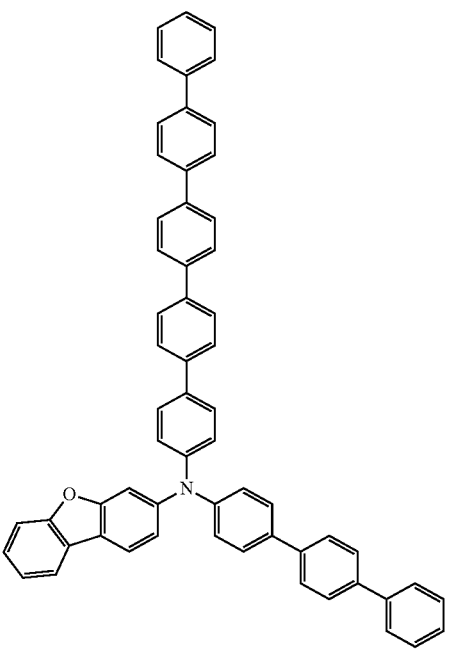

115
-continued
70
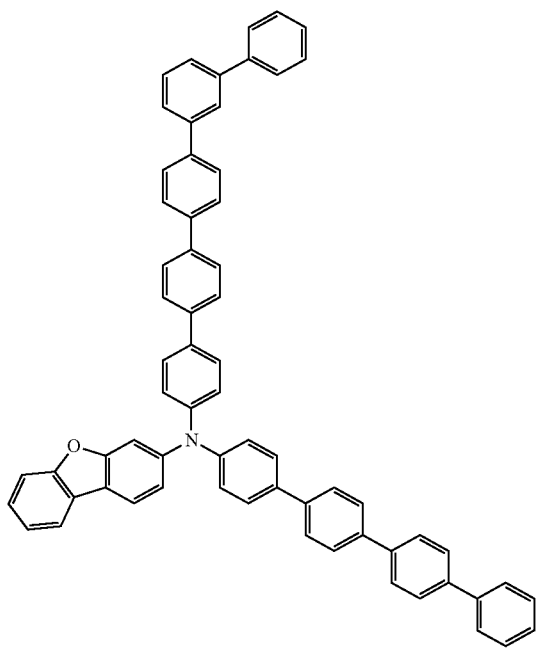
71
116
-continued
72
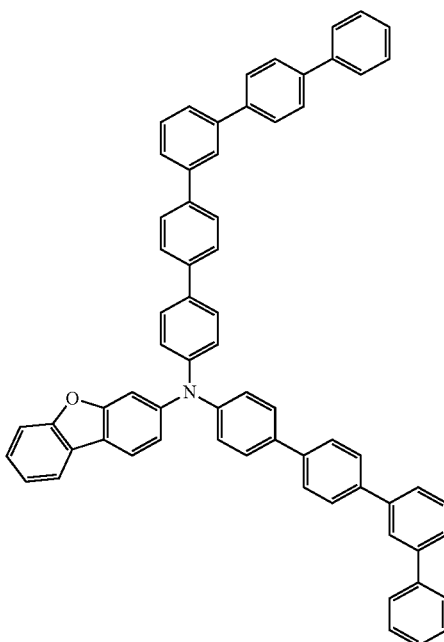
73
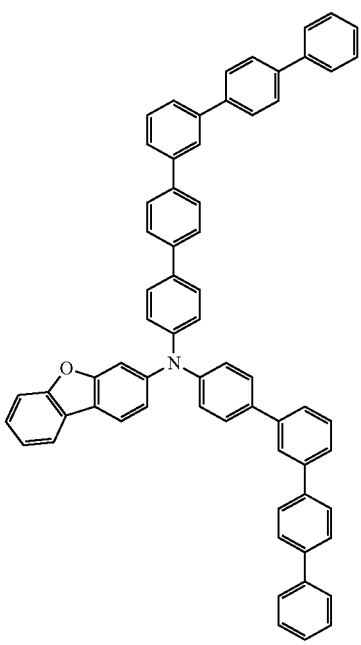
74
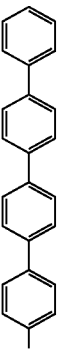

117
-continued
118
-continued
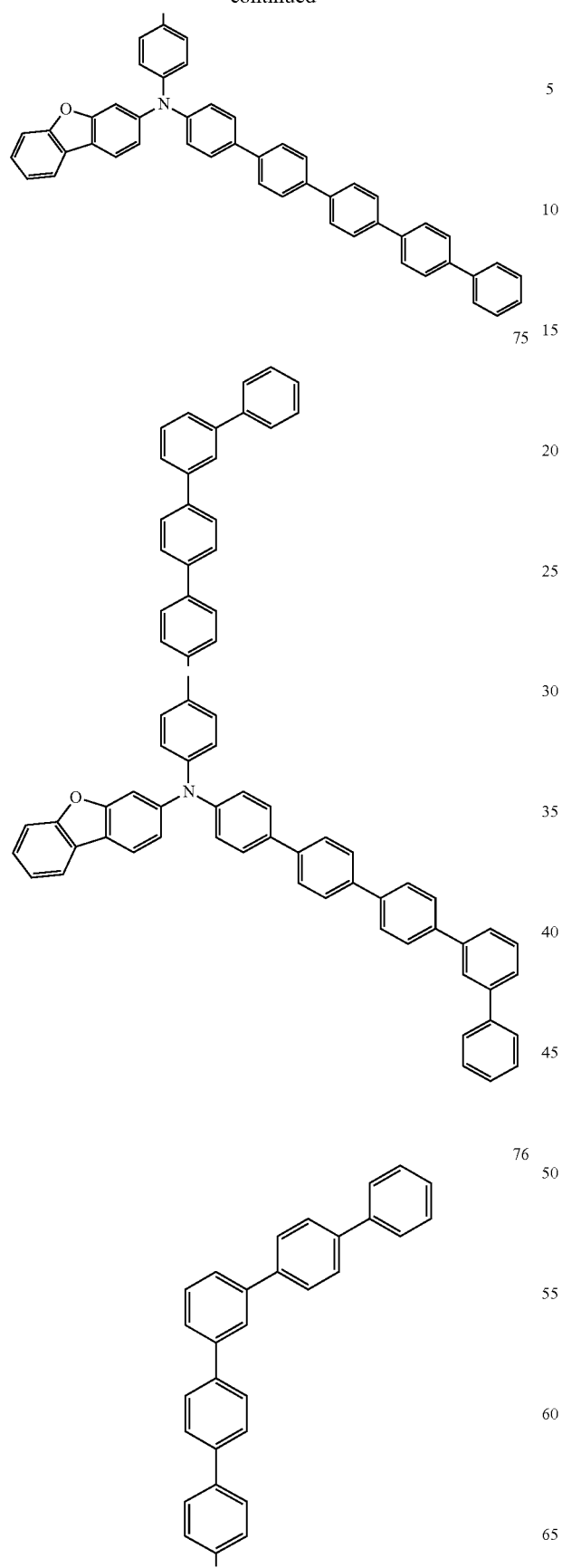
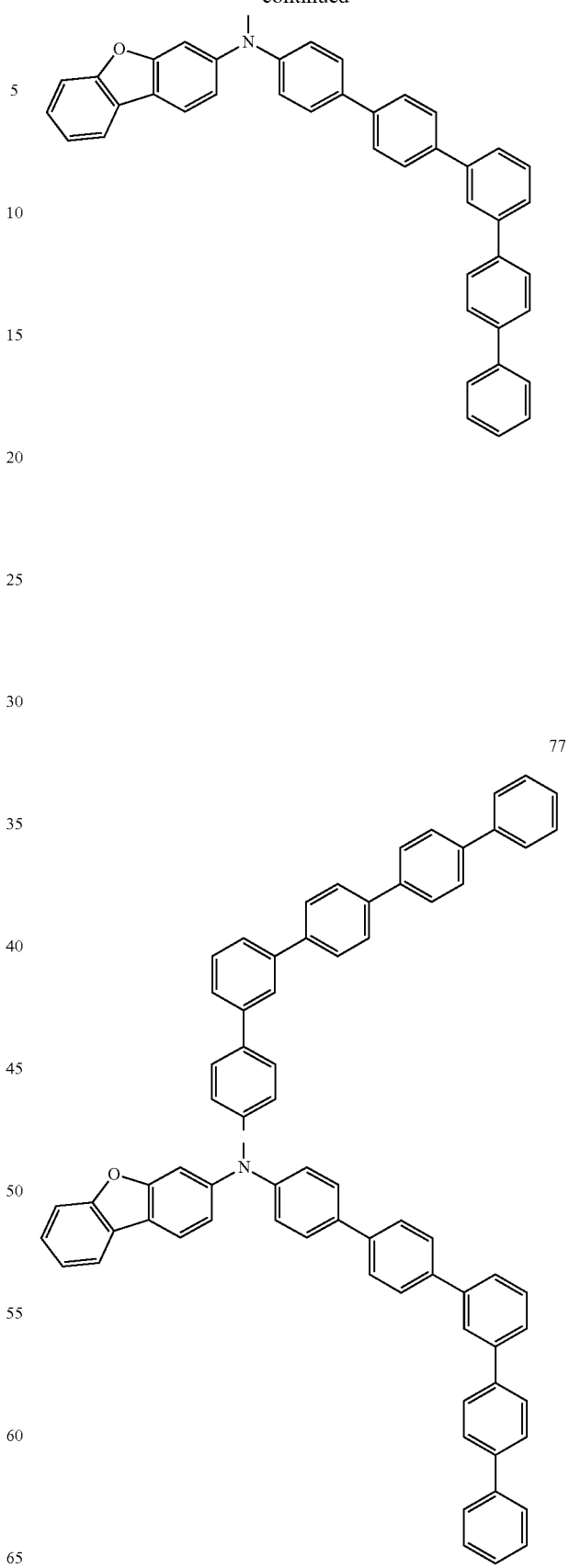

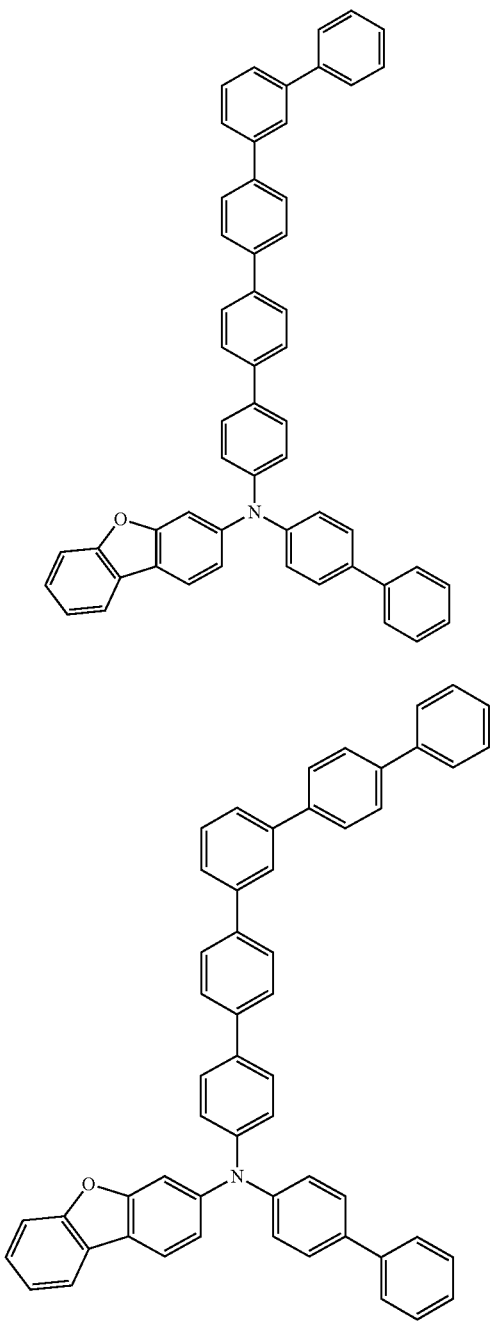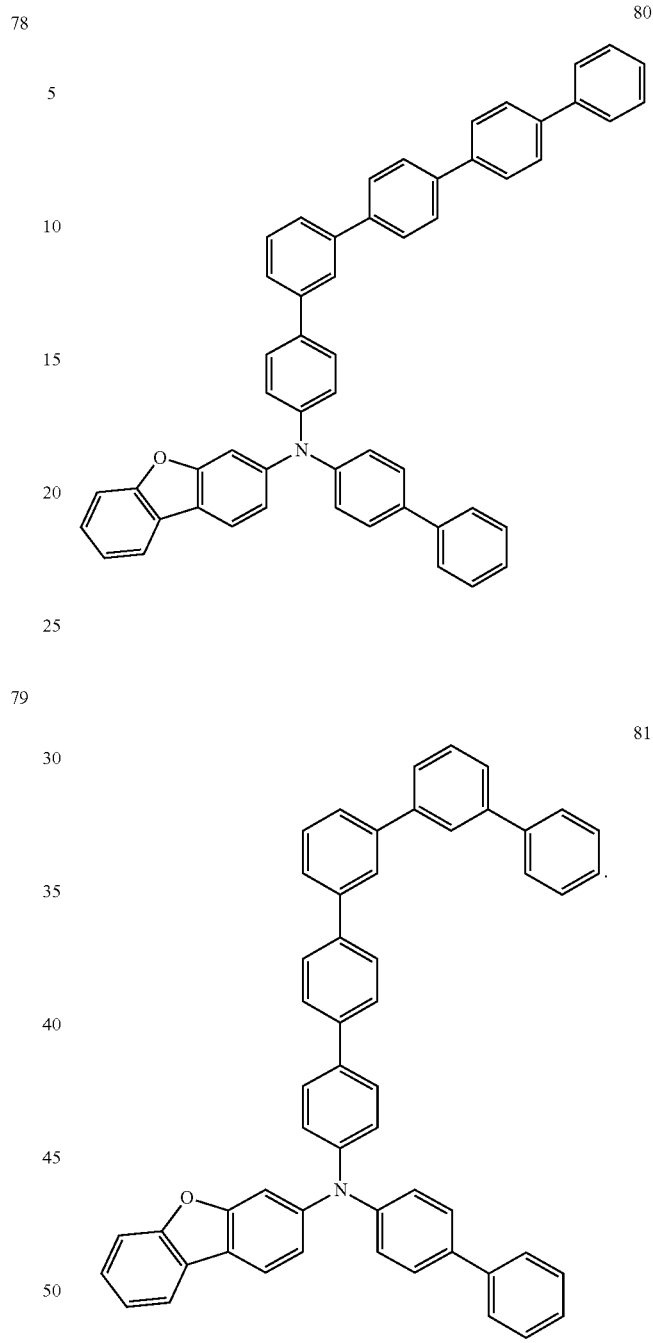

What is claimed is:

1. An amine derivative, represented by following Formula 1:

[Formula 1]

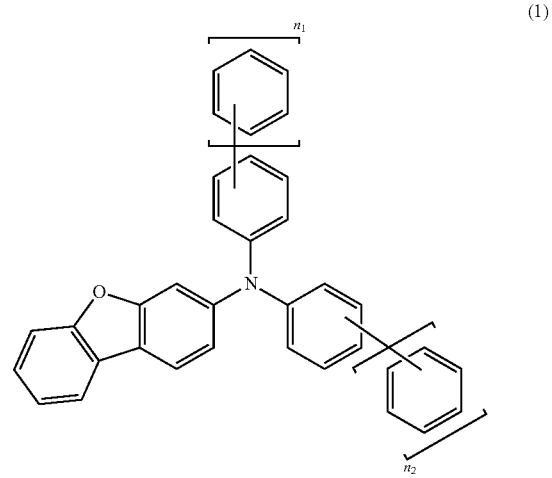

(1)

wherein in Formula 1,
$n_1$ is an integer from 1 to 4;
$n_2$ is an integer from 2 to 4; and
$n_1+n_2$ is at least 4.

2. The amine derivative of claim 1, wherein $n_1$ is 2, and $n_2$ is 2.

3. The amine derivative of claim 1, wherein a first arylene group binding to a nitrogen atom in Formula 1 binds to a second arylene group or an aryl group at a para position of the first arylene group binding to the nitrogen atom.

4. The amine derivative of claim 3, wherein all arylene groups and aryl groups, which bind to the first arylene group binding to the nitrogen atom in Formula 1, bind at a para position of an adjacent arylene group.

5. A material for an organic electroluminescent device comprising an amine derivative represented by following Formula 1:

[Formula 1]

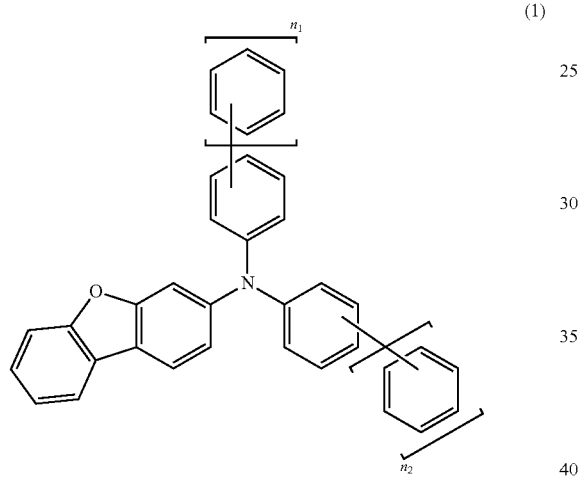

where,
$n_1$ is an integer from 1 to 4;
$n_2$ is an integer from 2 to 4; and
$n_1+n_2$ is at least 4.

6. The material for an organic electroluminescent device of claim 5, wherein $n_1$ is 2, and $n_2$ is 2.

7. The material for an organic electroluminescent device of claim 5, wherein a first arylene group binding to a nitrogen atom in Formula 1 binds to a second arylene group or an aryl group at a para position of the first arylene group linked to the nitrogen atom.

8. The material for an organic electroluminescent device of claim 7, wherein all arylene groups and aryl groups, which bind to the first arylene group binding to the nitrogen atom in Formula 1, bind at a para position of an adjacent arylene group.

9. The material for an organic electroluminescent device of claim 5, wherein the amine derivative comprises at least one of compounds 1 to 81:

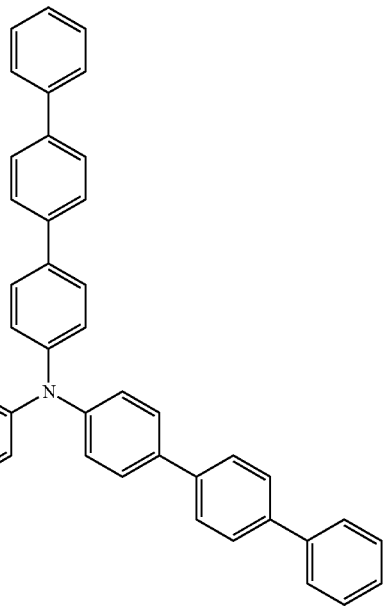

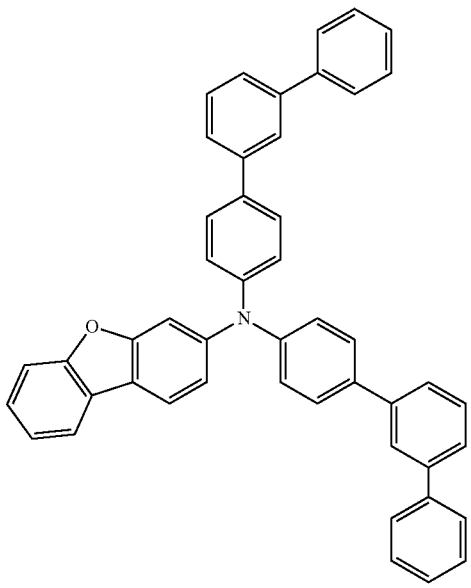

3
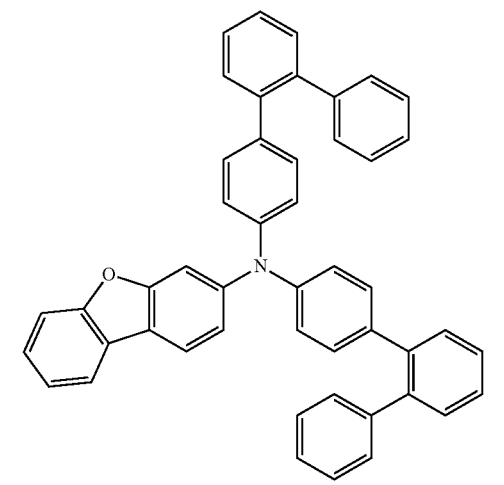
4
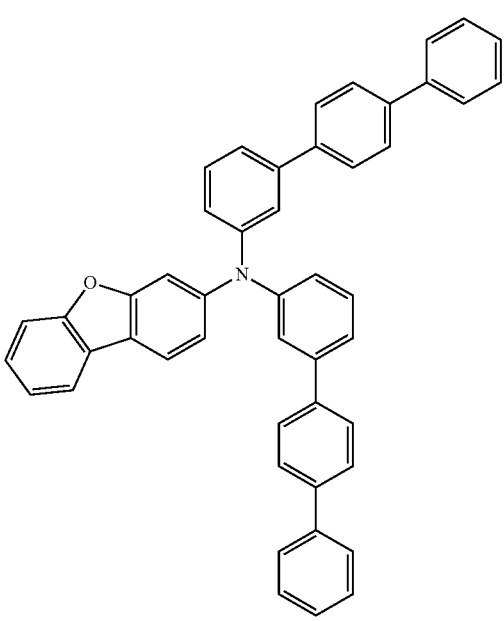
5
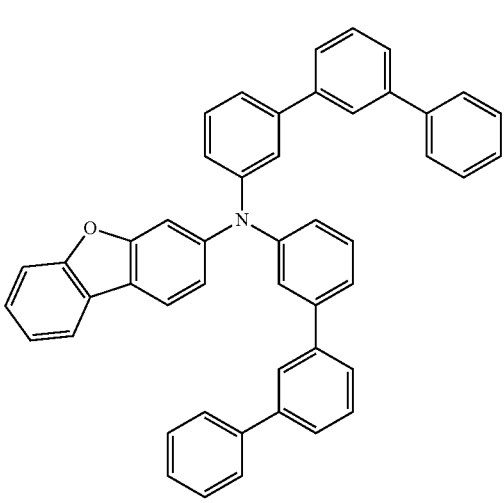
6
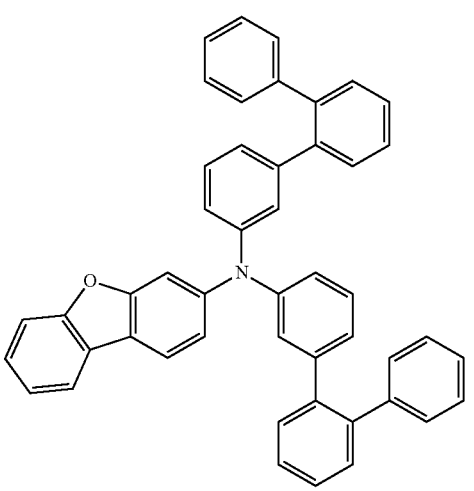
7
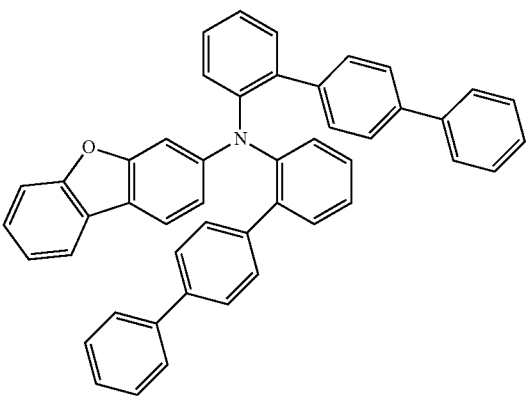
8
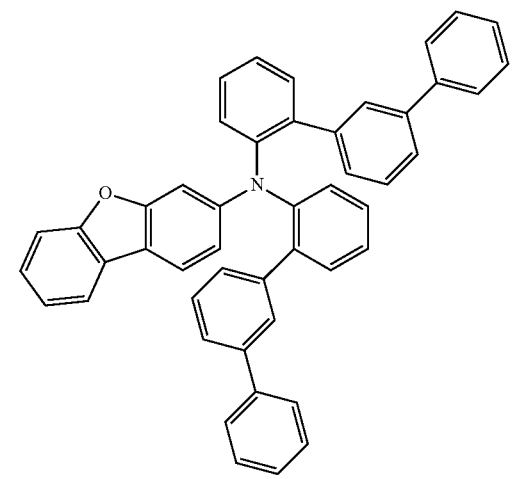

-continued
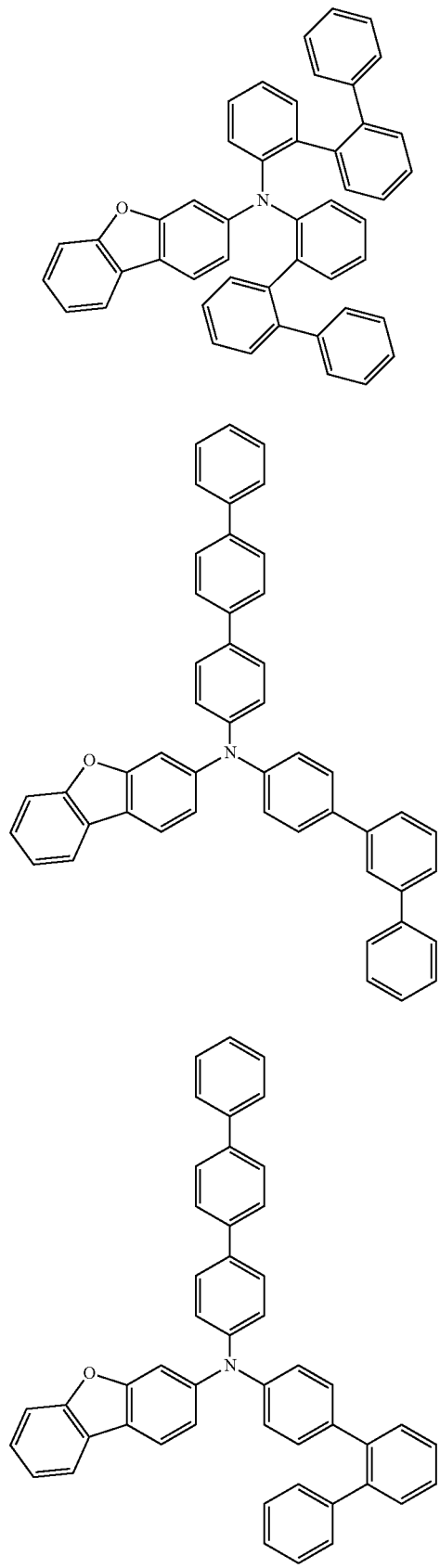
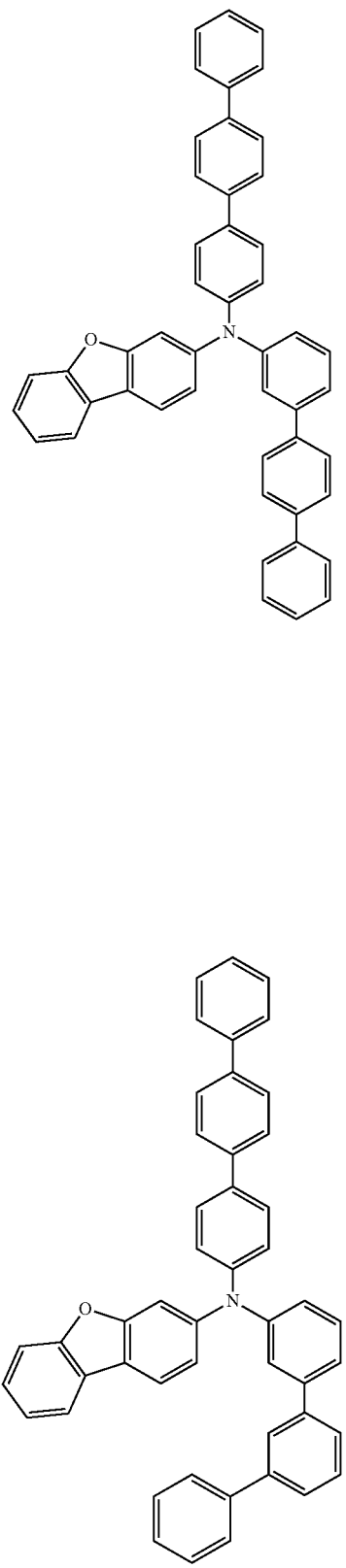

14
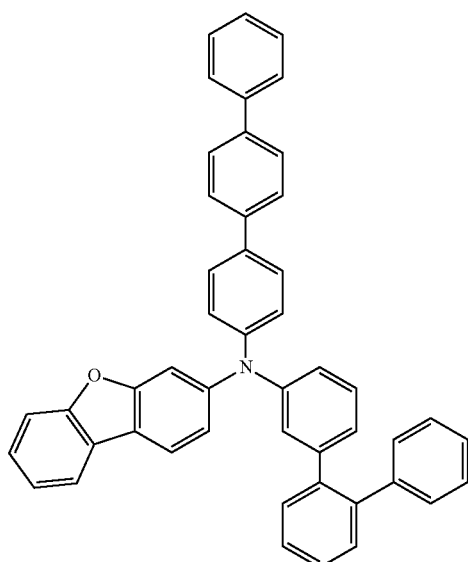
15
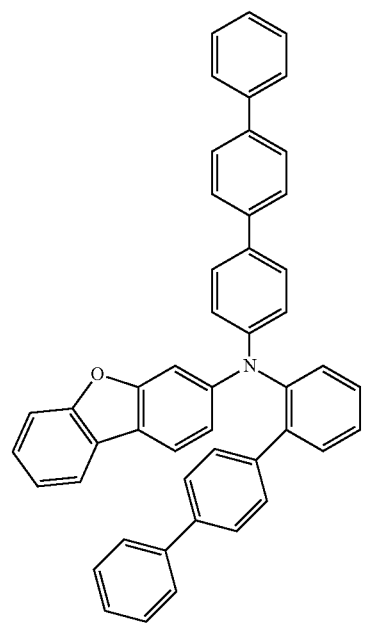
16
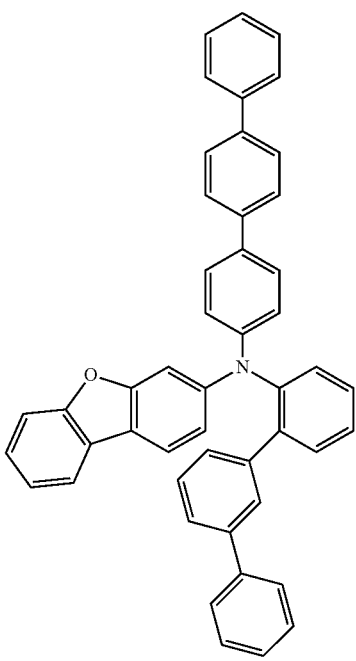
17
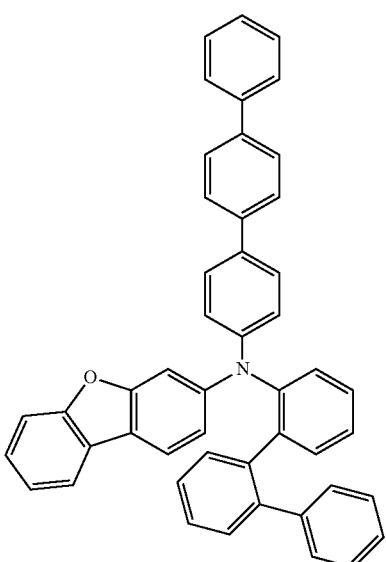

18
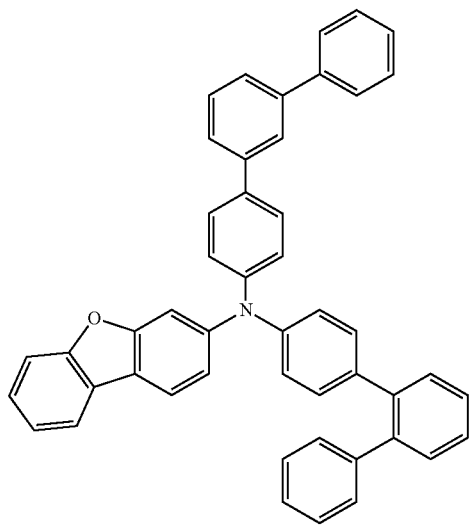
19
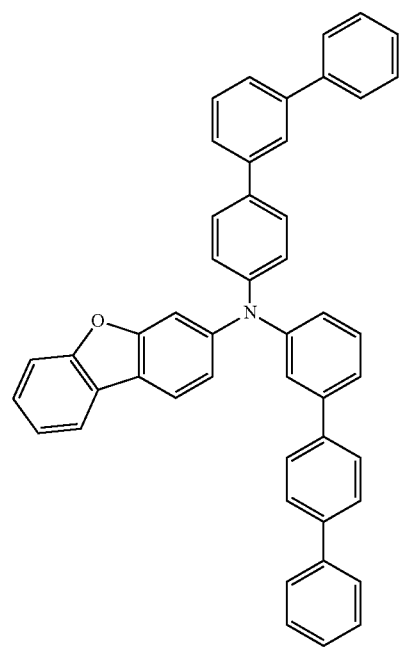
20
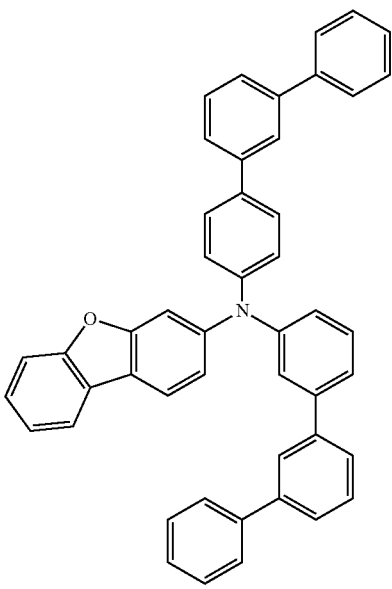
21
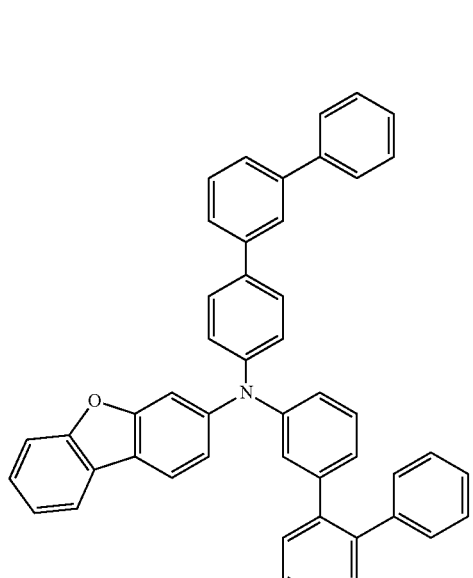

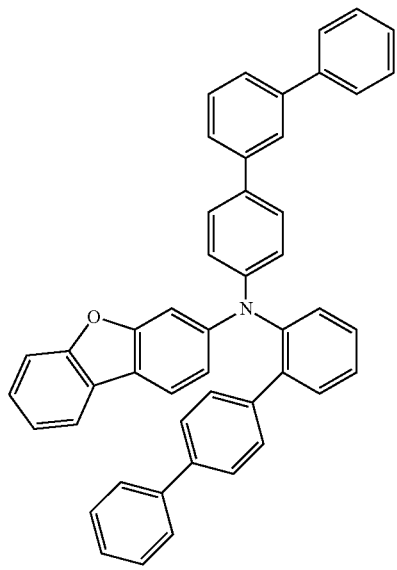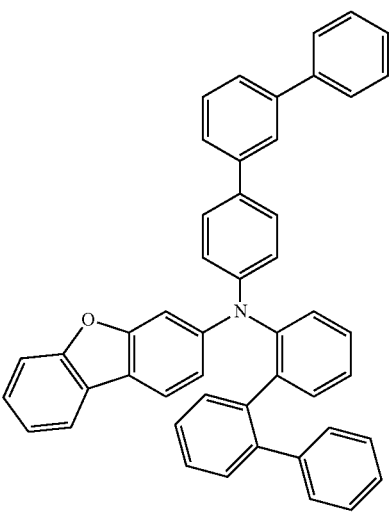

27
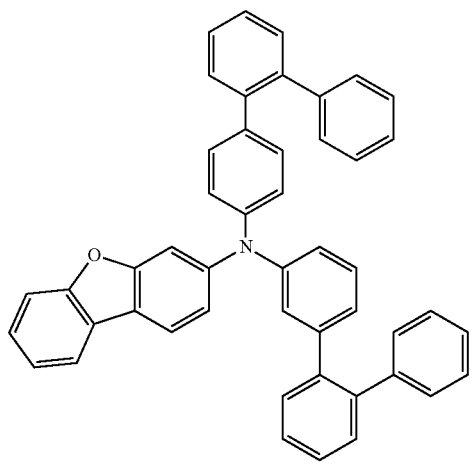
28
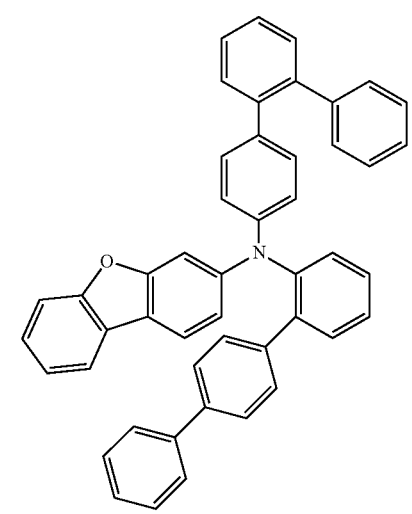
29
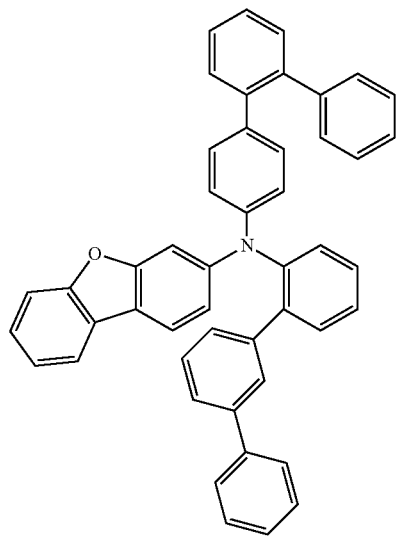
30
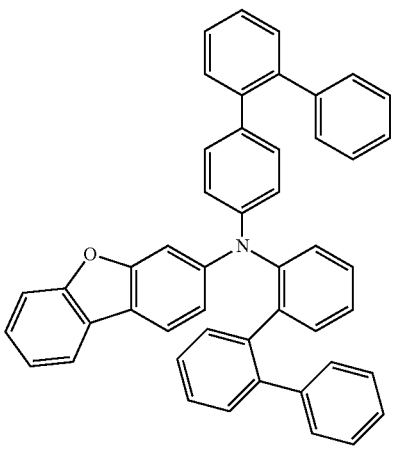
31
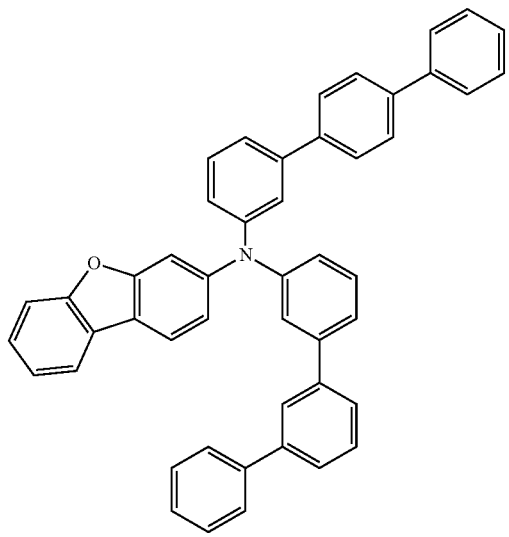
32
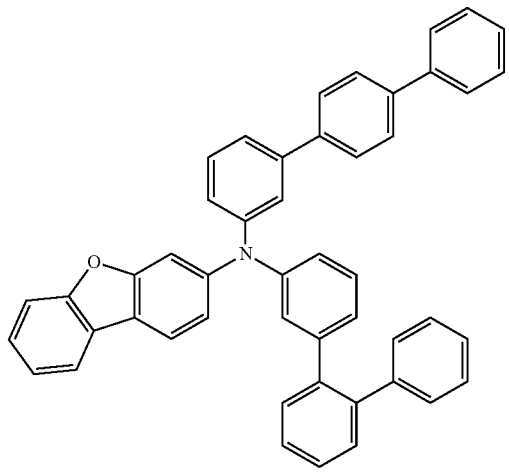

33
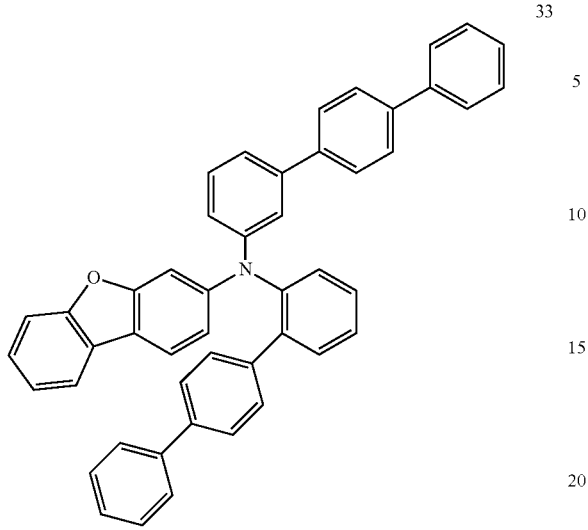
34
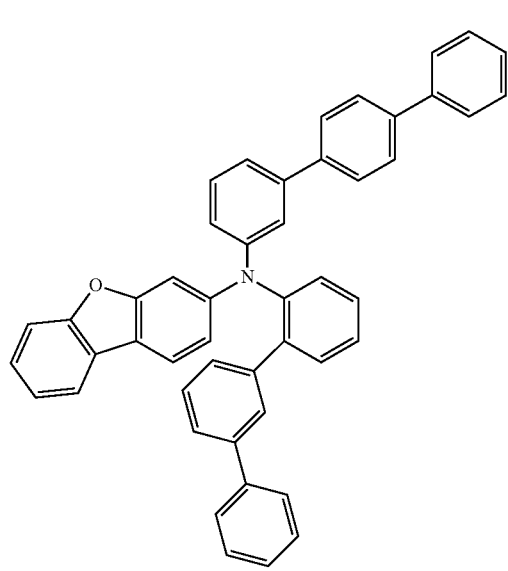
35
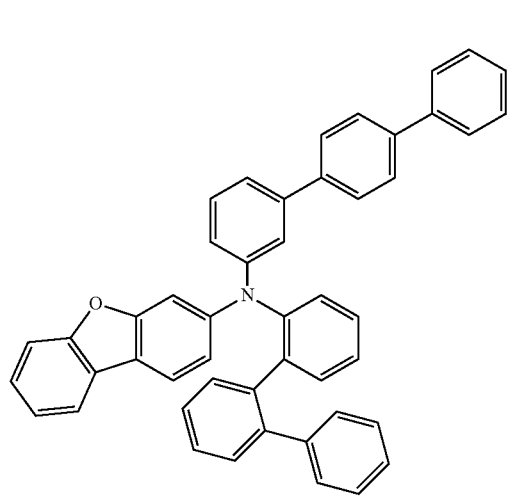
36
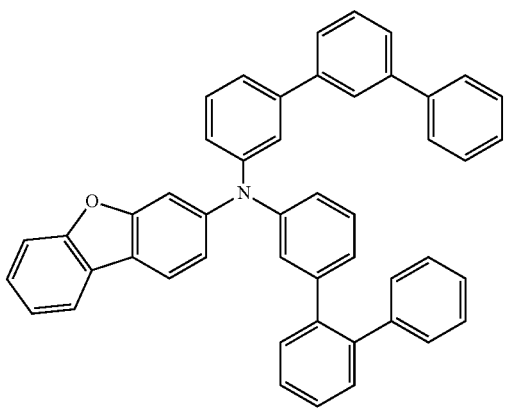
38
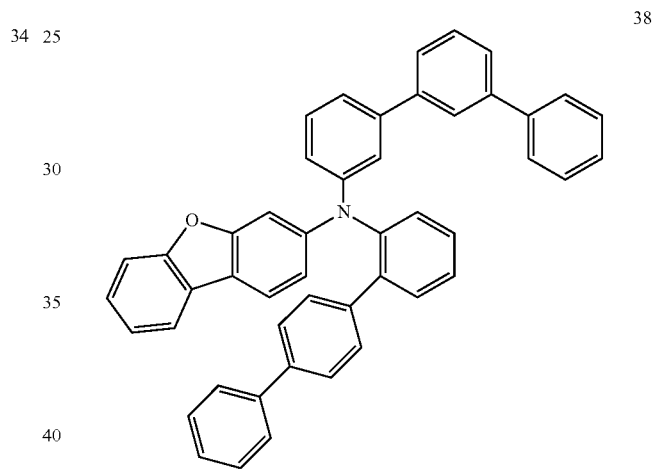
39
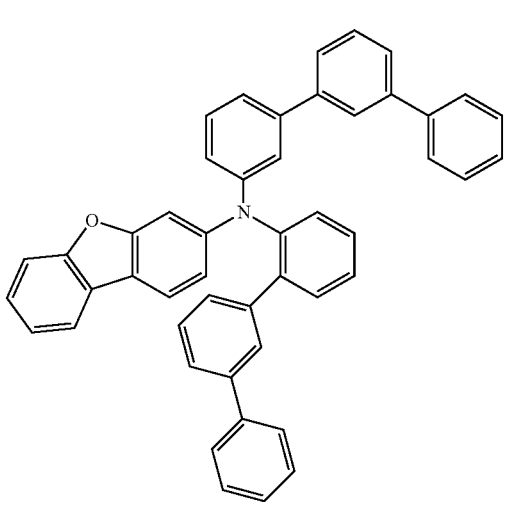

40
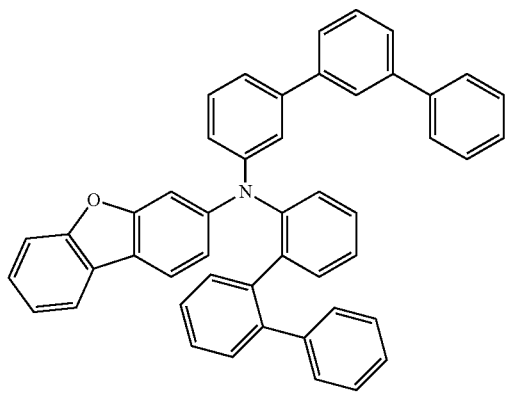
41
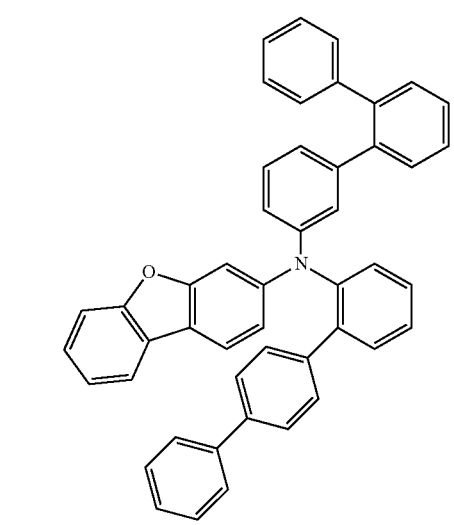
42
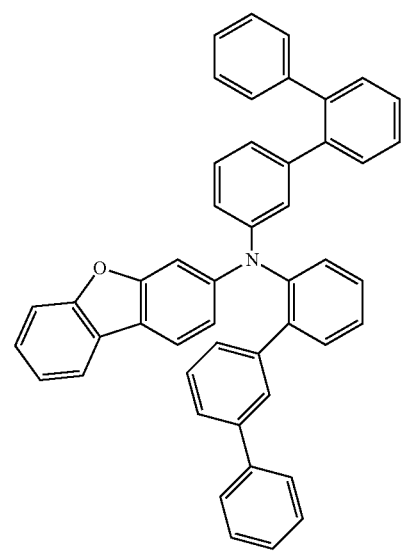
43
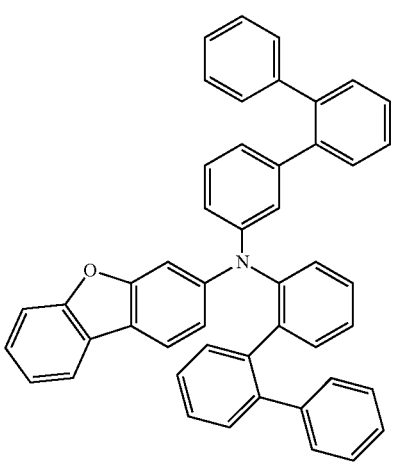
44
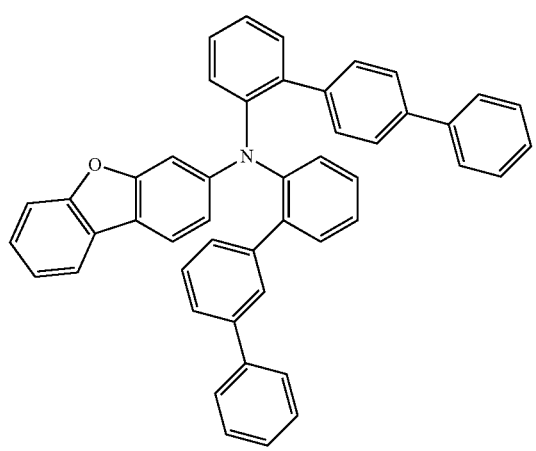
45

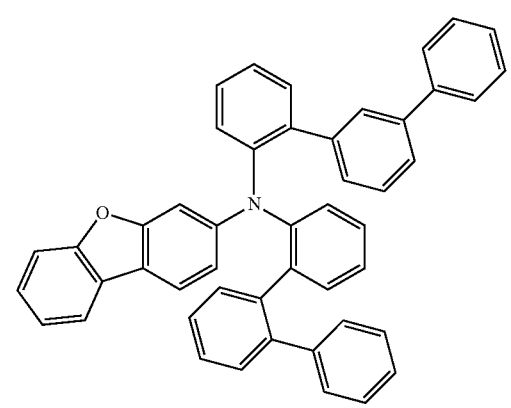
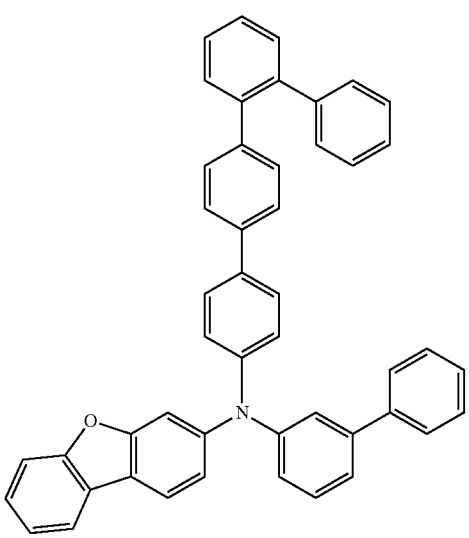
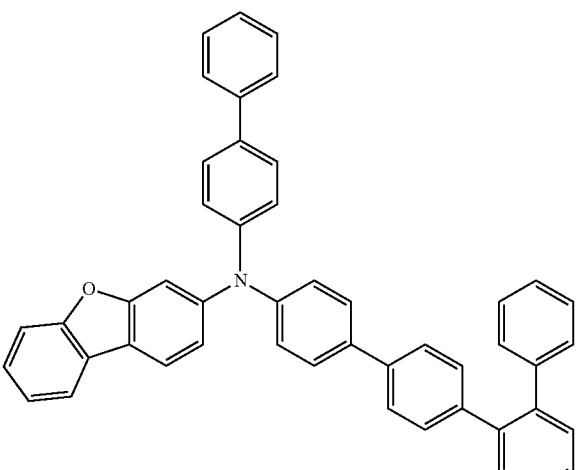
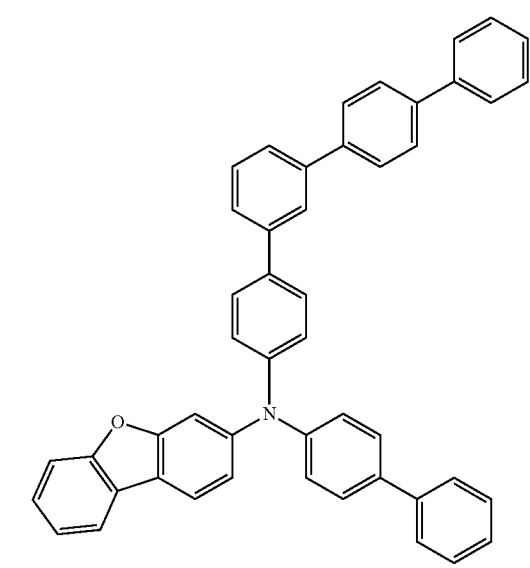

52
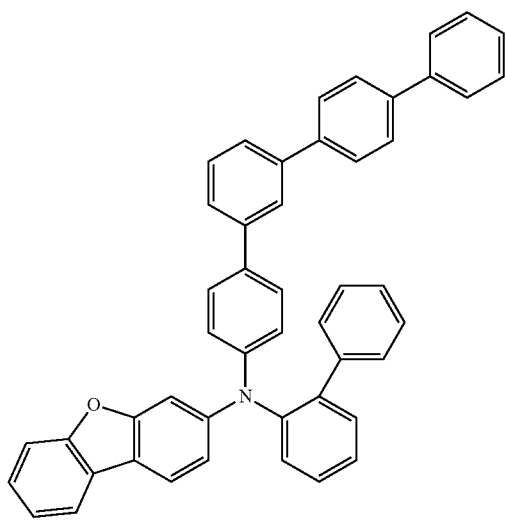
53
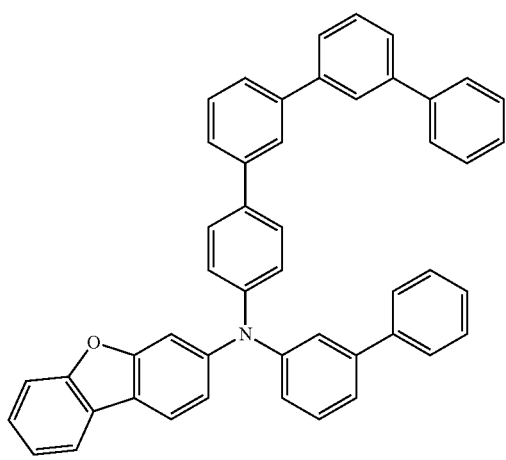
54
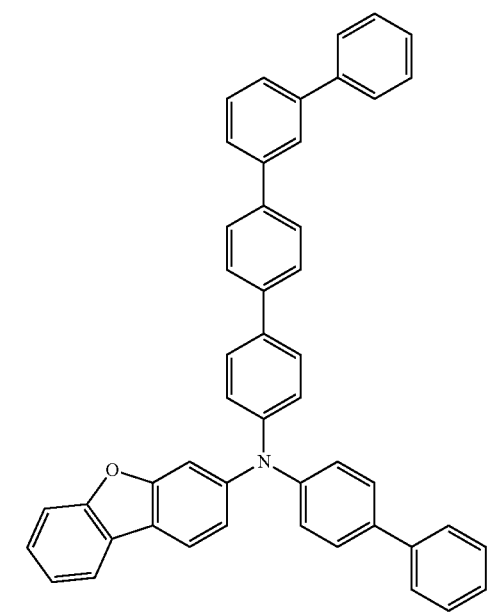
55
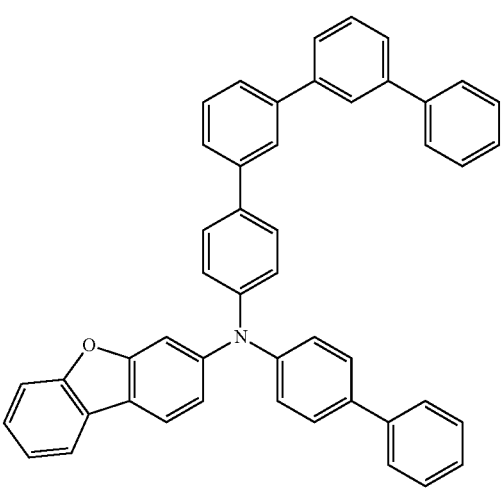
56
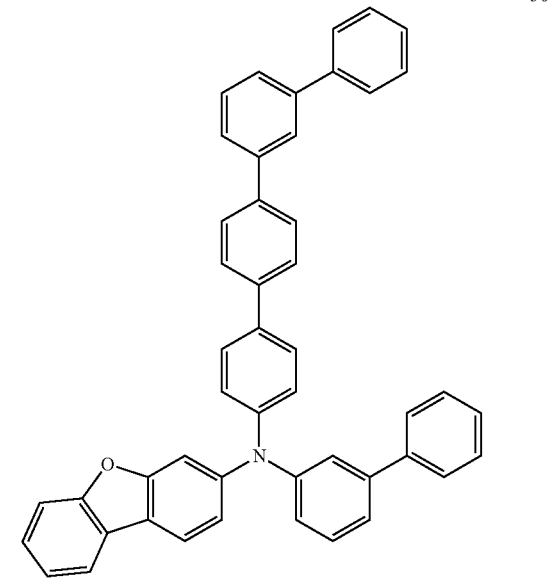
57
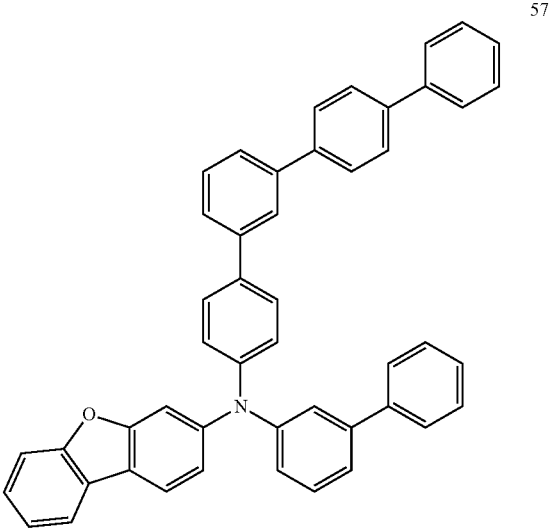

58
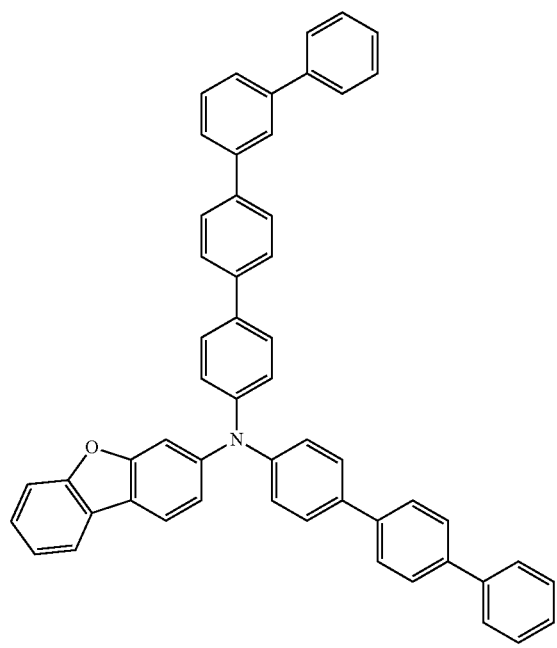
59
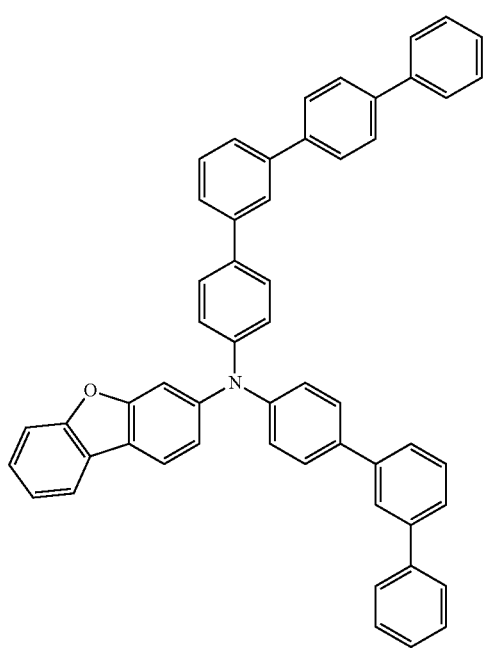
60
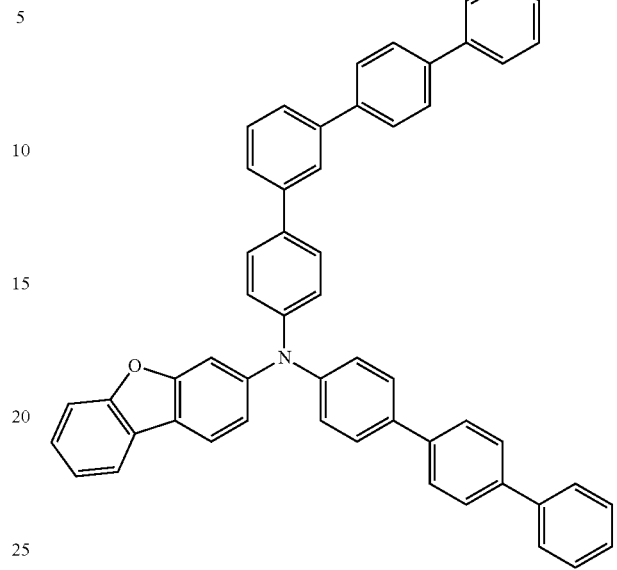
61
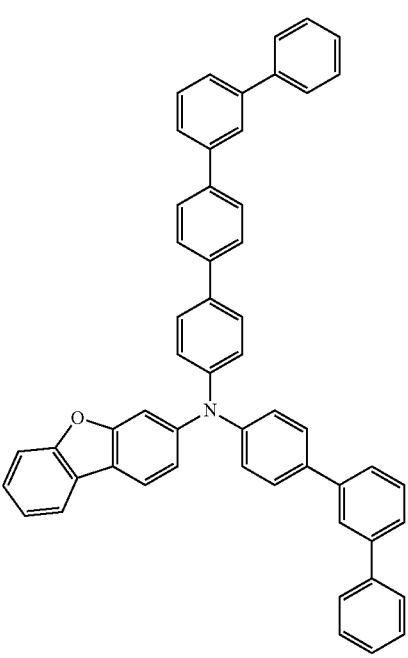

77
-continued
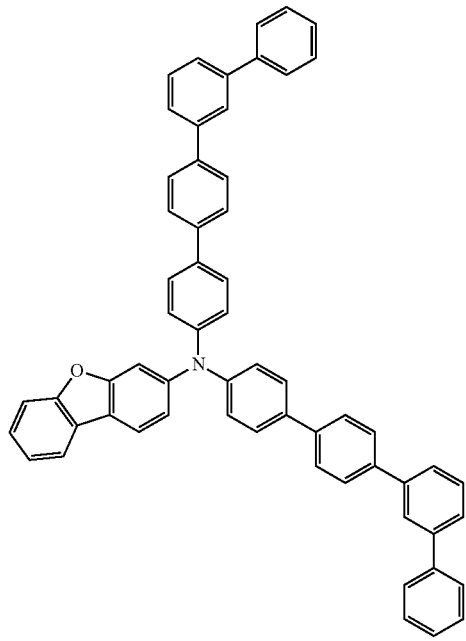
62
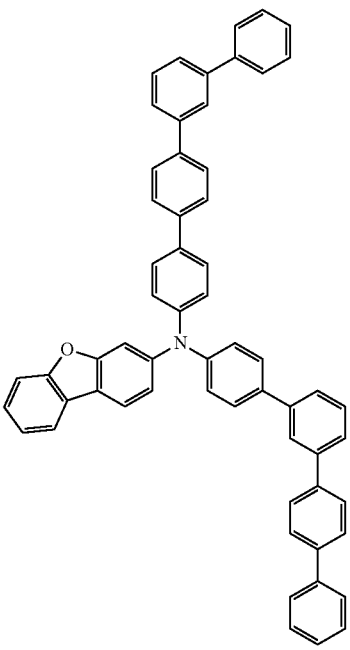
64
78
-continued
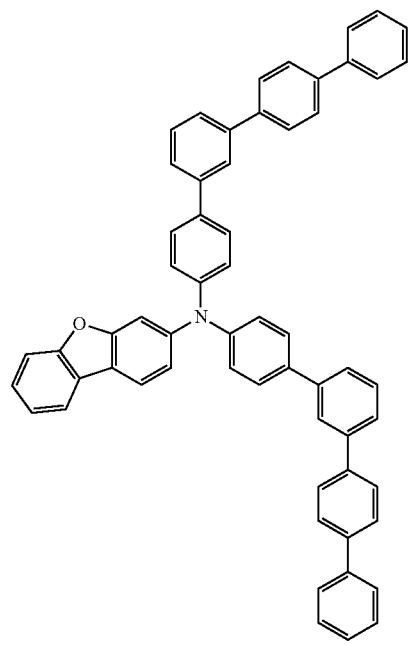
63
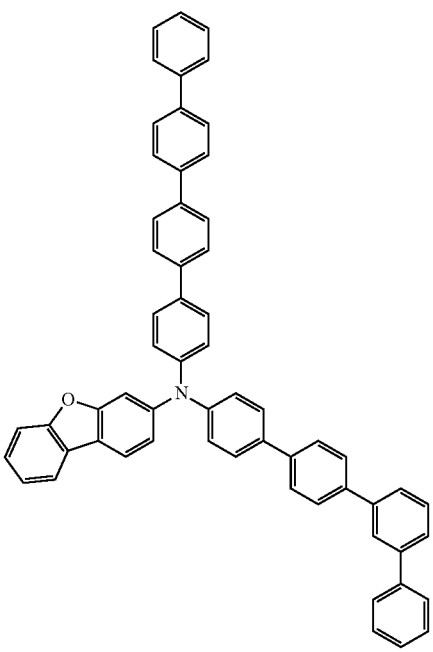
65

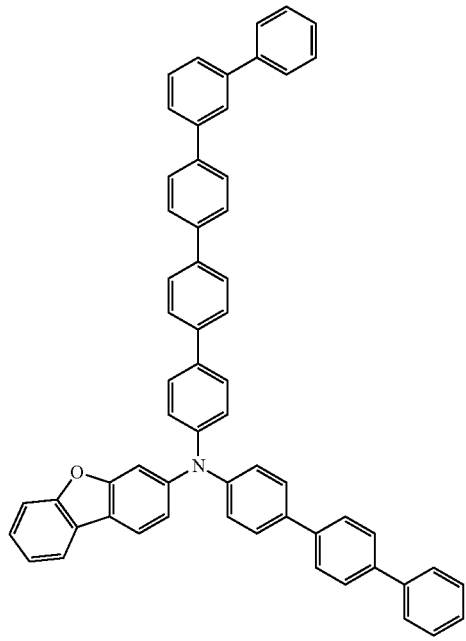
66
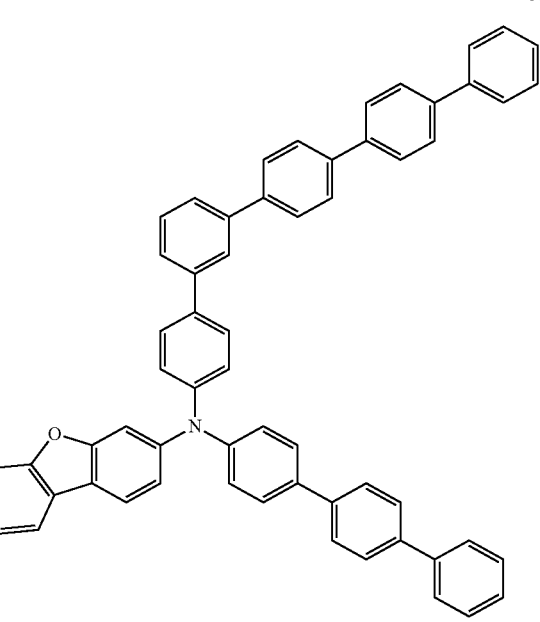
68
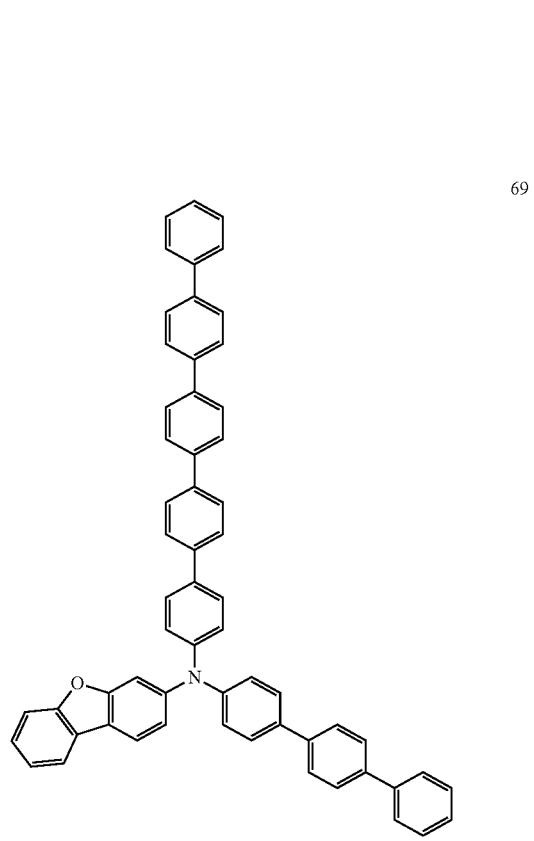
67

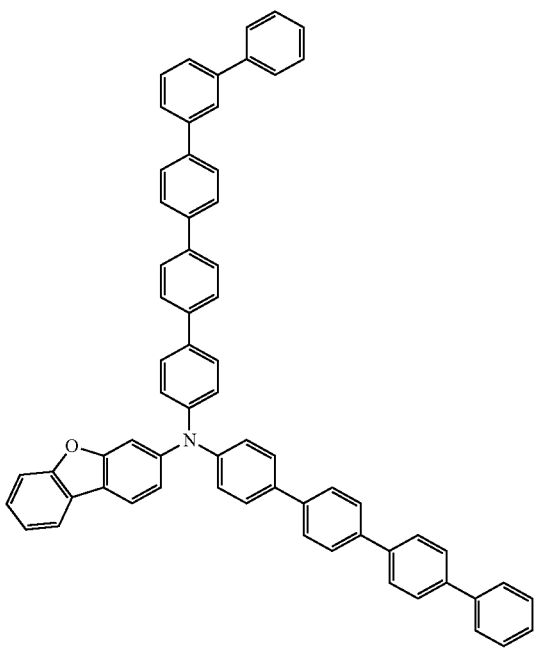
70
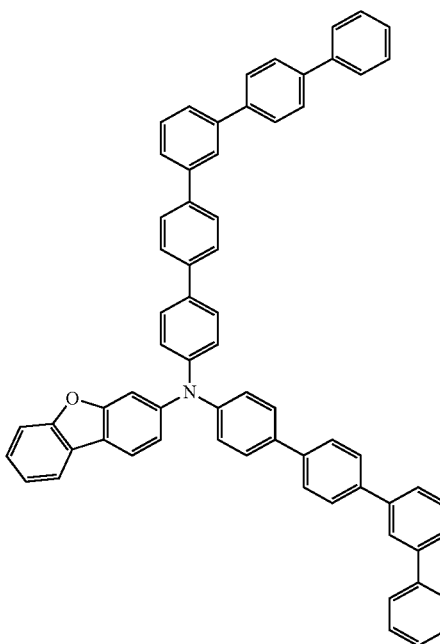
72
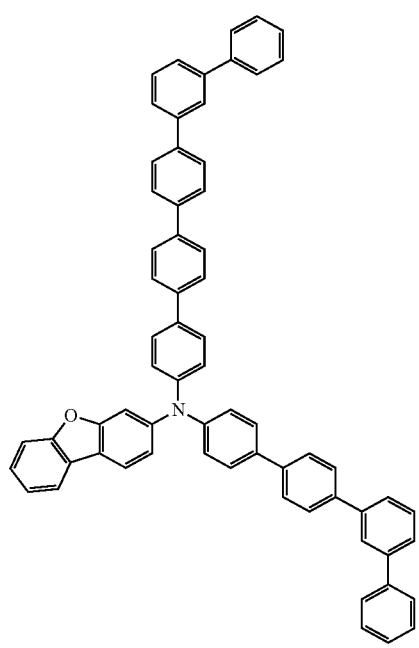
71
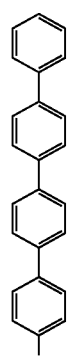
73
74

83
-continued
84
-continued
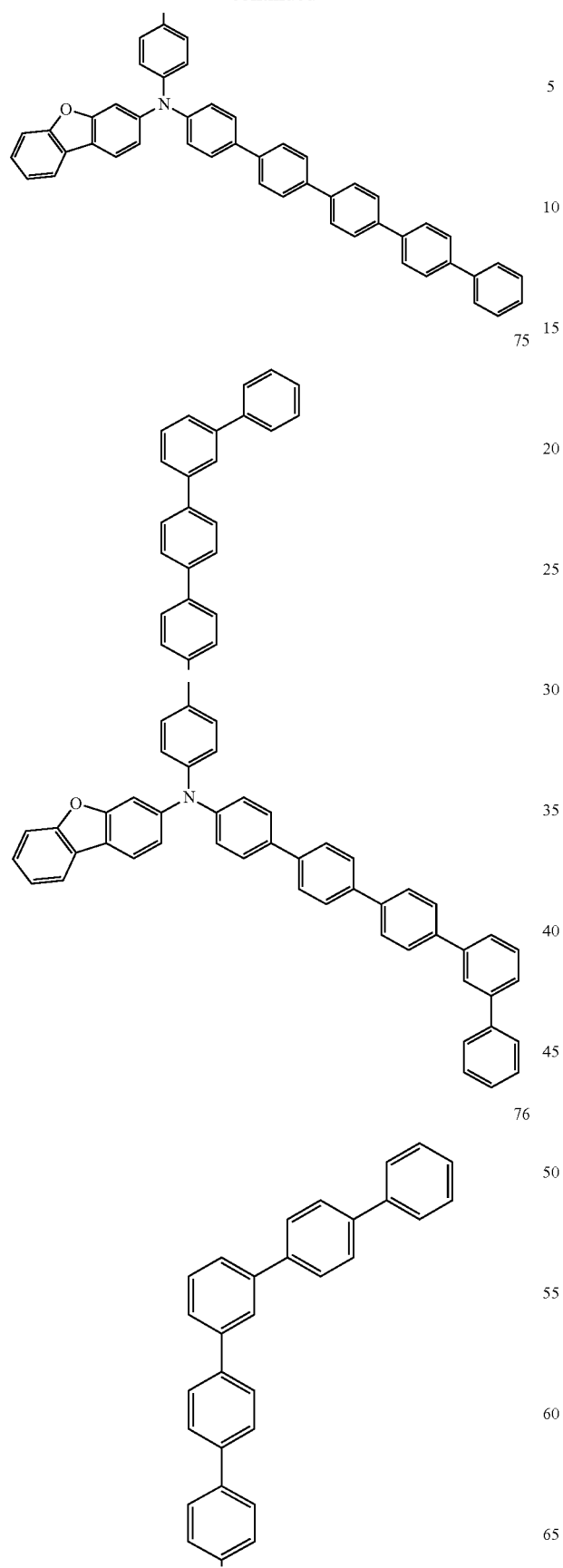
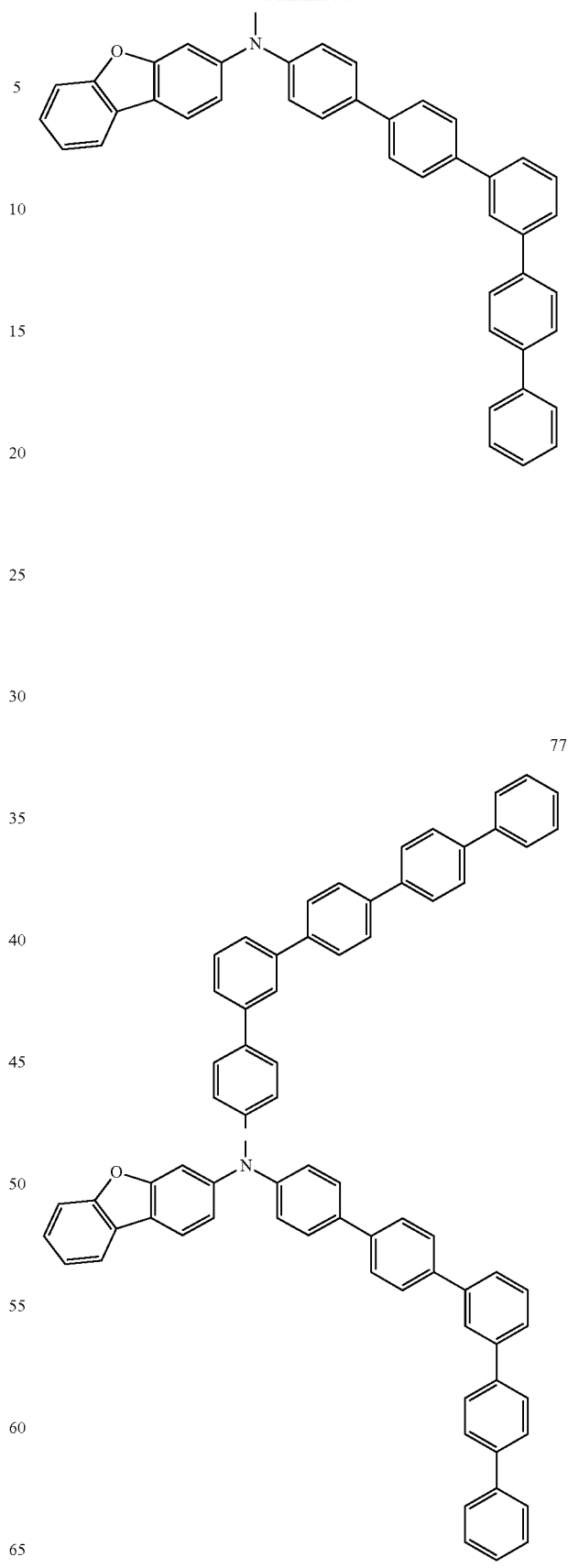

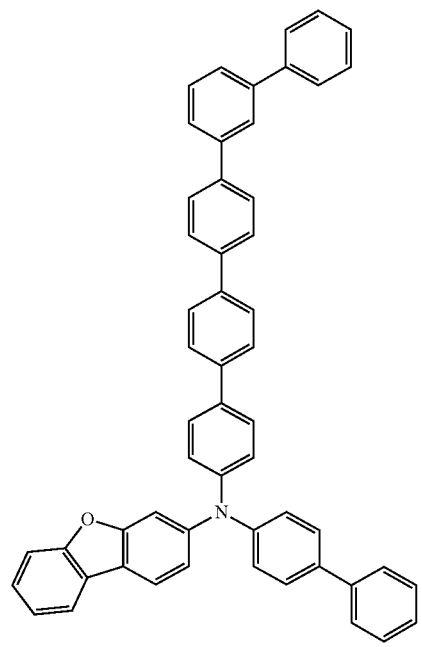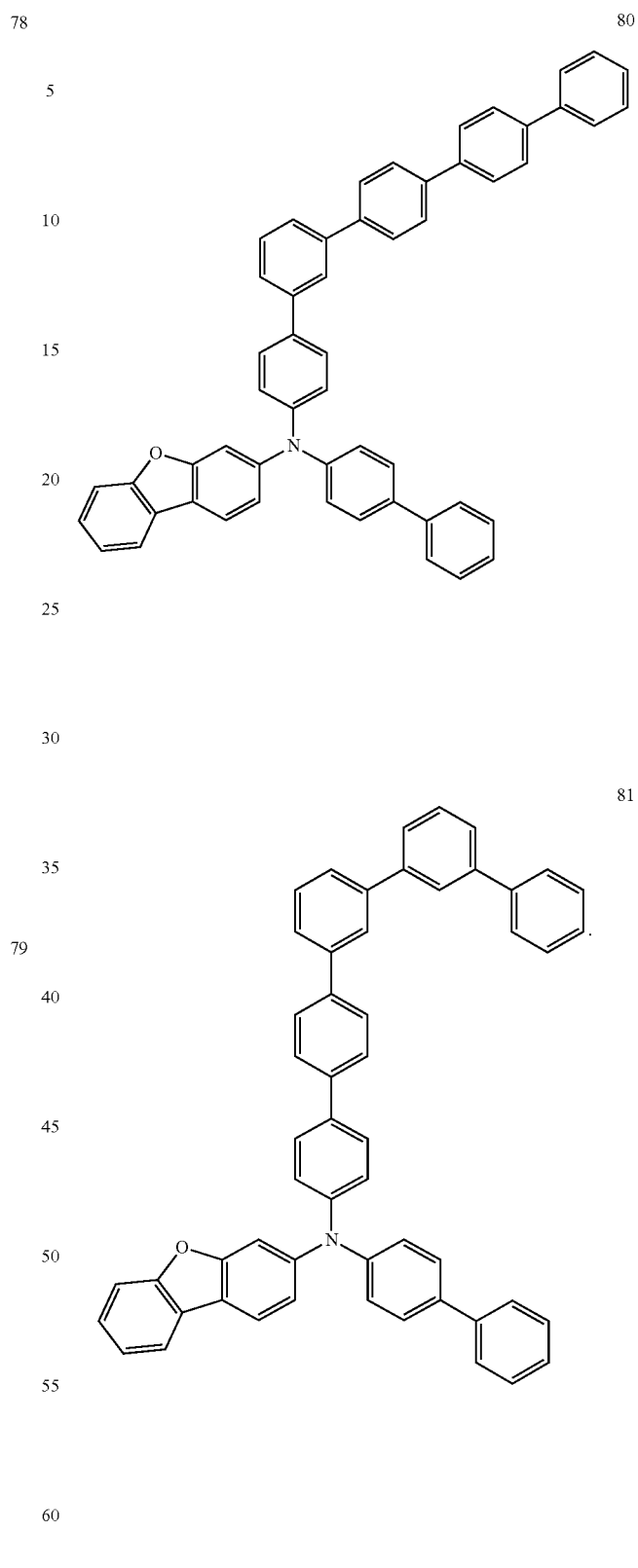
10. An organic electroluminescent device comprising a material for an organic electroluminescent device in at least one layer between an emission layer and an anode, wherein the material for an organic electroluminescent device is represented by following Formula 1:

Formula 1

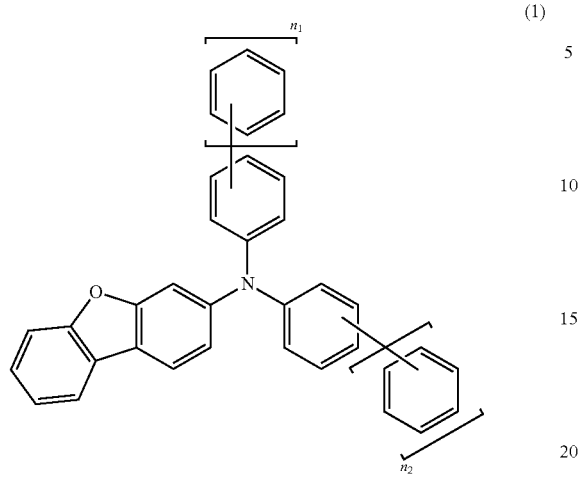

where,
$n_1$ is an integer from 1 to 4;
$n_2$ is an integer from 2 to 4; and
$n_1+n_2$ is at least 4.

11. The organic electroluminescent device of claim 10, wherein $n_1$ is 2, and $n_2$ is 2.

12. The organic electroluminescent device of claim 10, wherein a first arylene group binding to a nitrogen atom in Formula 1 binds to a second arylene group or an aryl group at a para position of the first arylene group linked to the nitrogen atom.

13. The organic electroluminescent device of claim 12, wherein all arylene groups and aryl groups, which bind to the first arylene group binding to the nitrogen atom in Formula 1, bind at a para position of an adjacent arylene group.

14. The organic electroluminescent device of claim 10, wherein the material for an organic electroluminescent device comprises at least one of compounds 1 to 81:

1

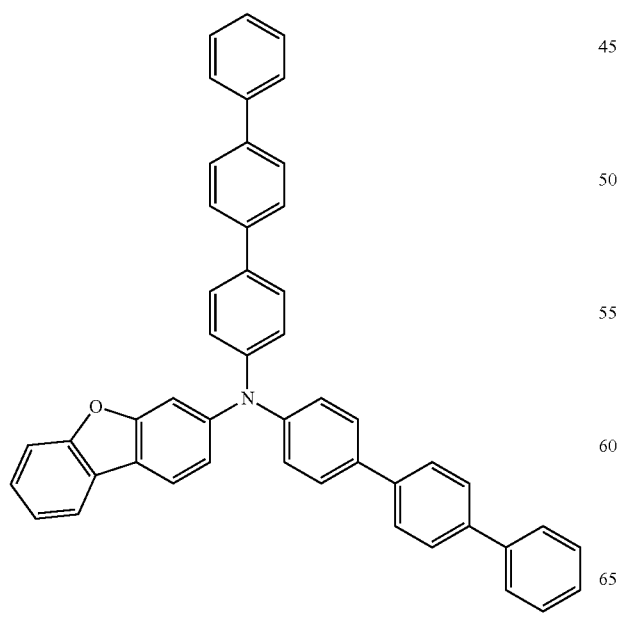

2

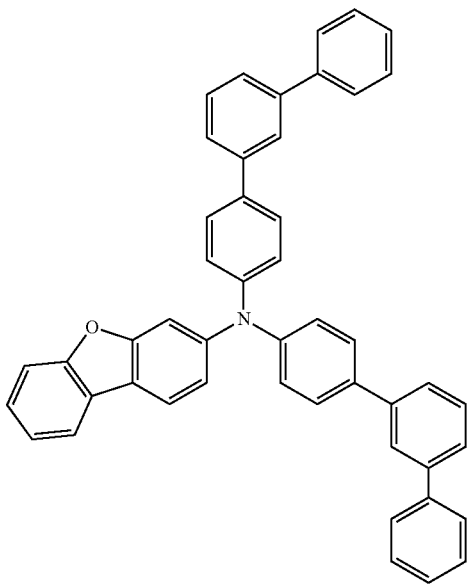

3

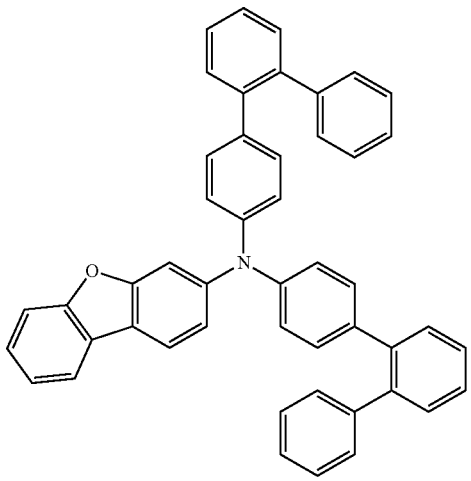

89
-continued
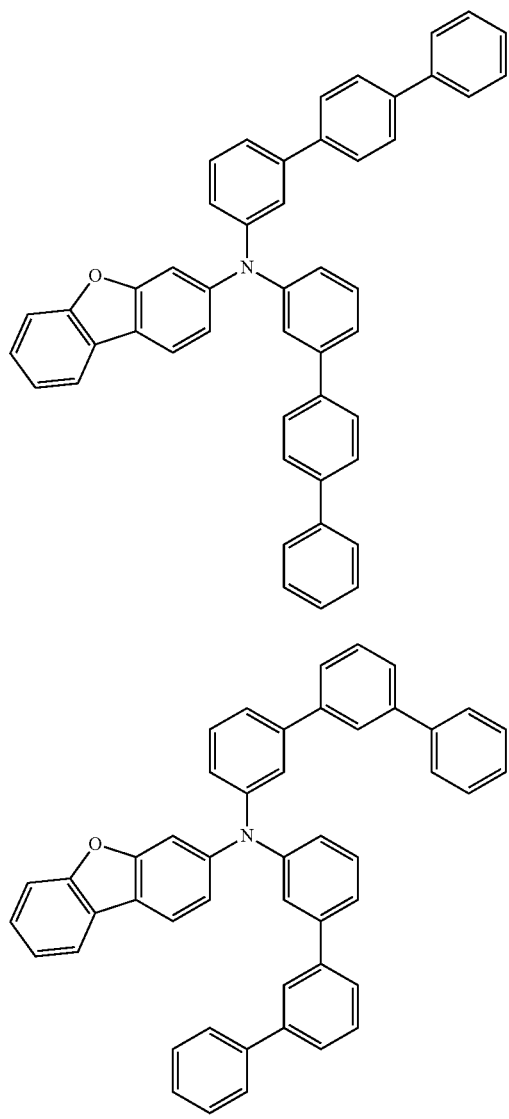
90
-continued
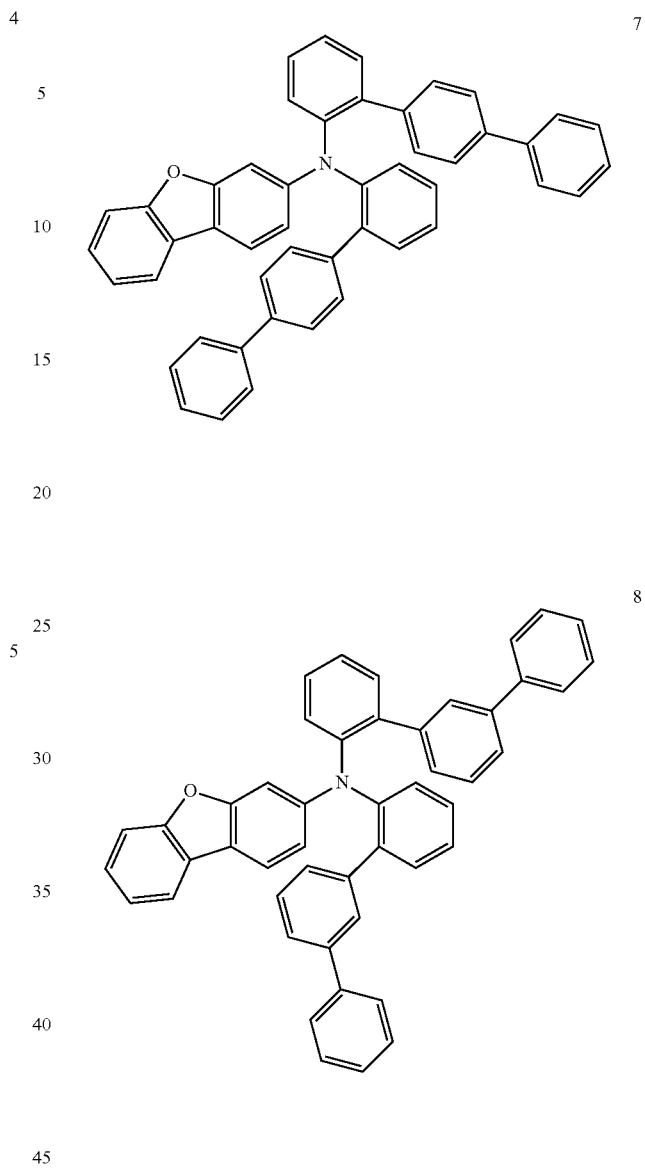
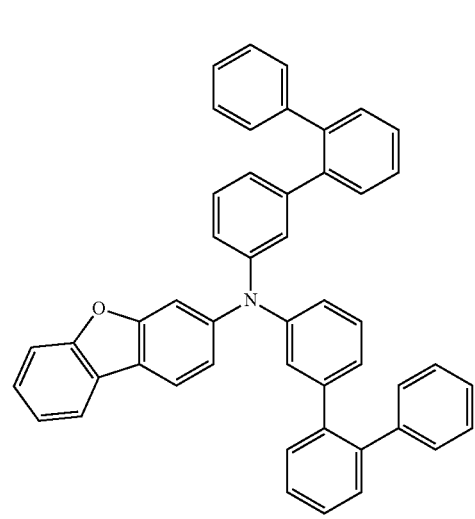
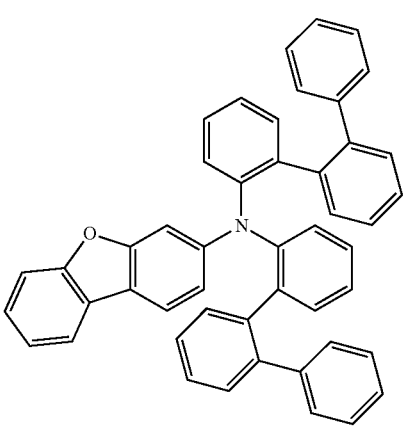

10
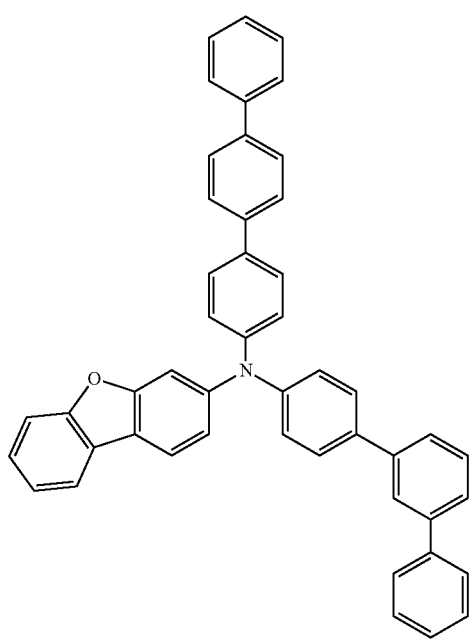
12
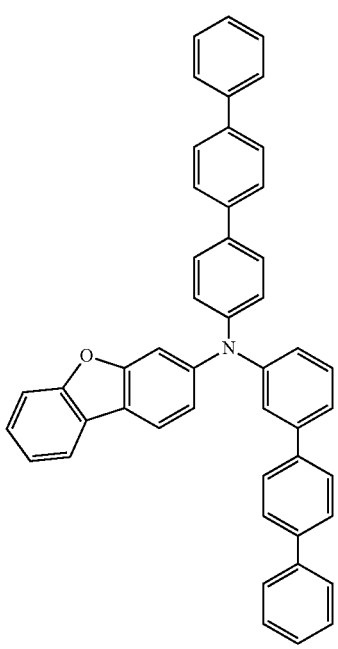
11
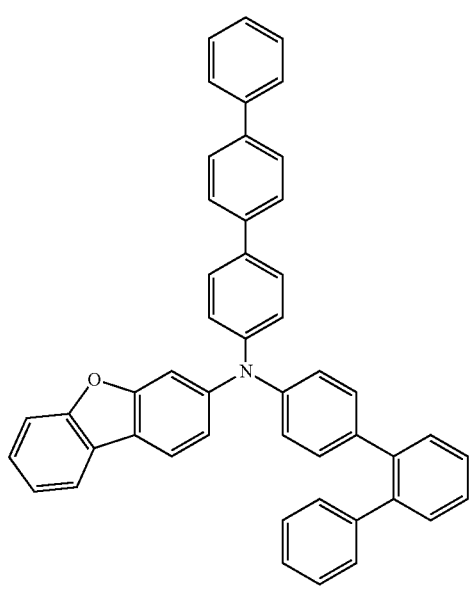
13
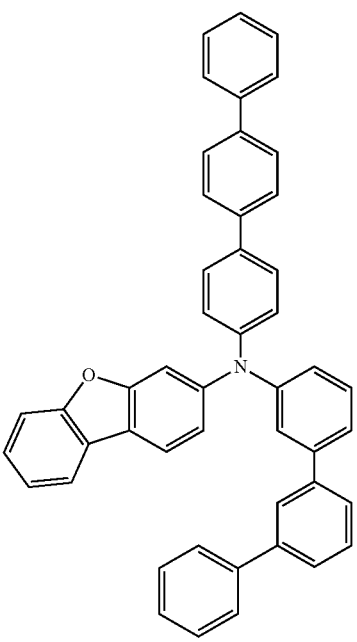

14
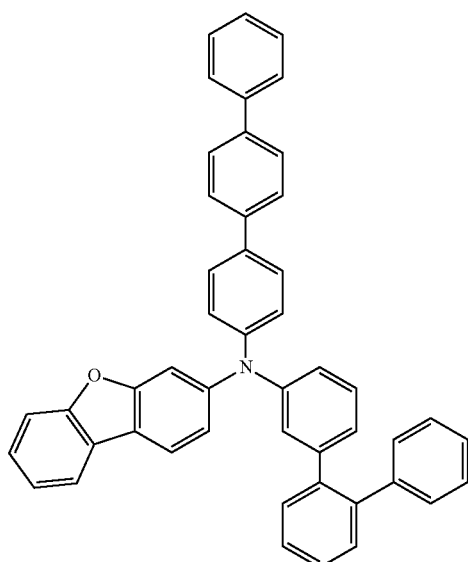
16
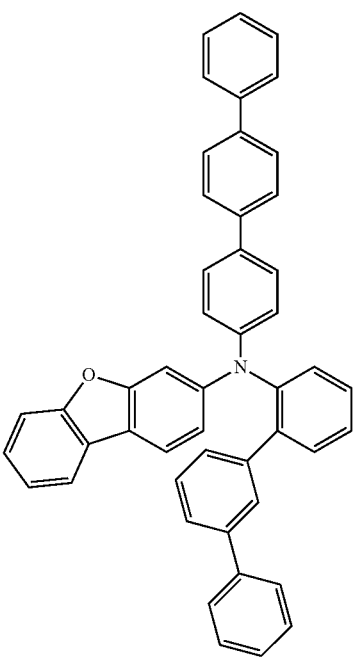
15
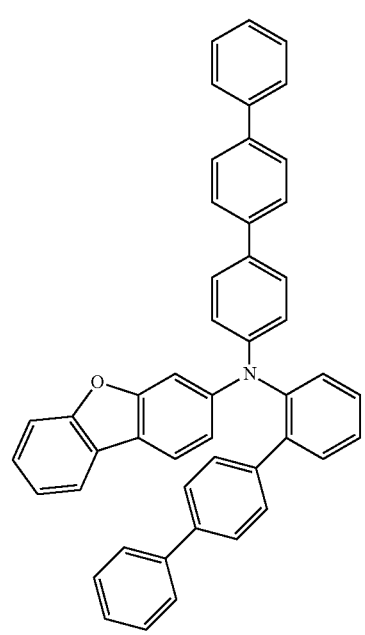
17
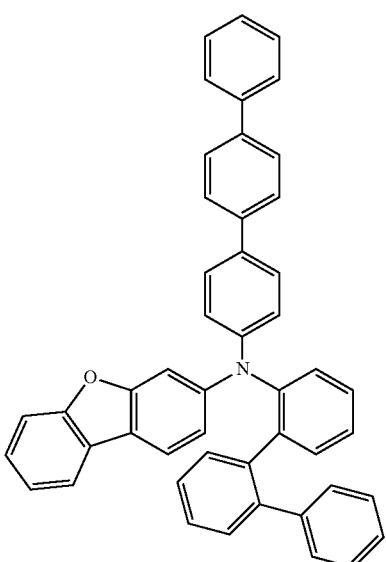

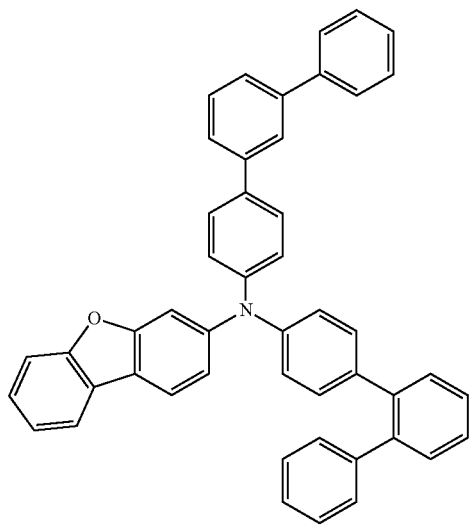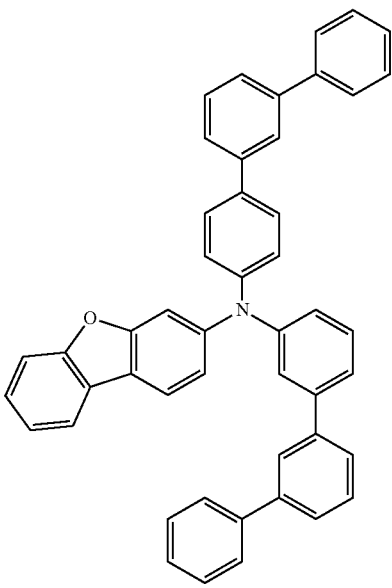

23
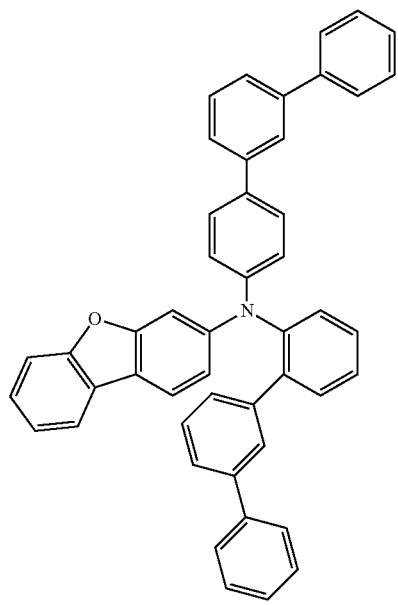
24
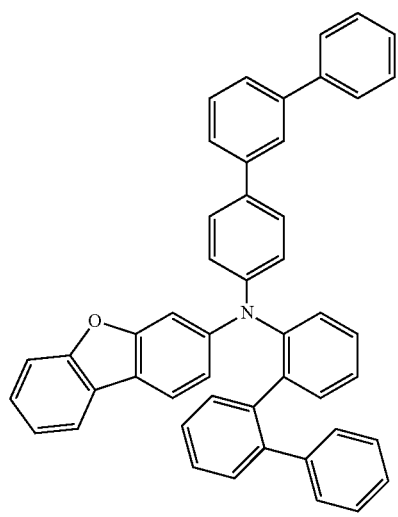
25
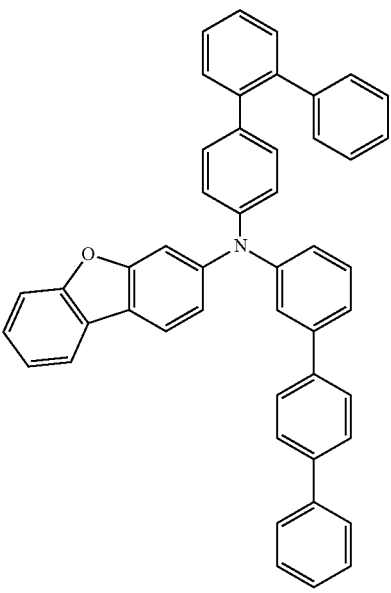
26
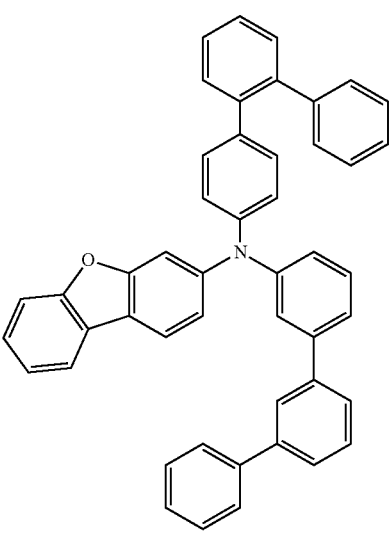
27
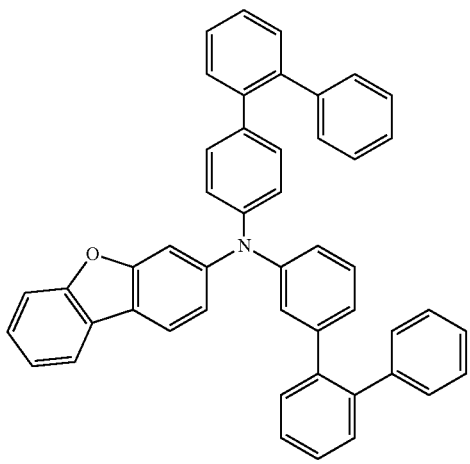

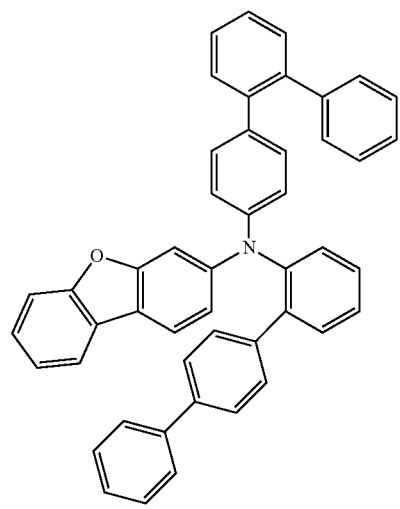
28
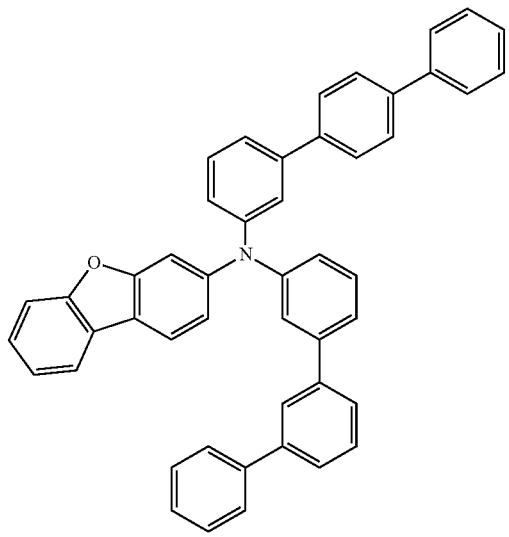
31
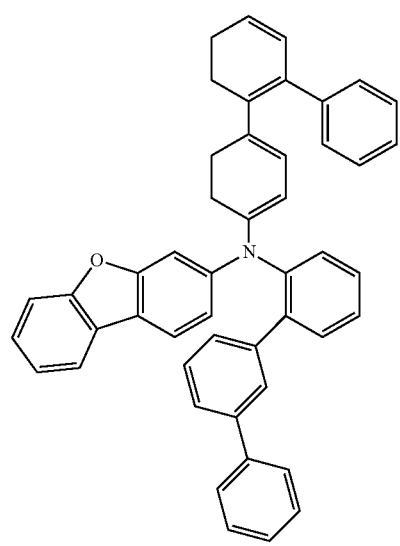
29
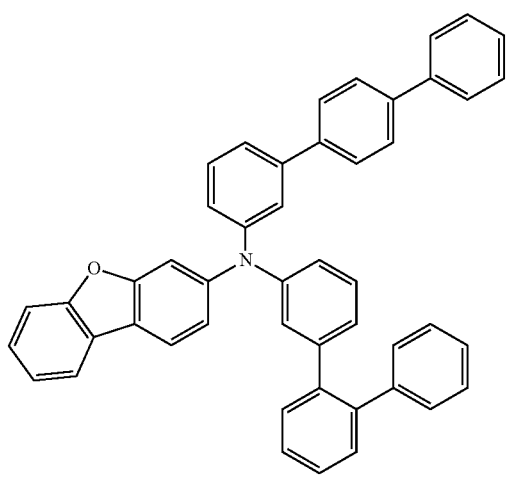
32
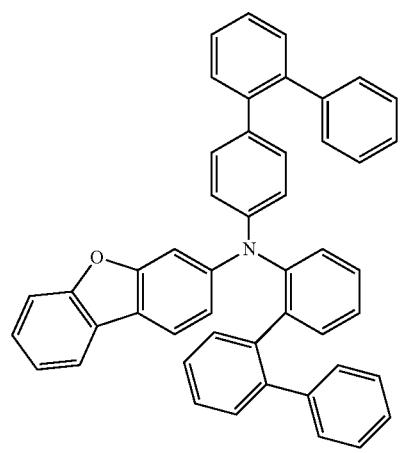
30
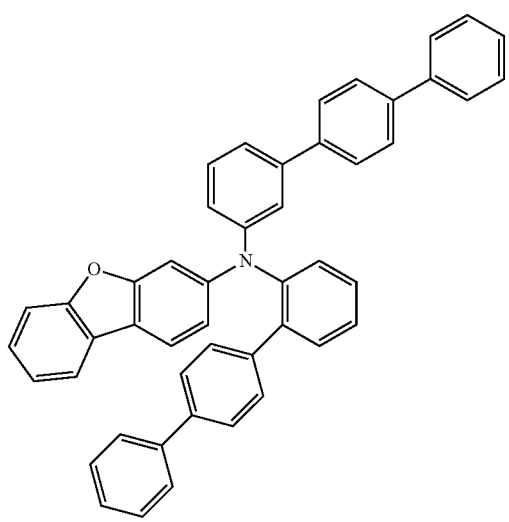
33

101
-continued
34
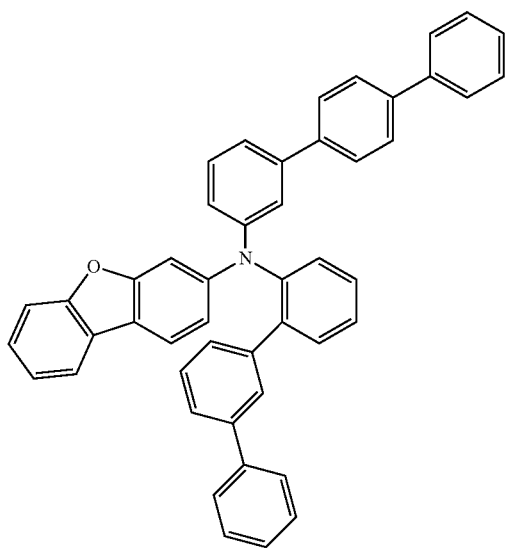
35
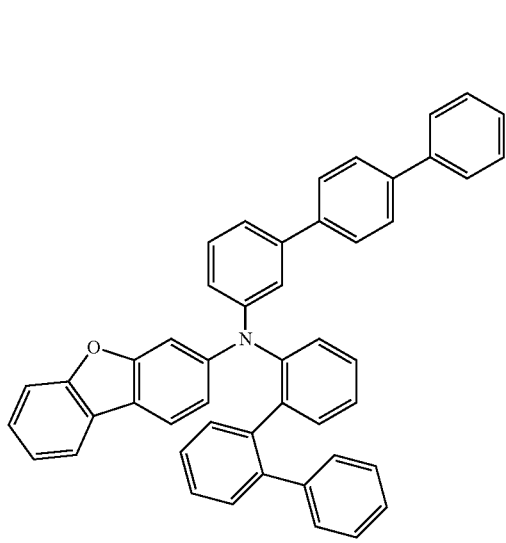
36
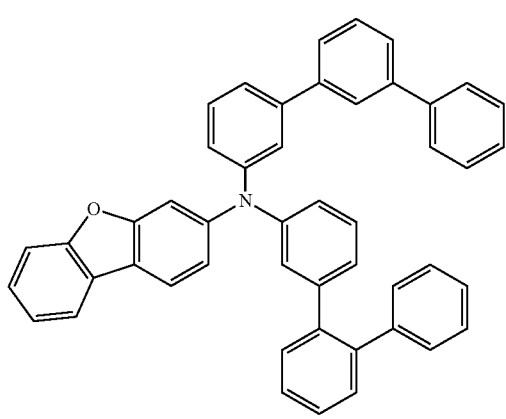
102
-continued
38
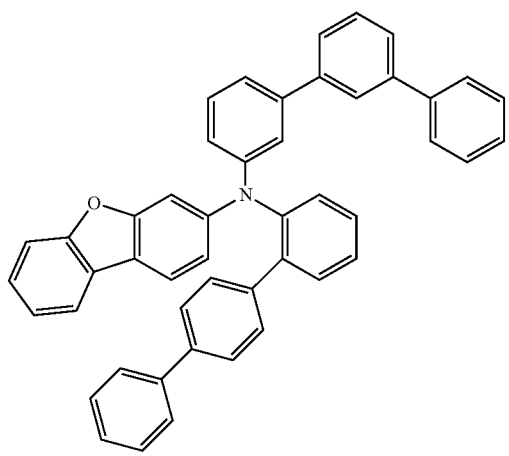
39
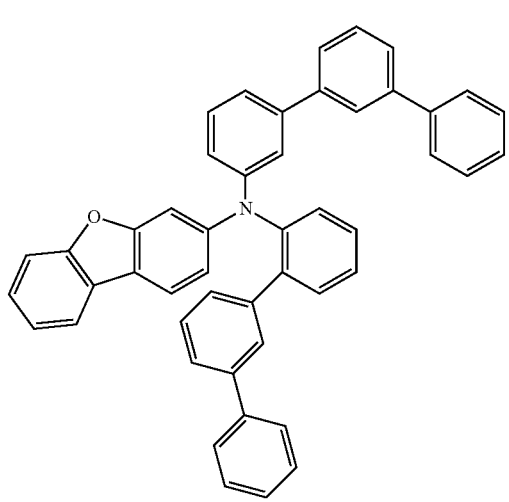
40
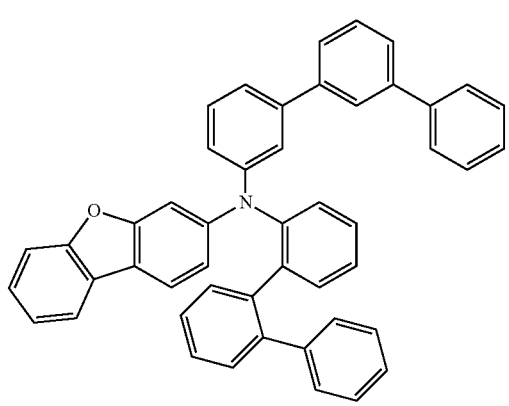

-continued
41
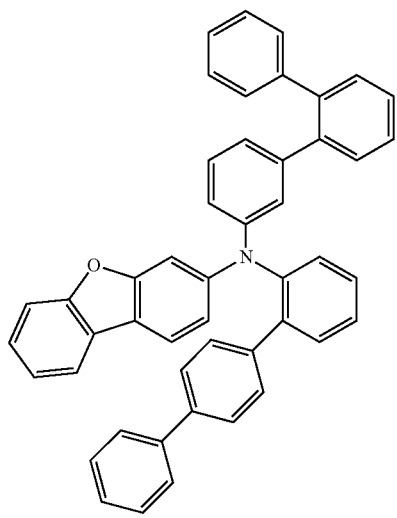
42
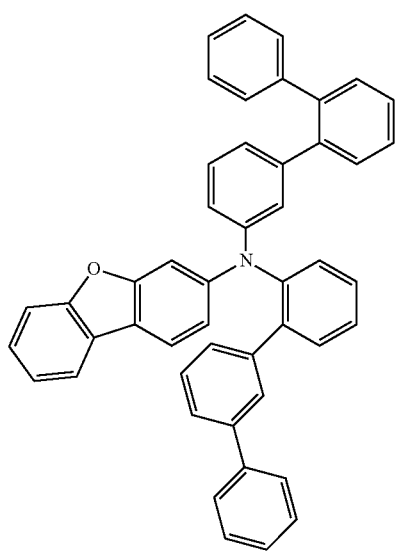
43
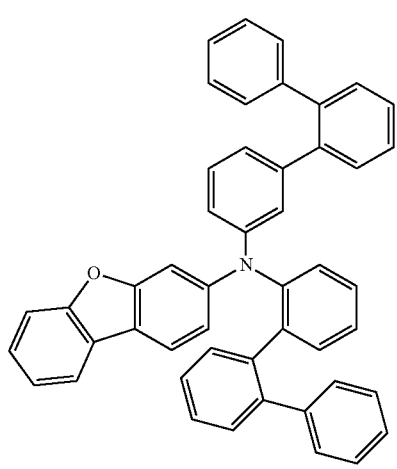
44
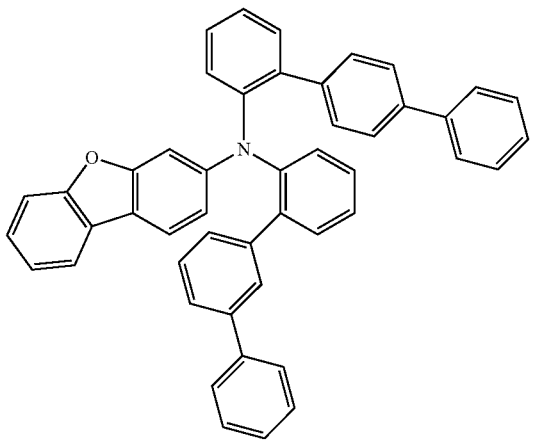
45
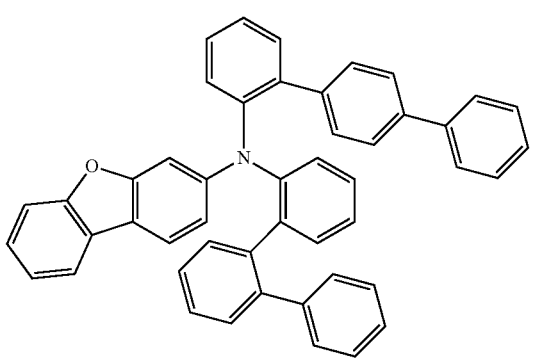
46
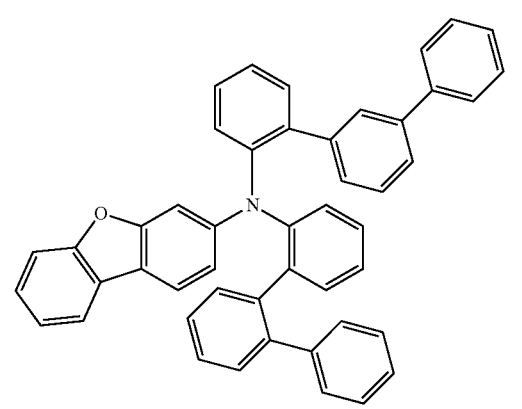

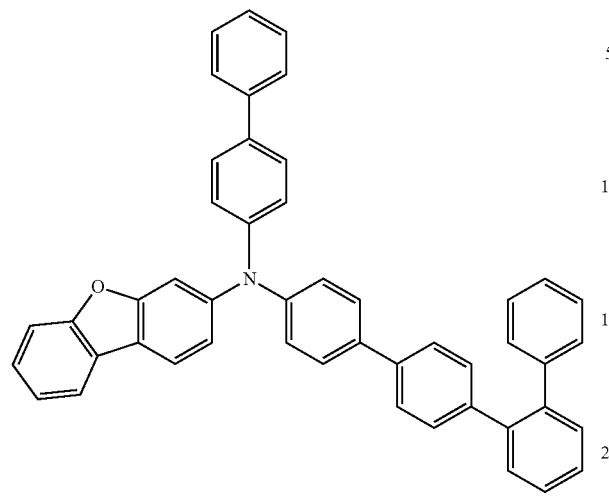
47
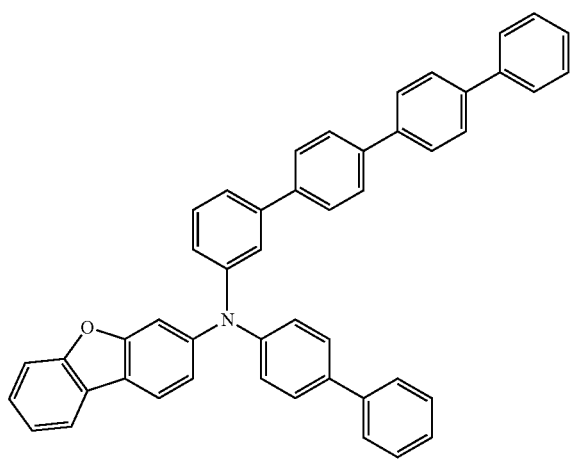
50
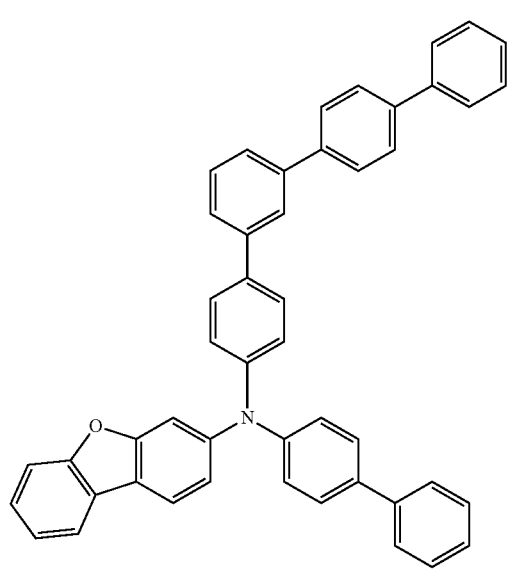
48
51
49
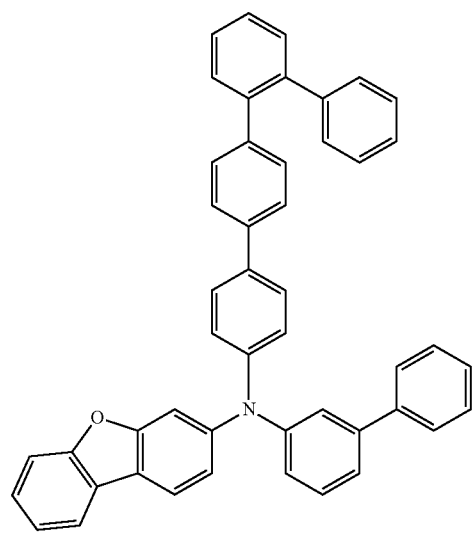
52